US006451554B1

(12) United States Patent
Wood et al.

(10) Patent No.: US 6,451,554 B1
(45) Date of Patent: Sep. 17, 2002

(54) ION CHANNEL

(75) Inventors: John Nicholas Wood; Armen Norakovitch Akopian, both of London (GB)

(73) Assignee: Ionix Pharmaceuticals Limited, Cambridgeshire (GB)

( * ) Notice: Subject to any disclaimer, the term of this patent is extended or adjusted under 35 U.S.C. 154(b) by 0 days.

(21) Appl. No.: 08/669,656

(22) Filed: Jun. 24, 1996

(30) Foreign Application Priority Data

Jun. 28, 1995 (GB) .............................................. 9513180

(51) Int. Cl.⁷ .............................................. C12N 15/12
(52) U.S. Cl. .................. 435/69.1; 536/23.5; 435/320.1; 435/325
(58) Field of Search .............................. 536/23.5, 24.3, 536/24.31, 24.33; 435/69.1, 6, 252.3, 255.1, 320.1, 325

(56) References Cited

U.S. PATENT DOCUMENTS

| | | |
|---|---|---|
| 5,380,836 A | 1/1995 | Rogart |
| 6,184,349 B1 | 2/2001 | Herman et al. |

OTHER PUBLICATIONS

Sequence Accession L42342, NCBI Entrez database, Jun. 9, 1995.
Sequence Accession M81758, NCBI Entrez database, Mar. 15, 1992.
Sequence Accession M26643, NCBI Entrez database, Nov. 23, 1989.
Sequence Accession P15389, NCBI Entrez database, Apr. 1, 1990.
Sequence Accession Q99250, NCBI Entrez database, Jun. 1, 1994.
Sequence Accession P04775, NCBI Entrez database, Aug. 13, 1987.
Sequence Accession X92184, NCBI Entrez database, Feb. 29, 1996.
Sequence Accession U53833, NCBI Entrez database, Apr. 26, 1996.
Sequence Accession P08014, NCBI Entrez database, Aug. 1, 1988.
Gellens PNAS (19192) 89, 554–558.
George (1992) AM. Neurol 13 (2), 131–137.
Trimmer (1989) Nueron 3, 33–49.
Lu (1992) FEBS L303 (1) 53–58.
Han (1991) PNAS 88 (2) 335–339.
Noda (1986) Nature 320 (6058) 188–192.
Sangameswaran (1996) J. Biol. Chem 271 (22) 13292–13292.
Kayano (1988) FEBS L 228 (1) 187–194.
Rogart, R. B. et al, "Identification of Two Sodium Channel Subtypes in Chick Heart and Brain", *Proc. Natl. Acad. Sci USA*, vol. 80, pp. 1106–1110, Feb. 1983.

Rogart, R. B. et al, "Molecular Cloning of a Putative Tetrodotoxin–Resistant Rat Heart Na+ Channel Isoform", *Proc. Natl. Acad. Sci*, USA, vol. 86, pp. 8170–8174, Oct. 1989.
Beckh, Synnove; "Differential Expression of Sodium Channel mRNAs in Rat Peripheral Nervous System and Innervated Tissues", *FEBS Letters*, vol. 262, No. 2, pp. 317–322, Mar. 1990.
Tanelian, Darrell L. et al., "Neuropathic Pain Can Be Relieved By Drugs That Are Use–dependent Sodium Channel Blockers: Lidocaine, carbamazepine, and Mexiletine", *Anaesthesiology*, 74:949–951, May 1991.
West, James W. et al., "Efficient Expression of Rat Brain Type IIA Na+ Channel α Subunits in a Somatic Cell Line", *Neuron*, vol. 8, 59–70, Jan. 1992.
Roy, Mary Louise et al., "Differential Properties of Tetrodotoxin–sensitive Textrodotoxin–resistant Sodium Channels in Rat Doral Root Ganglion Neurons", *The Journal of Neuroscience*, 12(6): 2104–2111, Jun. 1992.
Gautron, Sophie et al., "The Glial Voltage–gated Sodium Channel: Cell– and tissue–specific mRNA Expression", *Proc. Natl. Acad. Sci.*, USA, vol. 89, pp. 7272–7276, Aug. 1992.
Caffreym J. M. et al. "Three Types of Sodium Channels in Adult Rat Dorsal Root Ganglion Neurons", *Brain Research*, 492, 283–297 (1992).
Ahmed, C. M. I. et al., "Primary Structure, Chromosomal Localization, and Functional Expression of Voltage–gated Sodium Channel from Human Brain", *Proc. Natl. Acad. Sci.*USA, vol. 89, pp. 8220–8224, Sep. 1992.
Elliott, A. A., et al., "Characterization of TTX–sensitive and TTX–resistant Sodium Currents in Small Cells From Adult Rat Dorsal Root Ganglia", *Journal of Physiology* (1993), 463, pp. 39–56.
Jeftinija, Srdija, "The Role of Tetrodotoxin–Resistant Sodium Channels of Small Primary Afferent Fibers", *Brain Research* 639 (1994) 125–134.
Jeftinija, Srdija, "Bradykinin Excites Tetrodotoxin–resistant Primary Afferent Fibers", *Brain Research* 665 (1994) 69–76.
Klugbauer, Norbert et al., "Structure and Functional Expression of a New Member of the Tetrodotoxin–Sensitive Voltage–Activated Sodium Channel Family From Human Neuroendocrine Cells", *The EMBO Journal*, vol. 14, No. 6, pp. 1084–1090, 1995.
Schaller, Kristin L. et al., "A Novel, Abundant Sodium Channel Expressed in Neurons and Glia", *The Journal of Neuroscience*, May 1995, 15(5): 3231–3242.

(List continued on next page.)

*Primary Examiner*—Marianne P. Allen
(74) *Attorney, Agent, or Firm*—Nixon & Vanderhye P.C.

(57) ABSTRACT

The present invention relates to a novel 1,957 amino acid tetrodotoxin-insensitive voltage-gated sodium channel specifically located in mammalian sensory neurons. Nucleic acid sequences coding for the novel sodium channel, vectors, host cells and methods of identifying modulators of the novel sodium channel for use in treatment of pain are also provided.

17 Claims, 17 Drawing Sheets

OTHER PUBLICATIONS

Akopian, Armen et al., "Peripheral Nervous System–specific Genes Identified by Subtractive cDNA Cloning", *The Journal of Biological Chemistry*, vol. 280, No. 36, Sep. 8, 1995, pp. 21264–21270.

Akopian, Armen et al., "A Tetrodotoxin–resistant Voltage-gated Sodium Channel Expressed by Sensory Neurons", *Nature* vol. 379, Jan. 18, 1996.

Sangameswaran, Lakshmi et al, "Structure and Function of a Novel Voltae–gated Tetrodotoxin–resistant Sodium Channel Specific to Sensory Neurons", *The Journal of Biological Chemistry*, vol. 271, No. 11, pp. 5953–5956, Mar. 15, 1996.

Gene Bank accession No. U 53833 showing Rattus norvegicus sodium PN3 gene, and amino acid sequence as referred in Sangameswaran, L. et al. *J. Biol. Chem.* 271, 5953–5957 (1996).

Arbuckle, J. B. et al., "Expression of Tetrodotoxin Resistant Sodium Channels in Capsaicin–Sensitive Dorsal Root Ganglion Neurons of Adult Rats", *Neuroscience Letters*, vol. 185, pp. 70–73, 1995.

Schwartz A. et al., "Structural and Developmental Differences Between Three Types of Na Channels Roots Ganglion Cells of Newborn Rats", *Journal of Membrane Biology*, vol. 116, pp. 117–128, 1990.

Fig.1a-1

Nucleic acid and amino acid sequence of TTXi DRG sodium channel

```
    tagcttgcttctgctaatgctaccccaggcctttagacagagaacagatggcagatggag
  1 ---------+---------+---------+---------+---------+---------+
    atcgaacgaagacgattacgatggggtccggaaatctgtctcttgtctaccgtctacctc tttcttattgccatgcgcaaacgctgagcccacctcatgatcccggaccccatggttttc
 61 ---------+---------+---------+---------+---------+---------+
    aaagaataacggtacgcgtttgcgactcgggtggagtactagggcctggggtaccaaaag agtagacaacctgggctaagaagagatctccgaccttatagagcagcaaagagtgtaaat
121 ---------+---------+---------+---------+---------+---------+
    tcatctgttggacccgattcttctctagaggctggaatatctcgtcgtttctcacattta tcttccccaagaagaatgagaagATGGAGCTCCCCTTTGCGTCCGTGGGAACTACCAATT
181 ---------+---------+---------+---------+---------+---------+
    agaaggggttcttcttactcttcTACCTCGAGGGGAAACGCAGGCACCCTTGATGGTTAA
                           M  E  L  P  F  A  S  V  G  T  T  N  F TCAGACGGTTCACTCCAGAGTCACTGGCAGAGATCGAGAAGCAGATTGCTGCTCACCGGG
241 ---------+---------+---------+---------+---------+---------+
    AGTCTGCCAAGTGAGGTCTCAGTGACCGTCTCTAGCTCTTCGTCTAACGACGAGTGGCCC
     R  R  F  T  P  E  S  L  A  E  I  E  K  Q  I  A  A  H  R  A CAGCCAAGAAGGCCAGAACCAAGCACAGAGGACAGGAGGACAAGGGCGAGAAGCCCAGGC
301 ---------+---------+---------+---------+---------+---------+
    GTCGGTTCTTCCGGTCTTGGTTCGTGTCTCCTGTCCTCCTGTTCCCGCTCTTCGGGTCCG
     A  K  K  A  R  T  K  H  R  G  Q  E  D  K  G  E  K  P  R  P CTCAGCTGGACTTGAAAGACTGTAACCAGCTGCCCAAGTTCTATGGTGAGCTCCCAGCAG
361 ---------+---------+---------+---------+---------+---------+
    GAGTCGACCTGAACTTTCTGACATTGGTCGACGGGTTCAAGATACCACTCGAGGGTCGTC
     Q  L  D  L  K  D  C  N  Q  L  P  K  F  Y  G  E  L  P  A  E AACTGGTCGGGGAGCCCCTGGAGGACCTAGACCCTTTCTACAGCACACACCGGACATTCA
421 ---------+---------+---------+---------+---------+---------+
    TTGACCAGCCCCTCGGGGACCTCCTGGATCTGGGAAAGATGTCGTGTGTGGCCTGTAAGT
     L  V  G  E  P  L  E  D  L  D  P  F  Y  S  T  H  R  T  F  M TGGTGTTGAATAAAAGCAGGACCATTTCCAGATTCAGTGCCACTTGGGCCCTGTGGCTCT
481 ---------+---------+---------+---------+---------+---------+
    ACCACAACTTATTTTCGTCCTGGTAAAGGTCTAAGTCACGGTGAACCCGGGACACCGAGA
     V  L  N  K  S  R  T  I  S  R  F  S  A  T  W  A  L  W  L  F
```

Fig.1a-2

```
     TCAGTCCCTTCAACCTGATCAGAAGAACAGCCATCAAAGTGTCTGTCCATTCCTGGTTCT
541  ---------+---------+---------+---------+---------+---------+
     AGTCAGGGAAGTTGGACTAGTCTTCTTGTCGGTAGTTTCACAGACAGGTAAGGACCAAGA
      S  P  F  N  L  I  R  R  T  A  I  K  V  S  V  H  S  W  F  S

CCATATTCATCACCATCACTATTTTGGTCAACTGCGTGTGCATGACCCGAACTGATCTTC
601  ---------+---------+---------+---------+---------+---------+
     GGTATAAGTAGTGGTAGTGATAAAACCAGTTGACGCACACGTACTGGGCTTGACTAGAAG
      I  F  I  T  I  T  I  L  V  N  C  V  C  M  T  R  T  D  L  P

CAGAGAAAGTCGAGTACGTCTTCACTGTCATTTACACCTTCGAGGCTCTGATTAAGATAC
661  ---------+---------+---------+---------+---------+---------+
     GTCTCTTTCAGCTCATGCAGAAGTGACAGTAAATGTGGAAGCTCCGAGACTAATTCTATG
      E  K  V  E  Y  V  F  T  V  I  Y  T  F  E  A  L  I  K  I  L

TGGCAAGAGGGTTTTGTCTAAATGAGTTCACTTATCTTCGAGATCCGTGGAACTGGCTGG
721  ---------+---------+---------+---------+---------+---------+
     ACCGTTCTCCCAAAACAGATTTACTCAAGTGAATAGAAGCTCTAGGCACCTTGACCGACC
      A  R  G  F  C  L  N  E  F  T  Y  L  R  D  P  W  N  W  L  D

ACTTCAGTGTCATTACCTTGGCGTATGTGGGTGCAGCGATAGACCTCCGAGGAATCTCAG
781  ---------+---------+---------+---------+---------+---------+
     TGAAGTCACAGTAATGGAACCGCATACACCCACGTCGCTATCTGGAGGCTCCTTAGAGTC
      F  S  V  I  T  L  A  Y  V  G  A  A  I  D  L  R  G  I  S  -

GCCTGCGGACATTCCGAGTTCTCAGAGCCCTGAAAACTGTTTCTGTGATCCCAGGACTGA
841  ---------+---------+---------+---------+---------+---------+
     CGGACGCCTGTAAGGCTCAAGAGTCTCGGGACTTTTGACAAAGACACTAGGGTCCTGACT
      L  R  T  F  R  V  L  R  A  L  K  T  V  S  V  I  P  G  L  -

AGGTCATCGTGGGAGCCCTGATCCACTCAGTGAGGAAGCTGGCCGACGTGACTATCCTCA
901  ---------+---------+---------+---------+---------+---------+
     TCCAGTAGCACCCTCGGGACTAGGTGAGTCACTCCTTCGACCGGCTGCACTGATAGGAGT
      V  I  V  G  A  L  I  H  S  V  R  K  L  A  D  V  T  I  L  T

CAGTCTTCTGCCTGAGCGTCTTCGCCTTGGTGGGCCTGCAGCTCTTTAAGGGGAACCTTA
961  ---------+---------+---------+---------+---------+---------+
     GTCAGAAGACGGACTCGCAGAAGCGGAACCACCCGGACGTCGAGAAATTCCCCTTGGAAT
      V  F  C  L  S  V  F  A  L  V  G  L  Q  L  F  K  G  N  L  K

AGAACAAATGCATCAGGAACGGAACAGATCCCCACAAGGCTGACAACCTCTCATCTGAAA
1021 ---------+---------+---------+---------+---------+---------+
     TCTTGTTTACGTAGTCCTTGCCTTGTCTAGGGGTGTTCCGACTGTTGGAGAGTAGACTTT
      N  K  C  I  R  N  G  T  D  P  H  K  A  D  N  L  S  S  E  M

TGGCAGAATACATCTTCATCAAGCCTGGTACTACGGATCCCTTACTGTGCGGCAATGGGT
1081 ---------+---------+---------+---------+---------+---------+
     ACCGTCTTATGTAGAAGTAGTTCGGACCATGATGCCTAGGGAATGACACGCCGTTACCCA
      A  E  Y  I  F  I  K  P  G  T  T  D  P  L  L  C  G  N  G  S
```

Fig.1a-3

```
     CTGATGCTGGTCACTGCCCTGGAGGCTATGTCTGCCTGAAAACTCCTGACAACCCGGATT
1141 ------------+---------+---------+---------+---------+---------+
     GACTACGACCAGTGACGGGACCTCCGATACAGACGGACTTTTGAGGACTGTTGGGCCTAA

D  A  G  H  C  P  G  G  Y  V  C  L  K  T  P  D  N  P  D  F

TTAACTACACCAGCTTTGATTCCTTTGCGTGGGCATTCCTCTCACTGTTCCGCCTCATGA
1201 ------------+---------+---------+---------+---------+---------+
     AATTGATGTGGTCGAAACTAAGGAAACGCACCCGTAAGGAGAGTGACAAGGCGGAGTACT

N  Y  T  S  F  D  S  F  A  W  A  F  L  S  L  F  R  L  M  T

CGCAGGACTCCTGGGAGCGCCTGTACCAGCAGACACTCCGGGCTTCTGGGAAAATGTACA
1261 ------------+---------+---------+---------+---------+---------+
     GCGTCCTGAGGACCCTCGCGGACATGGTCGTCTGTGAGGCCCGAAGACCCTTTTACATGT

Q  D  S  W  E  R  L  Y  Q  Q  T  L  R  A  S  G  K  M  Y  M

TGGTCTTTTTCGTGCTGGTTATTTTCCTTGGATCGTTCTACCTGGTCAATTTGATCTTGG
1321 ------------+---------+---------+---------+---------+---------+
     ACCAGAAAAAGCACGACCAATAAAAGGAACCTAGCAAGATGGACCAGTTAAACTAGAACC

V  F  F  V  L  V  I  F  L  G  S  F  Y  L  V  N  L  I  L  A

CCGTGGTCACCATGGCGTATGAAGAGCAGAGCCAGGCAACAATTGCAGAAATCGAAGCCA
1381 ------------+---------+---------+---------+---------+---------+
     GGCACCAGTGGTACCGCATACTTCTCGTCTCGGTCCGTTGTTAACGTCTTTAGCTTCGGT

V  V  T  M  A  Y  E  E  Q  S  Q  A  T  I  A  E  I  E  A  K

AGGAAAAAAAGTTCCAGGAAGCCCTTGAGGTGCTGCAGAAGGAACAGGAGGTGCTGGCAG
1441 ------------+---------+---------+---------+---------+---------+
     TCCTTTTTTTCAAGGTCCTTCGGGAACTCCACGACGTCTTCCTTGTCCTCCACGACCGTC

E  K  K  F  Q  E  A  L  E  V  L  Q  K  E  Q  E  V  L  A  A

CCCTGGGGATTGACACGACCTCGCTCCAGTCCCACAGTGGATCACCCTTAGCCTCCAAAA
1501 ------------+---------+---------+---------+---------+---------+
     GGGACCCCTAACTGTGCTGGAGCGAGGTCAGGGTGTCACCTAGTGGGAATCGGAGGTTTT

L  G  I  D  T  T  S  L  Q  S  H  S  G  S  P  L  A  S  K  N

ACGCCAATGAGAGAAGACCCAGGGTGAAATCAAGGGTGTCAGAGGGCTCCACGGATGACA
1561 ------------+---------+---------+---------+---------+---------+
     TGCGGTTACTCTCTTCTGGGTCCCACTTTAGTTCCCACAGTCTCCCGAGGTGCCTACTGT

A  N  E  R  R  P  R  V  K  S  R  V  S  E  G  S  T  D  D  N

ACAGGTCACCCCAATCTGACCCTTACAACCAGCGCAGGATGTCTTTCCTAGGCCTGTCTT
1621 ------------+---------+---------+---------+---------+---------+
     TGTCCAGTGGGGTTAGACTGGGAATGTTGGTCGCGTCCTACAGAAAGGATCCGGACAGAA

R  S  P  Q  S  D  P  Y  N  Q  R  R  M  S  F  L  G  L  S  S

CAGGAAGACGCAGGGCTAGCCACGGCAGTGTGTTCCACTTCCGAGCGCCCAGCCAAGACA
1681 ------------+---------+---------+---------+---------+---------+
     GTCCTTCTGCGTCCCGATCGGTGCCGTCACACAAGGTGAAGGCTCGCGGGTCGGTTCTGT

```
      TCTCATTTCCTGACGGGATCACCCCTGATGATGGGGTCTTTCACGGAGACCAGGAAAGCC
1741  ------------------------------------------------------------+
      AGAGTAAAGGACTGCCCTAGTGGGGACTACTACCCCAGAAAGTGCCTCTGGTCCTTTCGG
       S  F  P  D  G  I  T  P  D  D  G  V  F  H  G  D  Q  E  S  R

GTCGAGGTTCCATATTGCTGGGCAGGGGTGCTGGGCAGACAGGTCCACTCCCCAGGAGCC
1801  ------------------------------------------------------------+
      CAGCTCCAAGGTATAACGACCCGTCCCCACGACCCGTCTGTCCAGGTGAGGGGTCCTCGG
        R  G  S  I  L  L  G  R  G  A  G  Q  T  G  P  L  P  R  S  P

CACTGCCTCAGTCCCCCAACCCTGGCCGTAGACATGGAGAAGAGGGACAGCTCGGAGTGC
1861  ------------------------------------------------------------+
      GTGACGGAGTCAGGGGGTTGGGACCGGCATCTGTACCTCTTCTCCCTGTCGAGCCTCACG
       L  P  Q  S  P  N  P  G  R  R  H  G  E  E  G  Q  L  G  V  P

CCACTGGTGAGCTTACCGCTGGAGCGCCTGAAGGCCCGGCACTCGACACTACAGGGCAGA
1921  ------------------------------------------------------------+
      GGTGACCACTCGAATGGCGACCTCGCGGACTTCCGGGCCGTGAGCTGTGATGTCCCGTCT
       T  G  E  L  T  A  G  A  P  E  G  P  A  L  D  T  T  G  Q  K

AGAGCTTCCTGTCTGCGGGCTACTTGAACGAACCTTTCCGAGCACAGAGGGCCATGAGCG
1981  ------------------------------------------------------------+
      TCTCGAAGGACAGACGCCCGATGAACTTGCTTGGAAAGGCTCGTGTCTCCCGGTACTCGC
        S  F  L  S  A  G  Y  L  N  E  P  F  R  A  Q  R  A  M  S  V

TTGTCAGTATCATGACTTCTGTCATTGAGGAGCTTGAAGAGTCTAAGCTGAAGTGCCCAC
2041  ------------------------------------------------------------+
      AACAGTCATAGTACTGAAGACAGTAACTCCTCGAACTTCTCAGATTCGACTTCACGGGTG
       V  S  I  M  T  S  V  I  E  E  L  E  E  S  K  L  K  C  P  P

CCTGCTTGATCAGCTTCGCTCAGAAGTATCTGATCTGGGAGTGCTGCCCCAAGTGGAGGA
2101  ------------------------------------------------------------+
      GGACGAACTAGTCGAAGCGAGTCTTCATAGACTAGACCCTCACGACGGGGTTCACCTCCT
        C  L  I  S  F  A  Q  K  Y  L  I  W  E  C  C  P  K  W  R  K

AGTTCAAGATGGCGCTGTTCGAGCTGGTGACTGACCCCTTCGCAGAGCTTACCATCACCC
2161  ------------------------------------------------------------+
      TCAAGTTCTACCGCGACAAGCTCGACCACTGACTGGGGAAGCGTCTCGAATGGTAGTGGG
       F  K  M  A  L  F  E  L  V  T  D  P  F  A  E  L  T  I  T  L

TCTGCATCGTGGTGAACACCGTCTTCATGGCCATGGAGCACTACCCCATGACCGATGCCT
2221  ------------------------------------------------------------+
      AGACGTAGCACCACTTGTGGCAGAAGTACCGGTACCTCGTGATGGGGTACTGGCTACGGA
        C  I  V  V  N  T  V  F  M  A  M  E  H  Y  P  M  T  D  A  F

TCGATGCCATGCTTCAAGCCGGCAACATTGTCTTCACCGTGTTTTTCACAATGGAGATGG
2281  ------------------------------------------------------------+
      AGCTACGGTACGAAGTTCGGCCGTTGTAACAGAAGTGGCACAAAAAGTGTTACCTCTACC
       D  A  M  L  Q  A  G  N  I  V  F  T  V  F  F  T  M  E  M  A
```

Fig.1a-5

```
        CCTTCAAGATCATTGCCTTCGACCCCTACTATTACTTCCAGAAGAAGTGGAATATCTTCG
2341    ------------+---------+---------+---------+---------+---------+
        GGAAGTTCTAGTAACGGAAGCTGGGGATGATAATGAAGGTCTTCTTCACCTTATAGAAGC

F  K  I  I  A  F  D  P  Y  Y  F  Q  K  K  W  N  I  F  D

ACTGTGTCATCGTCACCGTGAGCCTTCTGGAGCTGAGTGCATCCAAGAAGGGCAGCCTGT
2401    ------------+---------+---------+---------+---------+---------+
        TGACACAGTAGCAGTGGCACTCGGAAGACCTCGACTCACGTAGGTTCTTCCCGTCGGACA

C  V  I  V  T  V  S  L  L  E  L  S  A  S  K  K  G  S  L  S

CTGTGCTCCGTTCCTTACGCTTGCTGCGGGTCTTCAAGCTGGCCAAGTCCTGGCCCACCC
2461    ------------+---------+---------+---------+---------+---------+
        GACACGAGGCAAGGAATGCGAACGACGCCCAGAAGTTCGACCGGTTCAGGACCGGGTGGG

V  L  R  S  L  R  L  L  R  V  F  K  L  A  K  S  W  P  T  L

TGAACACCCTCATCAAGATCATCGGGAACTCAGTGGGGGCCCTGGGCAACCTGACCTTTA
2521    ------------+---------+---------+---------+---------+---------+
        ACTTGTGGGAGTAGTTCTAGTAGCCCTTGAGTCACCCCCGGGACCCGTTGGACTGGAAAT

N  T  L  I  K  I  I  G  N  S  V  G  A  L  G  N  L  T  F  I

TCCTGGCCATCATCGTCTTCATCTTCGCCCTGGTCGGAAAGCAGCTTCTCTCAGAGGACT
2581    ------------+---------+---------+---------+---------+---------+
        AGGACCGGTAGTAGCAGAAGTAGAAGCGGGACCAGCCTTTCGTCGAAGAGAGTCTCCTGA

L  A  I  I  V  F  I  F  A  L  V  G  K  Q  L  L  S  E  D  Y

ACGGGTGCCGCAAGGACGGCGTCTCCGTGTGGAACGGCGAGAAGCTCCGCTGGCACATGT
2641    ------------+---------+---------+---------+---------+---------+
        TGCCCACGGCGTTCCTGCCGCAGAGGCACACCTTGCCGCTCTTCGAGGCGACCGTGTACA

G  C  R  K  D  G  V  S  V  W  N  G  E  K  L  R  W  H  M  C

GTGACTTCTTCCATTCCTTCCTGGTCGTCTTCCGAATCCTCTGCGGGGAGTGGATCGAGA
2701    ------------+---------+---------+---------+---------+---------+
        CACTGAAGAAGGTAAGGAAGGACCAGCAGAAGGCTTAGGAGACGCCCCTCACCTAGCTCT

D  F  F  H  S  F  L  V  V  F  R  I  L  C  G  E  W  I  E  N

ACATGTGGGTCTGCATGGAGGTCAGCCAGAAATCCATCTGCCTCATCCTCTTCTTGACTG
2761    ------------+---------+---------+---------+---------+---------+
        TGTACACCCAGACGTACCTCCAGTCGGTCTTTAGGTAGACGGAGTAGGAGAAGAACTGAC

M  W  V  C  M  E  V  S  Q  K  S  I  C  L  I  L  F  L  T  V

TGATGGTGCTGGGCAACCTAGTGGTGCTCAACCTTTTCATCGCTTTACTGCTGAACTCCT
2821    ------------+---------+---------+---------+---------+---------+
        ACTACCACGACCCGTTGGATCACCACGAGTTGGAAAAGTAGCGAAATGACGACTTGAGGA

M  V  L  G  N  L  V  V  L  N  L  F  I  A  L  L  L  N  S  F

TCAGCGCGGACAACCTCACGGCTCCAGAGGATGACGGGGAGGTGAACAACTTGCAGTTAG
2881    ------------+---------+---------+---------+---------+---------+
        AGTCGCGCCTGTTGGAGTGCCGAGGTCTCCTACTGCCCCTCCACTTGTTGAACGTCAATC

```
           CACTGGCCAGGATCCAGGTACTTGGCCATCGGGCCAGCAGGGCCATCGCCAGTTACATCA
2941       ---------+---------+---------+---------+---------+---------+
           GTGACCGGTCCTAGGTCCATGAACCGGTAGCCCGGTCGTCCCGGTAGCGGTCAATGTAGT

L  A  R  I  Q  V  L  G  H  R  A  S  R  A  I  A  S  Y  I  S

GCAGCCACTGCCGATTCCGCTGGCCCAAGGTGGAGACCCAGCTGGGCATGAAGCCCCCAC
3001       ---------+---------+---------+---------+---------+---------+
           CGTCGGTGACGGCTAAGGCGACCGGGTTCCACCTCTGGGTCGACCCGTACTTCGGGGGTG

S  H  C  R  F  R  W  P  K  V  E  T  Q  L  G  M  K  P  P  L

TCACCAGCTCAGAGGCCAAGAACCACATTGCCACTGATGCTGTCAGTGCTGCAGTGGGGA
3061       ---------+---------+---------+---------+---------+---------+
           AGTGGTCGAGTCTCCGGTTCTTGGTGTAACGGTGACTACGACAGTCACGACGTCACCCCT

T  S  S  E  A  K  N  H  I  A  T  D  A  V  S  A  A  V  G  N

ACCTGACAAAGCCAGCTCTCAGTAGCCCCAAGGAGAATCACGGGGACTTCATCACTGATC
3121       ---------+---------+---------+---------+---------+---------+
           TGGACTGTTTCGGTCGAGAGTCATCGGGGTTCCTCTTAGTGCCCCTGAAGTAGTGACTAG

L  T  K  P  A  L  S  S  P  K  E  N  H  G  D  F  I  T  D  P

CCAACGTGTGGGTCTCTGTGCCCATTGCTGAGGGGGAATCTGACCTCGACGAGCTCGAGG
3181       ---------+---------+---------+---------+---------+---------+
           GGTTGCACACCCAGAGACACGGGTAACGACTCCCCCTTAGACTGGAGCTGCTCGAGCTCC

N  V  W  V  S  V  P  I  A  E  G  E  S  D  L  D  E  L  E  E

AAGATATGGAGCAGGCTTCGCAGAGCTCCTGGCAGGAAGAGGACCCCAAGGGACAGCAGG
3241       ---------+---------+---------+---------+---------+---------+
           TTCTATACCTCGTCCGAAGCGTCTCGAGGACCGTCCTTCTCCTGGGGTTCCCTGTCGTCC

D  M  E  Q  A  S  Q  S  S  W  Q  E  E  D  P  K  G  Q  Q  E

AGCAGTTGCCACAAGTCCAAAAGTGTGAAAACCACCAGGCAGCCAGAAGCCCAGCCTCCA
3301       ---------+---------+---------+---------+---------+---------+
           TCGTCAACGGTGTTCAGGTTTTCACACTTTTGGTGGTCCGTCGGTCTTCGGGTCGGAGGT

Q  L  P  Q  V  Q  K  C  E  N  H  Q  A  A  R  S  P  A  S  M

TGATGTCCTCTGAGGACCTGGCTCCATACCTGGGTGAGAGCTGGAAGAGGAAGGATAGCC
3361       ---------+---------+---------+---------+---------+---------+
           ACTACAGGAGACTCCTGGACCGAGGTATGGACCCACTCTCGACCTTCTCCTTCCTATCGG

M  S  S  E  D  L  A  P  Y  L  G  E  S  W  K  R  K  D  S  P

CTCAGGTCCCTGCCGAGGGAGTGGATGACACGAGCTCCTCTGAGGGCAGCACGGTGGACT
3421       ---------+---------+---------+---------+---------+---------+
           GAGTCCAGGGACGGCTCCCTCACCTACTGTGCTCGAGGAGACTCCCGTCGTGCCACCTGA

Q  V  P  A  E  G  V  D  D  T  S  S  S  E  G  S  T  V  D  C

GCCCGGACCCAGAGGAAATCCTGAGGAAGATCCCCGAGCTGGCAGATGACCTGGACGAGC
3481       ---------+---------+---------+---------+---------+---------+
           CGGGCCTGGGTCTCCTTTAGGACTCCTTCTAGGGGCTCGACCGTCTACTGGACCTGCTCG

```
         CCGATGACTGTTTCACAGAAGGCTGCACTCGCCGCTGTCCCTGCTGCAACGTGAATACTA
3541     ----------+---------+---------+---------+---------+---------+
         GGCTACTGACAAAGTGTCTTCCGACGTGAGCGGCGACAGGGACGACGTTGCACTTATGAT
          D  D  C  F  T  E  G  C  T  R  R  C  P  C  C  N  V  N  T  S

GCAAGTCTCCTTGGGCCACAGGCTGGCAGGTGCGCAAGACCTGCTACCGCATCGTGGAGC
3601     ----------+---------+---------+---------+---------+---------+
         CGTTCAGAGGAACCCGGTGTCCGACCGTCCACGCGTTCTGGACGATGGCGTAGCACCTCG
          K  S  P  W  A  T  G  W  Q  V  R  K  T  C  Y  R  I  V  E  H

ACAGCTGGTTTGAGAGTTTCATCATCTTCATGATCCTGCTCAGCAGTGGAGCGCTGGCCT
3661     ----------+---------+---------+---------+---------+---------+
         TGTCGACCAAACTCTCAAAGTAGTAGAAGTACTAGGACGAGTCGTCACCTCGCGACCGGA
          S  W  F  E  S  F  I  I  F  M  I  L  L  S  S  G  A  L  A  F

TTGAGGATAACTACCTGGAAGAGAAACCCCGAGTGAAGTCCGTGCTGGAGTACACTGACC
3721     ----------+---------+---------+---------+---------+---------+
         AACTCCTATTGATGGACCTTCTCTTTGGGGCTCACTTCAGGCACGACCTCATGTGACTGG
          E  D  N  Y  L  E  E  K  P  R  V  K  S  V  L  E  Y  T  D  R

GAGTGTTCACCTTCATCTTCGTCTTTGAGATGCTGCTCAAGTGGGTAGCCTATGGCTTCA
3781     ----------+---------+---------+---------+---------+---------+
         CTCACAAGTGGAAGTAGAAGCAGAAACTCTACGACGAGTTCACCCATCGGATACCGAAGT
          V  F  T  F  I  F  V  F  E  M  L  L  K  W  V  A  Y  G  F  K

AAAAGTATTTCACCAATGCCTGGTGCTGGCTGGACTTCCTCATTGTGAACATCTCCCTGA
3841     ----------+---------+---------+---------+---------+---------+
         TTTTCATAAAGTGGTTACGGACCACGACCGACCTGAAGGAGTAACACTTGTAGAGGGACT
          K  Y  F  T  N  A  W  C  W  L  D  F  L  I  V  N  I  S  L  T

CAAGCCTCATAGCGAAGATCCTTGAGTATTCCGACGTGGCGTCCATCAAAGCCCTTCGGA
3901     ----------+---------+---------+---------+---------+---------+
         GTTCGGAGTATCGCTTCTAGGAACTCATAAGGCTGCACCGCAGGTAGTTTCGGGAAGCCT
          S  L  I  A  K  I  L  E  Y  S  D  V  A  S  I  K  A  L  R  T

CTCTCCGTGCCCTCCGACCGCTGCGGGCTCTGTCTCGATTCGAAGGCATGAGGGTAGTGG
3961     ----------+---------+---------+---------+---------+---------+
         GAGAGGCACGGGAGGCTGGCGACGCCCGAGACAGAGCTAAGCTTCCGTACTCCCATCACC
          L  R  A  L  R  P  L  R  A  L  S  R  F  E  G  M  R  V  V  V

TGGATGCCCTCGTGGGCGCCATCCCCTCCATCATGAACGTCCTCCTCGTCTGCCTCATCT
4021     ----------+---------+---------+---------+---------+---------+
         ACCTACGGGAGCACCCGCGGTAGGGGAGGTAGTACTTGCAGGAGGAGCAGACGGAGTAGA
          D  A  L  V  G  A  I  P  S  I  M  N  V  L  L  V  C  L  I  F

TCTGGCTCATCTTCAGCATCATGGGCGTGAACCTCTTCGCCGGGAAATTTTCGAAGTGCG
4081     ----------+---------+---------+---------+---------+---------+
         AGACCGAGTAGAAGTCGTAGTACCCGCACTTGGAGAAGCGGCCCTTTAAAAGCTTCACGC
          W  L  I  F  S  I  M  G  V  N  L  F  A  G  K  F  S  K  C  V
```

Fig. 1a-8

```
        TCGACACCAGAAATAACCCATTTTCCAACGTGAATTCGACGATGGTGAATAACAAGTCCG
4141    ---------+---------+---------+---------+---------+---------+
        AGCTGTGGTCTTTATTGGGTAAAAGGTTGCACTTAAGCTGCTACCACTTATTGTTCAGGC
         D  T  R  N  N  P  F  S  N  V  N  S  T  M  V  N  N  K  S  E

AGTGTCACAATCAAAACAGCACCGGCCACTTCTTCTGGGTCAACGTCAAAGTCAACTTCG
4201    ---------+---------+---------+---------+---------+---------+
        TCACAGTGTTAGTTTTGTCGTGGCCGGTGAAGAAGACCCAGTTGCAGTTTCAGTTGAAGC
         C  H  N  Q  N  S  T  G  H  F  F  W  V  N  V  K  V  N  F  D

ACAACGTCGCTATGGGCTACCTCGCACTTCTTCAGGTGGCAACCTTCAAAGGCTGGATGG
4261    ---------+---------+---------+---------+---------+---------+
        TGTTGCAGCGATACCCGATGGAGCGTGAAGAAGTCCACCGTTGGAAGTTTCCGACCTACC
         N  V  A  M  G  Y  L  A  L  L  Q  V  A  T  F  K  G  W  M  D

ACATAATGTATGCAGCTGTTGATTCCGGAGAGATCAACAGTCAGCCTAACTGGGAGAACA
4321    ---------+---------+---------+---------+---------+---------+
        TGTATTACATACGTCGACAACTAAGGCCTCTCTAGTTGTCAGTCGGATTGACCCTCTTGT
         I  M  Y  A  A  V  D  S  G  E  I  N  S  Q  P  N  W  E  N  N

ACTTGTACATGTACCTGTACTTCGTCGTTTTCATCATTTTCGGTGGCTTCTTCACGCTGA
4381    ---------+---------+---------+---------+---------+---------+
        TGAACATGTACATGGACATGAAGCAGCAAAAGTAGTAAAAGCCACCGAAGAAGTGCGACT
         L  Y  M  Y  L  Y  F  V  V  F  I  I  F  G  G  F  F  T  L  N

ATCTCTTTGTTGGGGTCATAATCGACAACTTCAACCAACAGAAAAAAAAGCTAGGAGGCC
4441    ---------+---------+---------+---------+---------+---------+
        TAGAGAAACAACCCCAGTATTAGCTGTTGAAGTTGGTTGTCTTTTTTTTCGATCCTCCGG
         L  F  V  G  V  I  I  D  N  F  N  Q  Q  K  K  K  L  G  G  Q

AGGACATCTTCATGACAGAAGAGCAGAAGAAGTACTACAATGCCATGAAGAAGCTGGGCT
4501    ---------+---------+---------+---------+---------+---------+
        TCCTGTAGAAGTACTGTCTTCTCGTCTTCTTCATGATGTTACGGTACTTCTTCGACCCGA
         D  I  F  M  T  E  E  Q  K  K  Y  Y  N  A  M  K  K  L  G  S

CCAAGAAACCCCAGAAGCCCATCCCACGGCCCCTGAATAAGTACCAAGGCTTCGTGTTTG
4561    ---------+---------+---------+---------+---------+---------+
        GGTTCTTTGGGGTCTTCGGGTAGGGTGCCGGGGACTTATTCATGGTTCCGAAGCACAAAC
         K  K  P  Q  K  P  I  P  R  P  L  N  K  Y  Q  G  F  V  F  D

ACATCGTGACCAGGCAAGCCTTTGACATCATCATCATGGTTCTCATCTGCCTCAACATGA
4621    ---------+---------+---------+---------+---------+---------+
        TGTAGCACTGGTCCGTTCGGAAACTGTAGTAGTAGTACCAAGAGTAGACGGAGTTGTACT
         I  V  T  R  Q  A  F  D  I  I  I  M  V  L  I  C  L  N  M  I

TCACCATGATGGTGGAGACCGACGAGCAGGGCGAGGAGAAGACGAAGGTTCTGGGCAGAA
4681    ---------+---------+---------+---------+---------+---------+
        AGTGGTACTACCACCTCTGGCTGCTCGTCCCGCTCCTCTTCTGCTTCCAAGACCCGTCTT
         T  M  M  V  E  T  D  E  Q  G  E  E  K  T  K  V  L  G  R  I
```

Fig. 1a-9

```
       TCAACCAGTTCTTTGTGGCCGTCTTCACGGGCGAGTGTGTGATGAAGATGTTCGCCCTGC
4741   ---------+---------+---------+---------+---------+---------+
       AGTTGGTCAAGAAACACCGGCAGAAGTGCCCGCTCACACACTACTTCTACAAGCGGGACG
        N  Q  F  F  V  A  V  F  T  G  E  C  V  M  K  M  F  A  L  R

GACAGTACTACTTCACCAACGGCTGGAACGTGTTCGACTTCATAGTGGTGATCCTGTCCA
4801   ---------+---------+---------+---------+---------+---------+
       CTGTCATGATGAAGTGGTTGCCGACCTTGCACAAGCTGAAGTATCACCACTAGGACAGGT
         Q  Y  Y  F  T  N  G  W  N  V  F  D  F  I  V  V  I  L  S  I

TTGGGAGTCTGCTGTTTTCTGCAATCCTTAAGTCACTGGAAAACTACTTCTCCCCGACGC
4861   ---------+---------+---------+---------+---------+---------+
       AACCCTCAGACGACAAAAGACGTTAGGAATTCAGTGACCTTTTGATGAAGAGGGGCTGCG
         G  S  L  L  F  S  A  I  L  K  S  L  E  N  Y  F  S  P  T  L

TCTTCCGGGTCATCCGTCTGGCCAGGATCGGCCGCATCCTCAGGCTGATCCGAGCAGCCA
4921   ---------+---------+---------+---------+---------+---------+
       AGAAGGCCCAGTAGGCAGACCGGTCCTAGCCGGCGTAGGAGTCCGACTAGGCTCGTCGGT
         F  R  V  I  R  L  A  R  I  G  R  I  L  R  L  I  R  A  A  K

AGGGGATTCGCACGCTGCTCTTCGCCCTCATGATGTCCCTGCCCGCCCTCTTCAACATCG
4981   ---------+---------+---------+---------+---------+---------+
       TCCCCTAAGCGTGCGACGAGAAGCGGGAGTACTACAGGGACGGGCGGGAGAAGTTGTAGC
         G  I  R  T  L  L  F  A  L  M  M  S  L  P  A  L  F  N  I  G

GCCTCCTCCTCTTCCTCGTCATGTTCATCTACTCCATCTTCGGCATGGCCAGCTTCGCTA
5041   ---------+---------+---------+---------+---------+---------+
       CGGAGGAGGAGAAGGAGCAGTACAAGTAGATGAGGTAGAAGCCGTACCGGTCGAAGCGAT
         L  L  L  F  L  V  M  F  I  Y  S  I  F  G  M  A  S  F  A  N

ACGTCGTGGACGAGGCCGGCATCGACGACATGTTCAACTTCAAGACCTTTGGCAACAGCA
5101   ---------+---------+---------+---------+---------+---------+
       TGCAGCACCTGCTCCGGCCGTAGCTGCTGTACAAGTTGAAGTTCTGGAAACCGTTGTCGT
         V  V  D  E  A  G  I  D  D  M  F  N  F  K  T  F  G  N  S  M

TGCTGTGCCTGTTCCAGATCACCACCTCGGCCGGCTGGGACGGCCTCCTCAGCCCCATCC
5161   ---------+---------+---------+---------+---------+---------+
       ACGACACGGACAAGGTCTAGTGGTGGAGCCGGCCGACCCTGCCGGAGGAGTCGGGGTAGG
         L  C  L  F  Q  I  T  T  S  A  G  W  D  G  L  L  S  P  I  L

TCAACACGGGGCCTCCCTACTGCGACCCCAACCTGCCCAACAGCAACGGCTCCCGGGGGA
5221   ---------+---------+---------+---------+---------+---------+
       AGTTGTGCCCCGGAGGGATGACGCTGGGGTTGGACGGGTTGTCGTTGCCGAGGGCCCCT
         N  T  G  P  P  Y  C  D  P  N  L  P  N  S  N  G  S  R  G  N

ACTGCGGGAGCCCGGCGGTGGGCATCATCTTCTTCACCACCTACATCATCATCTCCTTCC
5281   ---------+---------+---------+---------+---------+---------+
       TGACGCCCTCGGGCCGCCACCCGTAGTAGAAGAAGTGGTGGATGTAGTAGTAGAGGAAGG
         C  G  S  P  A  V  G  I  I  F  F  T  T  Y  I  I  I  S  F  L
```

Fig. 1a-10

```
            TCATCGTGGTCAACATGTACATCGCAGTGATTCTGGAGAACTTCAACGTAGCCACCGAGG
5341        ----------+---------+---------+---------+---------+---------+
            AGTAGCACCAGTTGTACATGTAGCGTCACTAAGACCTCTTGAAGTTGCATCGGTGGCTCC
             I  V  V  N  M  Y  I  A  V  I  L  E  N  F  N  V  A  T  E  E

AGAGCACGGAGCCCCTGAGCGAGGACGACTTCGACATGTTCTATGAGACCTGGGAGAAGT
5401        ----------+---------+---------+---------+---------+---------+
            TCTCGTGCCTCGGGGACTCGCTCCTGCTGAAGCTGTACAAGATACTCTGGACCCTCTTCA
              S  T  E  P  L  S  E  D  D  F  D  M  F  Y  E  T  W  E  K  F

TCGACCCGGAGGCCACCCAGTTCATTGCCTTTTCTGCCCTCTCAGACTTCGCGGACACGC
5461        ----------+---------+---------+---------+---------+---------+
            AGCTGGGCCTCCGGTGGGTCAAGTAACGGAAAAGACGGGAGAGTCTGAAGCGCCTGTGCG
             D  P  E  A  T  Q  F  I  A  F  S  A  L  S  D  F  A  D  T  L

TCTCCGGCCCTCTTAGAATCCCCAAACCCAACCAGAATATATTAATCCAGATGGACCTGC
5521        ----------+---------+---------+---------+---------+---------+
            AGAGGCCGGGAGAATCTTAGGGGTTTGGGTTGGTCTTATATAATTAGGTCTACCTGGACG
             S  G  P  L  R  I  P  K  P  N  Q  N  I  L  I  Q  M  D  L  P

CGTTGGTCCCCGGGGATAAGATCCACTGTCTGGACATCCTTTTTGCCTTCACAAAGAACG
5581        ----------+---------+---------+---------+---------+---------+
            GCAACCAGGGGCCCCTATTCTAGGTGACAGACCTGTAGGAAAAACGGAAGTGTTTCTTGC
             L  V  P  G  D  K  I  H  C  L  D  I  L  F  A  F  T  K  N  V

TCTTGGGAGAATCCGGGGAGTTGGACTCCCTGAAGACCAATATGGAAGAGAAGTTTATGG
5641        ----------+---------+---------+---------+---------+---------+
            AGAACCCTCTTAGGCCCCTCAACCTGAGGGACTTCTGGTTATACCTTCTCTTCAAATACC
              L  G  E  S  G  E  L  D  S  L  K  T  N  M  E  E  K  F  M  A

CGACCAATCTCTCCAAAGCATCCTATGAACCAATAGCCACCACCCTCCGGTGGAAGCAGG
5701        ----------+---------+---------+---------+---------+---------+
            GCTGGTTAGAGAGGTTTCGTAGGATACTTGGTTATCGGTGGTGGGAGGCCACCTTCGTCC
              T  N  L  S  K  A  S  Y  E  P  I  A  T  T  L  R  W  K  Q  E

AAGACCTCTCAGCCACAGTCATTCAAAAGGCCTACCGGAGCTACATGCTGCACCGCTCCT
5761        ----------+---------+---------+---------+---------+---------+
            TTCTGGAGAGTCGGTGTCAGTAAGTTTTCCGGATGGCCTCGATGTACGACGTGGCGAGGA
             D  L  S  A  T  V  I  Q  K  A  Y  R  S  Y  M  L  H  R  S  L

TGACACTCTCCAACACCCTGCATGTGCCCAGGGCTGAGGAGGATGGCGTGTCACTTCCCG
5821        ----------+---------+---------+---------+---------+---------+
            ACTGTGAGAGGTTGTGGGACGTACACGGGTCCCGACTCCTCCTACCGCACAGTGAAGGGC
              T  L  S  N  T  L  H  V  P  R  A  E  E  D  G  V  S  L  P  G

GGGAAGGCTACAGTACATTCATGGCAAACAGTGGACTCCCGGACAAATCAGAAACTGCCT
5881        ----------+---------+---------+---------+---------+---------+
            CCCTTCCGATGTCATGTAAGTACCGTTTGTCACCTGAGGGCCTGTTTAGTCTTTGACGGA
              E  G  Y  S  T  F  M  A  N  S  G  L  P  D  K  S  E  T  A  S
```

Fig. 1a-11

```
     CTGCTACGTCTTTCCCGCCATCCTATGACAGTGTCACCAGGGGCCTGAGTGACCGGGCCA
5941 ------------+---------+---------+---------+---------+---------+
     GACGATGCAGAAAGGGCGGTAGGATACTGTCACAGTGGTCCCCGGACTCACTGGCCCGGT

A  T  S  F  P  P  S  Y  D  S  V  T  R  G  L  S  D  R  A  N

ACATTAACCCATCTAGCTCAATGCAAAATGAAGATGAGGTCGCTGCTAAGGAAGGAAACA
6001 ------------+---------+---------+---------+---------+---------+
     TGTAATTGGGTAGATCGAGTTACGTTTTACTTCTACTCCAGCGACGATTCCTTCCTTTGT

I  N  P  S  S  M  Q  N  E  D  E  V  A  A  K  E  G  N  S

GCCCTGGACCTCAGTGAaggcactcaggcatgcacagggcaggttccaatgtctttctct
6061 ------------+---------+---------+---------+---------+---------+
     CGGGACCTGGAGTCACTtccgtgagtccgtacgtgtcccgtccaaggttacagaaagaga

P  G  P  Q  * gctgtactaactccttccctctggaggtggcaccaacctccagcctccaccaatgcatgt
6121 ------------+---------+---------+---------+---------+---------+
     cgacatgattgaggaagggagacctccaccgtggttggaggtcggaggtggttacgtaca cactggtcatggtgtcagaactgaatggggacatccttgagaaagcccccaccccaatag
6181 ------------+---------+---------+---------+---------+---------+
     gtgaccagtaccacagtcttgacttaccctgtaggaactctttcgggggtggggttatc gaatcaaaagccaaggatactcctccattctgacgtcccttccgagttcccagaagatgt
6241 ------------+---------+---------+---------+---------+---------+
     cttagttttcggttcctatgaggaggtaagactgcagggaaggctcaagggtcttctaca cattgctcccttctgtttgtgaccagagacgtgattcaccaacttctcggagccagagac
6301 ------------+---------+---------+---------+---------+---------+
     gtaacgagggaagacaaacactggtctctgcactaagtggttgaagagcctcggtctctg acatagcaaagacttttctgctggtgtcgggcagtcttagagaagtcacgtaggggttgg
6361 ------------+---------+---------+---------+---------+---------+
     tgtatcgtttctgaaaagacgaccacagcccgtcagaatctcttcagtgcatccccaacc tactgagaattagggtttgcatgactgcatgctcacagctgccggacaatacctgtgagt
6421 ------------+---------+---------+---------+---------+---------+
     atgactcttaatcccaaacgtactgacgtacgagtgtcgacggcctgttatggacactca cggccattaaaattaatattttaaagttaaaaaaaaaaaaaa
6481 ------------+---------+---------+---------+----    6524
     gccggtaattttaattataaaatttcaattttttttttttttt
```

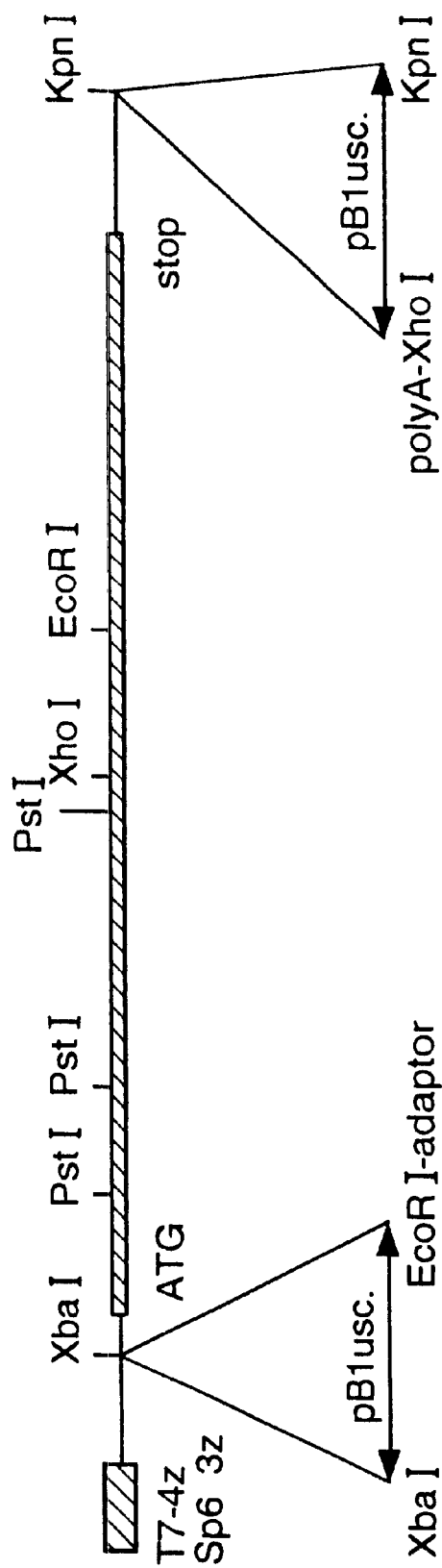

Fig. 1c
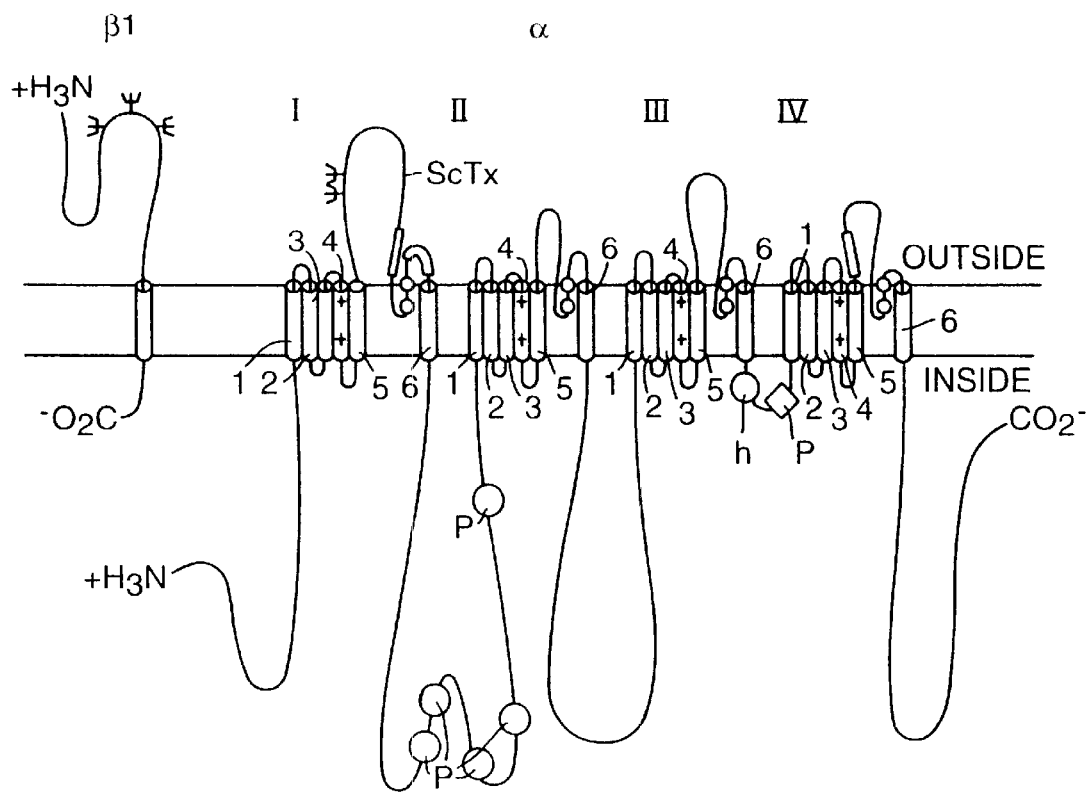
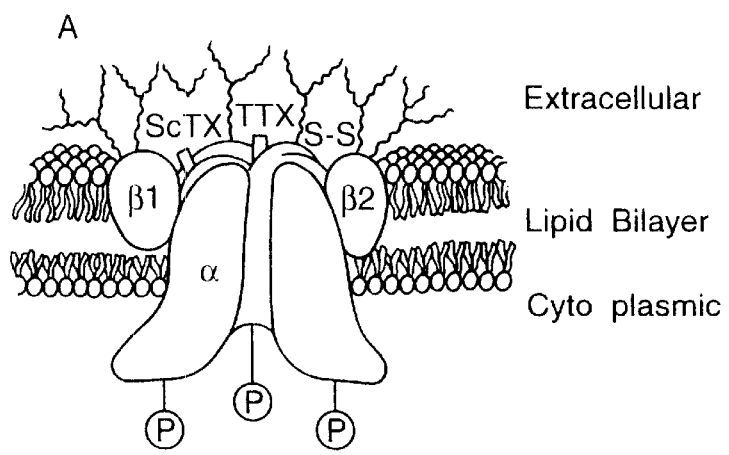
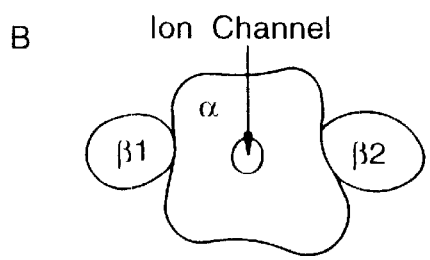

Fig.2

Sequence of PCR primers for isolation of human clone probes a) *Highly conserved regions of all sodium channels*

1) Position 2475-2510 S4 Domain II

Degenerate primers (20-24mers) encoding amino acid residues RLLRVFKLAKSWPTL or non degenerate primers within this region e.g. 5' gcttgctgcgggtcttcaagc 3'

2) Position 3961 - 4010      S4 Domain III

Degenerate primers encoding the complementary strand encoding residues LRALPLRALSRFEG or non degenerate primers within this region e.g. 5' atcgagacagagcccgcagcg 3' b) *Unique sequence primers for SNS-homologues* e.g. residues with the region 2641-2680 e.g. 5' acgggtgccgcaaggacggcgtctccgtgtggaacggcgagaag 3' and complementary sequence within the region 3375 and 3420 e.g. 5' ggctatccttcctcttccagctctcacccaggtatggagccaggt 3'

Fig.3

In vitro synthesis of S-35 methionine labelled SNS-B voltage gated sodium channel in a coupled transcription/translation system

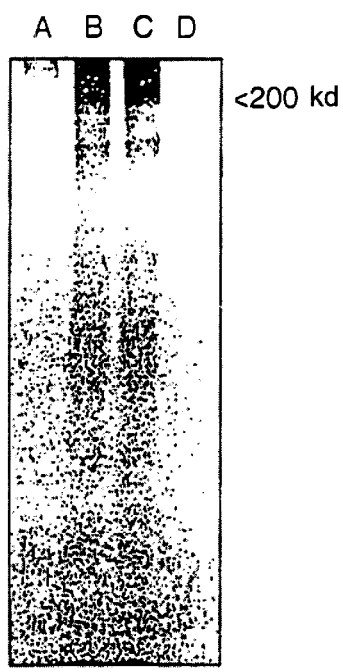

<200 kd

Autoradiograph of a 7.5% SDS polyacrylamide gel, showing the migration of labelled proteins compared to the sizes of known molecular weight markers (Amersham rainbow markers). Lane A control, Lane B SNS-B, Lane C SNS-B, Lane D control. The predicted 200kDa band representing the SNS-B sodium channel is arrowed.

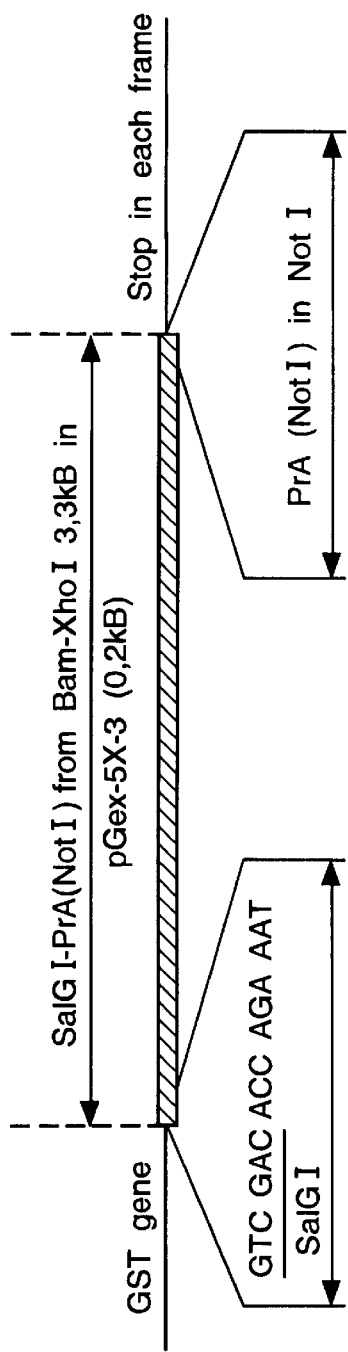
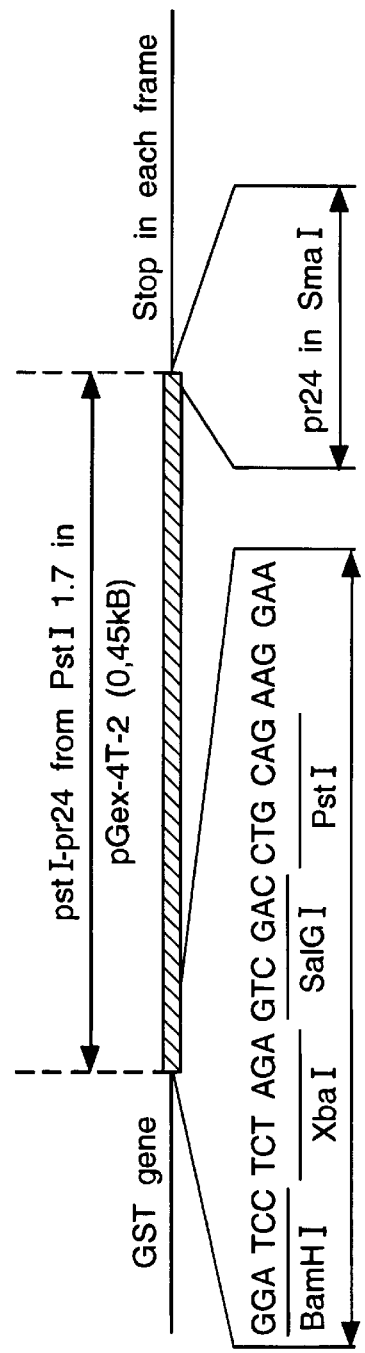
Fig.4b

ION CHANNEL

Voltage-gated sodium channels are transmembrane proteins which cause sodium permeability to increase. Depolarization of the plasma membrane causes sodium channels to open allowing sodium ions to enter along the electrochemical gradient creating an action potential.

Voltage-gated sodium channels are expressed by all electrically excitable cells, where they play an essential role in action potential propagation. They comprise a major subunit of about 2000 amino acids which is divided into four domains (D1–D4), each of which contains 6 membrane-spanning regions (S1–S6). The alpha-subunit is usually associated with 2 smaller subunits (beta-1 and beta-2) that influence the gating kinetics of the channel. These channels show remarkable ion selectivity, with little permeability to other monovalent or divalent cations. Patch-clamp studies have shown that depolarisation leads to activation with a typical conductance of about 20 pS, reflecting ion movement at the rate of $10^7$ ions/second/channel. The channel inactivates within milliseconds (Caterall, W. A., Physiol. Rev. 72, S4–S47 (1992); Omri et al, J. Membrane Biol 115, 13–29; Hille, B, Ionic Channels in Excitable Membranes, Sinauer, Sunderland, Mass. (1991)).

Sodium channels have been pharmacologically characterised using toxins which bind to distinct sites on sodium channels. The heterocyclic guanidine-based channel blockers tetrodotoxin (TTX) and saxitoxin (STX) bind to a site in the S5–S6 loop, whilst $\mu$-conotoxin binds to an adjacent overlapping region. A number of toxins from sea anemones or scorpions binding at other sites alter the voltage-dependence of activation or inactivation.

Voltage-gated sodium channels that are blocked by nanomolar concentrations of tetrodotoxin are known as tetrodotoxin sensitive sodium channels (Hille (1991) "Ionic Channels in Excitable Membranes", Sinauer Sunderland, Mass. (1991)) whilst sodium channels that are blocked by concentrations greater than 1 micromolar are known as tetrodotoxin-insensitive (TTXi) sodium channels (Pearce and Duchen Neuroscience 63, 1041–1056 (1994)).

Dorsal root ganglion (DRG) neurons express at least three types of sodium channels which differ in kinetics and sensitivity to TTX. Neurons with small-diameter cell bodies and unmyelinated axons (C-fibers) include most of the nociceptor (damage-sensing) population and express a fast TTX-sensitive current and a slower TTX-insensitive current. Of the five cloned sodium channel α-subunit transcripts known to be present in dorsal root ganglia, none exhibits the properties of the TTX-insensitive channel.

Sodium channel blockers are used clinically to provide pain relief. Three classes of sodium channel blockers in common clinical use are: local anesthetics such as lidocaine, some anticonvulsants such as phenytoin and carbamazepine, and some antiarrhythmics such as mexiletine. Each of these is known to suppress ectopic peripheral nervous system discharge in experimental preparations and to provide relief in a broad range of clinical neuropathic conditions.

Applicants have now found a novel voltage-gated sodium channel (hereinafter referred to as a sodium channel specifically located in sensory neurons or also referred to as SNS sodium channel) that is present in sensory neurons (or neurones) but not present in glia, muscle, or the neurons of the sympathetic, parasympathetic, enteric or central nervous systems. Preferably the sodium channel of the invention is found in the neurons of the dorsal root ganglia (DRG) or cranial ganglia. More preferably the sodium channel of the invention is found in the neurons of the dorsal root ganglia. Preferably the sodium channel is specifically located in rat sensory neurons or human sensory neurons.

The sodium channel of the present invention is believed to play a role in nociceptive transmission because some noxious input to the central nervous system is known to be insensitive to TTX. Persistent activation of peripheral nociceptors has been found to result in changes in excitability in the dorsal horn associated with the establishment of chronic pain. Increased sodium channel activity has also been shown to underlie neuroma-induced spontaneous action potential generation. Conversely, chronic pain may be successfully treated by surgical or pharmacological procedures which block peripheral nerve activation. Blockage of nociceptor input may therefore produce useful therapeutic effects, even though central nervous system plasticity plays a pivotal role in the establishment of chronic pain. Sensory neuron-specific voltage-gated sodium channels, particularly subtypes associated with a nociceptive modality such as the sodium channel of the invention, thus provide targets for therapeutic intervention in a range of pain states. The electrophysiological and pharmacological properties of the expressed SNS sodium channel are similar to those described for the small diameter sensory neuron tetrodotoxin-resistant sodium channels. As some noxious input into the spinal cord is resistant to tetrodotoxin, block of expression or function of such a C-fiber-restricted sodium channel may have a selective analgesic effect.

In another aspect the present invention provides an isolated protein comprising a sodium channel specifically located in rat sensory neurons as encoded by the insert deposited in NCIMB deposit number 40744, which was deposited at The National Collections of Industrial and Marine Bacteria, 23 St Machar Drive, Aberdeen AB2 1RY, Scotland, United Kingdom on Jun. 27, 1995 in accordance with the Budapest Treaty.

The invention also provides nucleotide sequences coding for the SNS sodium channel. In a preferred embodiment, the nucleotide sequence encodes a sodium channel specifically located in rat sensory neurons which is as set out in FIG. 1$a$ or a complementary strand thereof.

The approximately 6.5 kilobase (kb) transcript expressed selectively in rat dorsal root ganglia that codes for the novel sodium channel of the invention shows sequence similarities with known voltage-gated sodium channels. The cDNA codes for a 1,957 amino acid protein. In particular, the novel sodium channel of the invention shows 65% identity at the amino acid level with the rat cardiac tetrodotoxin-insensitive (TTXi) sodium channel. The aromatic residue that is involved in high-affinity binding of TTX to the channel atrium of TTX-sensitive sodium channels is altered to a hydrophilic serine in the predicted protein of the SNS sodium channel, whereas the residues implicated in sodium-selective permeability are conserved. The novel sodium channel specifically located in sensory neurons shows relative insensitivity to TTX (IC50>1 micromolar) and thus exhibits properties different from other cloned sodium channel transcripts known to be present in dorsal root ganglia.

The invention also provides expression and cloning vectors comprising a nucleotide sequence as hereinabove defined. In order to effect transformation, DNA sequences containing the desired coding sequence and control sequences in operable linkage (so that hosts transformed with these sequences are capable of producing the encoded proteins) may be included in a vector, however, the relevant DNA may then also be integrated into the host chromosome.

The invention also provides a screening assay for modulators of the sodium channel which is specifically located in sensory neurons wherein the assay comprises adding a potential modulator to a cell expressing the SNS sodium channel and detecting any change in activity of the sodium channel.

The present invention also provides a modulator which has activity in the screening assay hereinabove defined. Modulators of the sodium channel as hereinabove defined are useful in modulating the sensation of pain. Blockers of the sodium channel will block or prevent the trasmission of impulses along sensory neurons and thereby be useful in the treatment of acute, chronic or neuropathic pain.

The present invention thus relates to novel voltage-gated sodium channel proteins specific to sensory neurons, to nucleotide sequences capable of encoding these sodium channel proteins, to vectors comprising a nucleotide sequence coding for a sodium channel of the invention, to host cells containing these vectors, to cells transformed with a nucleic acid sequence coding for the sodium channel, to screening assays using the sodium channel proteins and/or host cells, to complementary stands of the DNA sequence which is capable of encoding the sodium channel proteins and to antibodies specific for the sodium channel proteins. These and other aspects of the present invention are set forth in the following detailed description.

BRIEF DESCRIPTION OF THE DRAWINGS

FIG. 1a shows the nucleic acid and amino acid sequences of the sodium channel specific to the rat DRG (SNS-B) (SEQ ID NO: 1 and SEQ ID NO: 2).

FIG. 1b shows the structure of the SNS-B voltage-gated sodium channel in pGEM-3Z.

FIG. 1c shows a schematised drawing of a known voltage-gated sodium channel.

FIG. 2 shows sequences of examples of PCR primers for isolation of human clone probes. RLLRVFKLAKSWPTL-SEQ ID NO: 21; 5' gcttgctgcgggtcttcaagc 3' SEQ ID NO: 22; LRALPLRALSRFEG-SEQ ID NO: 23; 5'atcgagacagagc-ccgcagcg3' SEQ ID NO: 24; 5' acgggtgccgcaaggacggcgtctc-cgtgtggaacggcgagaag 3' SEQ ID NO: 25; and 5' ggctatccttcctcttccagctctcacccaggtatggagccaggt3'-SEQ ID NO: 26.

FIG. 3 shows a film of $^{35}$S radio-labelled SNS-B voltage-gated sodium channel protein in a coupled transcription/translation system.

FIGS. 4a and 4b show SNS-GST fusion protein constructs for antibody generation. TCCCGTACGCTGCAGCTCTTT-SEQ ID NO: 27; CCCGGGGAAGGCTAC-SEQ ID NO: 28; GTCGACACCAGAAAT-SEQ ID NO: 29; GGATCCTCTAGAGTCGACCTGCAGAAGGAA-SEQ ID NO: 30

Figure 4A:
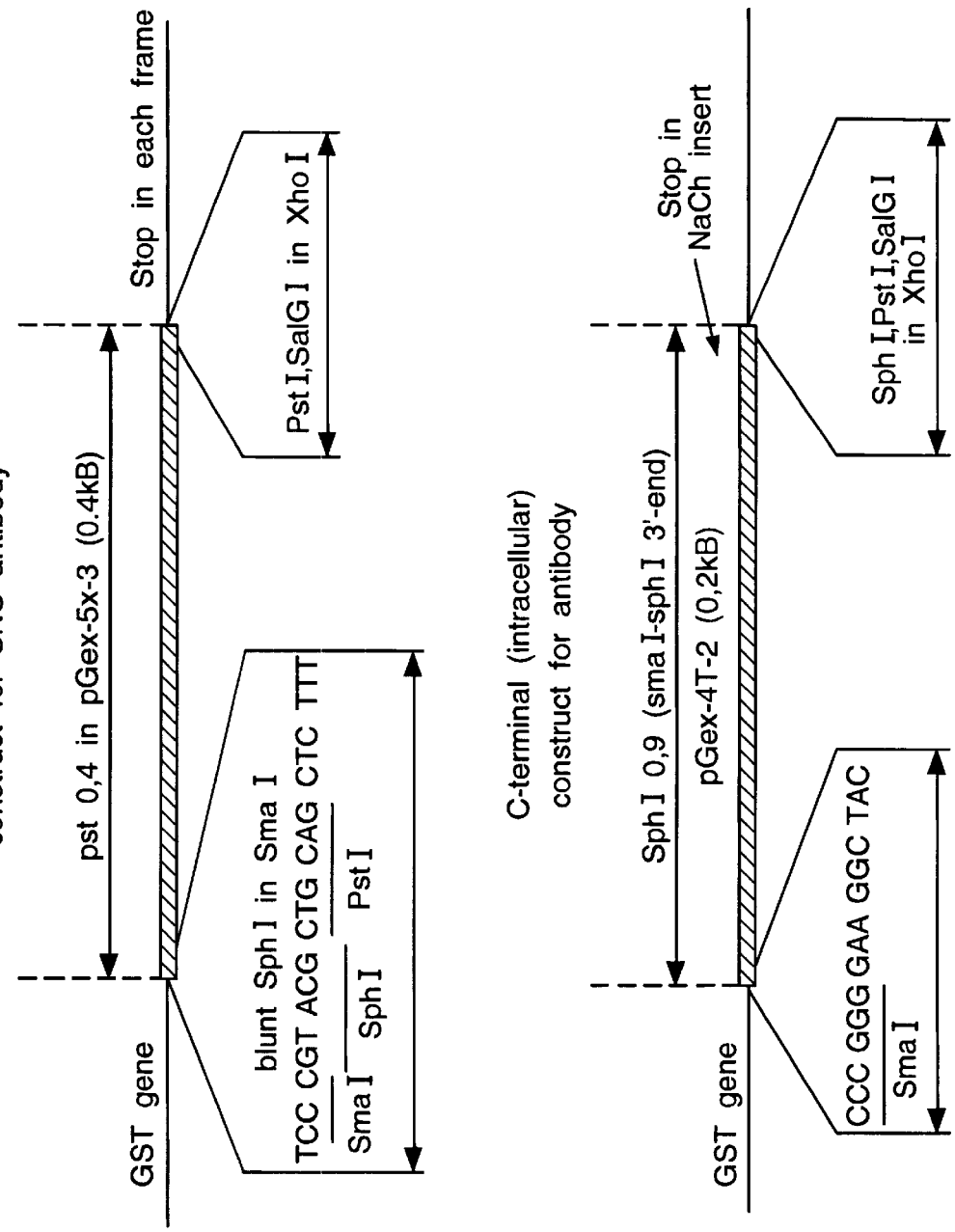

In accordance with one aspect of the invention there is provided an isolated and/or purified nucleic acid sequence (or polynucleotide or nucleotide sequence) which comprises a nucleic acid sequence which encodes the mammalian sodium channel specifically located in sensory neurons or a complementary strand thereof. Preferably, the nucleic acid sequence encodes the sodium channel specifically located in mammalian dorsal root ganglia. More preferably, the nucleic acid sequence encodes the rat or human sodium channel specifically located in dorsal root ganglia. The rat nucleic acid sequence preferably comprises the sequence of the coding portion of the nucleic acid sequence shown in FIG. 1a (SEQ ID NO:1) or the coding portion of the cDNA deposited in NCIMB deposit number 40744 which was deposited at the National Collections of Industrial and Marine Bacteria, 23 St. Machar Drive, Aberdeen AB21RY, Scotland, United Kingdom on Jun. 27, 1995 in accordance with the Budapest Treaty.

A nucleic acid sequence encoding a sodium channel of the present invention may be obtained from a cDNA library derived from mammalian sensory neurons, preferably dorsal root ganglia, trigeminal ganglia or other cranial ganglia, more preferably rat or human dorsal root ganglia. The nucleotide sequence described herein was isolated from a cDNA library derived from rat dorsal root ganglia cells. The nucleic acid sequence coding for the SNS sodium channel has an open reading frame of 5,871 nucleotides encoding a 1,957 amino acid protein. A nucleic acid sequence encoding a sodium channel of the present invention may also be obtained from a mammalian genomic library, preferably a human or rat genomic library. The nucleic acid sequence may be isolated by the subtraction hybridization method described in the examples, by screening with a probe derived from the rat sodium channel sequence, or by other methodologies known in the art such as polymerase chain reaction (PCR) with appropriate primers derived from the rat sodium channel sequence and/or relatively conserved regions of known voltage-gated sodium channels.

The nucleic acid sequences of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the rat SNS sodium channel or variant thereof may be identical to the coding sequences set forth herein or that of the deposited clone, or may be a different coding sequence which coding sequence, as a result of the redundancy or degeneracy of the genetic code, encodes the same protein as the sequences set forth herein or the deposited cDNA.

The nucleic acid sequence which encodes the SNS sodium channel may include: only the coding sequence for the full length protein or any variant thereof; the coding sequence for the full length protein or any variant thereof and additional coding sequence such as a leader or secretory sequence or a proprotein sequence; the coding sequence for the full length protein or any variant thereof (and optionally additional coding sequence) and non-coding sequences, such as introns or non-coding sequences 5' and/or 3' of the coding sequence for the full length protein.

The present invention further relates to variants of the hereinabove described nucleic acid sequences which encode fragments, analogs, derivatives or splice variants of the SNS sodium channel. The variant of the SNS sodium channel may be a naturally occurring allelic variant of the SNS sodium channel. As known in the art, an allelic variant is an alternate form of a protein sequence which may have a substitution, deletion or addition of one or more nucleotides, which does not substantially alter the function of the encoded protein. The present invention relates to splice variants of the SNS sodium channel that occur physiologically and which may play a role in changing the activation threshold of the sodium channel.

Variants of the sequence coding for the rat SNS sodium channel have been identified and are listed below:

1) a 2573 base pair nucleic acid sequence shown in SEQ ID NO:3. This sequence codes for a 521 amino acid protein that corresponds to amino acids 1437–1957 of FIG. 1a (SEQ ID NO:1) and has the same sequence as bases 4512 through 6524 of FIG. 1a in the coding portion and 3' untranslated region.

2) a 7052 base pair nucleic acid sequence shown in SEQ ID NO: 5. SEQ ID NO:5 codes for a 2,132 amino acid protein that contains a 176 amino acid repeat (amino acids 586–760 of SEQ ID NO:6) inserted after amino acid 585 in FIG. 1a or SEQ ID NO:2.

A preferred sequence for the rat SNS sodium channel is shown in FIG. 1a (SEQ ID NO: 1). However, sequencing variations have been noted. Sequencing has provided a 6,321 base pair nucleic acid sequence coding for a 1957 amino acid protein that has the same base sequence as bases 1–6321 of FIG. 1a or SEQ ID NO:1 with the following changes: bases 1092 G to A, base 1096 C to T, base 2986 G to T, base 3525 C to G and base 3556 G to C.

a 6,527 base pair nucleic acid sequence coding for a 1,957 amino acid protein as shown in SEQ ID NO:7 that has the same base sequence as bases 1–6524 of FIG. 1a (SEQ ID NO:1) with an additional 3 bases AAA, at the 3' end, and the following changes: base 299 C to G, base 1092 G to A, base 1096 C to T, base 1964 G to C, base 1965 C to G, base 2472 A to T, base 2986 G to T, base 3019 A to G, base 3158 C to T, base 3525 C to G, base 3556 G to C and base 5893 T to G. The sequence of SEQ ID NO: 7 is also a preferred sequence coding for the rat SNS sodium channel.

a 6524 base pair nucleic acid sequence that has the same sequence as FIG. 1a (SEQ ID NO: 1) except for the following base changes: base 1092 G to A (resulting in a change at amino acid 297 of SEQ ID NO: 2 from Val to Ile), base 1096 C to T (resulting in a change at amino acid 298 from Ser to Phe), base 1498 C to A (resulting in a change at amino acid 432 from Ala to Glu), and base 2986 G to T (resulting in a change at amino acid 928 form Ser to Ile).

Sequence variability has been identified in different isolates. One such seqeuence has been identified that has the sequence of the third sequencing variation shown immediately above except for eight base differences, five of which resulted in an altered amino acid sequence F16-S16, L393-P393, T470-1470, R278-H278, and I1,876-M1,876.

The present invention also relates to nucleic acid probes constructed from the nucleic acid sequences of the invention or portion thereof. Such probes could be utilized to screen a dorsal root ganglia cDNA library to isolate a nucleic acid sequence encoding the sodium channel of the present invention. The nucleic acid probes can include portions of the nucleic acid sequence of the SNS sodium channel or variant thereof useful for hybridizing with mRNA or DNA for use in assays to detect expression of the SNS sodium channel or localize its presence on a chromosome, such as the in situ hybridization assay described herein.

A conservative analogue is a protein sequence which retains substantially the same biological properties of the sodium channel but differs in sequences by one or more conservative amino acid substitutions. For the purposes of this document a conservative amino acid substitution is a substitution whose probability of occuring in nature is greater than ten times the probability of that substitution occuring by chance (as defined by the computational methods described byDayhoff et al, Atlas of Proteins Sequence and Structure, 1971, page 95–96 and FIGS. 9–10).

A splice variant is a protein product of the same gene, generated by alternative splicing of mRNA, that contains additions or deletions within the coding region (Lewin B. (1995) Genes V Oxford University Press, Oxford, England)

The nucleic acid sequences of the present invention may also have the coding sequence fused in frame to a marker sequence which allows for purification of the protein of the present invention such as a hexa-histidine tag or a hemagglutinin (HA) tag.

The present invention further relates to nucleic acid sequences which hybridize to the hereinabove-described sequences if there is at least 50% and preferably 70% identity between the sequences. The present invention particularly relates to nucleic acid sequences which hybridize under stringent conditions to the hereinabove-described nucleic acid sequences. As herein used, the term "stringent conditions" means hybridization will occur only if there is at least 95% and preferably at least 97% identity between the sequences preferably the nucleic acid sequences which hybridize to the hereinabove described nucleic acid sequences encode proteins which retain substantially the same biological function or activity as the SNS sodium channel, however, nucleic acid sequences that have different properties are also within the scope of the present invention. Such sequences, while hybridizing with the above described nucleic acid sequences may encode a protein having diffferent properties, such as sensitivity to tetrodotoxin which property is found in the altered SNS sodium channel protein described herein.

In accordance with another aspect of the invention there is provided purified mammalian sensory neuron sodium channel protein, wherein the sodium channel is insensitive to tetrodotoxin. Preferably the sodium channel of the invention is found in the neurons of the dorsal root ganglia or cranial ganglia, more preferably the neurons of the dorsal root ganglia. The sodium channel protein may be derived from any mammalian species, preferably the rat or human sodium channel protein. The rat SNS sodium channel protein preferably has the deduced amino acid sequence shown in FIG. 1a (SEQ ID NO:2) or SEQ ID NO: 8, or the amino acid sequence encoded by the deposited cDNA. Fragments, analogues, derivatives, and splice variants of the sodium channel specifically located in sensory neurons are also within the scope of the present invention.

The terms "fragment," "derivative" and "analogue" when referring to the DRG sodium channel of the invention refers to a protein which retains substantially the same biological function or activity as such protein. Thus, an analogue includes a proprotein which can be activated by cleavage of the proprotein portion to produce an active mature protein. In addition, the present invention also includes derivatives wherein the biological function or activity of the protein is significantly altered, including derivatives that are sensitive to tetrodotoxin.

The protein of the present invention may be a recombinant protein, a natural protein or a synthetic protein, preferably a recombinant protein.

The fragment, derivative or analog of the SNS sodium channel protein includes, but is not limited to, (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituted group, or (iii) one in which the mature polypeptide is fused with another compound, such as a compound to increase the half-life of the protein (for example, polyethylene glycol), or (iv) one in which the additional amino acids are fused to the mature protein, such as a leader or secretory sequence or a sequence which is employed for purification of the mature protein or a proprotein sequence, or (v) one in which one or more amino acids has/have been deleted so that the protein is shorter than the full length protein. Variants of the rat SNS sodium channel are discussed hereinabove and shown in SEQ ID NO:4 and SEQ ID NO:6.

The proteins and nucleic acid sequences of the present invention are preferably provided in an isolated form, and preferably are purified to at least 50% purity, more preferably about 75% purity, most preferably about 90% purity.

The terms "isolated" and/or "purified" mean that the material is removed from is original environment (e.g., the natural environment if it is naturally occurring). For example, a naturally-occurring nucleic acid sequence or protein present in a living animal is not isolated or purified, but the same nucleic acid sequence or DNA or protein, separated from some or all of the coexisting materials in the natural system, is isolated or purified. Such nucleic acid sequence could be part of a vector and/or such nucleic acid sequence or protein could be part of a composition, and still be isolated or purified in that such vector or composition is not part of its natural environment.

The present invention also provides vectors comprising a nucleic acid sequence of the present invention, and host cells transformed or transfected with a nucleic of the invention.

The nucleic acid sequences of the present invention may be employed for producing the SNS sodium channel protein or variant thereof by recombinant techniques. Thus, for example, the nucleic acid sequence may be included in any one of a variety of expression vehicles or cloning vehicles, in particular vectors or plasmids for expressing a protein. Such vectors include chromosomal, nonchromosomal and synthetic DNA sequences. Examples of suitable vectors include derivatives of SV40; bacterial plasmids; phage DNA; yeast plasmids; vectors derived from combinations of plasmids and phage DNA, viral DNA such as vaccinia, adenovirus, fowl pox virus, pseudorabies and baculovirus. However, any other plasmid or vector may be used as long as it is replicable and viable in the host.

More particularly, the present invention also provides recombinant constructs comprising one or more of the nucleic acid sequences as broadly described above. The constructs comprise an expression vector, such as a plasmid or viral vector, into which a sequence of the invention has been inserted, in a forward or reverse orientation. In a preferred aspect of this embodiment, the construct further comprises one or more regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen) pBs, phagescript, psiX174, pBluescript SK, pBsKS, pNH8a, pNH16a, pNH18a, pNH461 (Stratagene); pTrc99A, pKK223-3, pKK233-3, pDR540, pRIT5 (Pharmacia). Eukaryotic: pWLneo, pSV2cat, pOG44, pXT1, pSG (Stratagene), pSVK3, pBPV, pMSG, pSVL (Pharmacia) pcDNA 3.1 (Invitrogen, San Diego, Calif.), pEE14 (WO 87/04462) and pREP8 (Invitrogen). Preferred vectors include pcDNA 3.1, pEE14 and pREP8. However, any other plasmid or vector may be used as long as it is replicable and viable in the host.

As hereinabove indicated, the appropriate DNA sequence may be inserted into the vector by a variety of procedures. In general, the DNA sequence is inserted into appropriate restriction endonuclease sites by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter and other promoters known to control expression of genes in prokaryotic or eukaryotic cells or their viruses. The expression vector may contain a ribosome binding site for translation initiation and transcription terminator. The vector may also include appropriate sequences for amplifying expression.

Promoter regions can be selected from any desired gene using CAT (chloramphenicol transferase) vectors or other vectors with selectable markers. Two appropriate vectors are pKK232-8 and pCM7. Particular named bacterial promoters include LacI, LacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

Depending on the expression system employed in addition, the expression vectors preferably contain a gene to provide a phenotypic trait for selection of transformed host cells such as dihydrofolate reductase or neomycin resistance for eukaryotic cell culture, or such as tetracycline or ampicillin resistance in *E. coli*.

Transcription of DNA encoding the protein of the present invention by higher eukaryotes can be increased by inserting an enhancer sequence into the vector. Enhancers are cis-acting elements of DNA, usually about from 10 to 300 bp, that act on a promoter to increase its transcription. Examples include the SV40 enhancer on the late side of the replication origin (bp 100 to 270), a cytomegalovirus early promoter enhancer, a polyoma enhancer on the late side of the replication origin, and adenovirus enhancers.

Useful expression vectors for bacterial use may be constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera Pseydomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, PKK223-3 (Pharmacia Fine Chemicals, Uppsala, Sweden) and GEM1 (Promega Biotec, Madison, Wis., U.S.A.). These pBR322 "backbone" sections are combined with an appropriate promoter and the structural sequence to be expressed.

The sodium channel can be expressed in insect cells with the baculovirus expression system which uses baculovirus such as Autographa Californica nuclear polyhydrosis virus (AcNPV) to produce large amounts of protein in insect cells such as the Sf9 or 21 clonal lines derived from *Spodoptera frugiperda* cells. See for example O'Reilly et al., (1992) Baculovirus Expression Vectors: A Laboratory Manual, Oxford University Press.

Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 viral genome, for example, SV40 origin, early promoter, enhancer, splice, and polyadenylation sites may be used to provide the required nontranscribed genetic elements.

Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 viral genome, for example, SV40 origin, early promoter, enhancer, splice, and polyadenylation sites may be used to provide the required nontranscribed genetic elements.

In a further embodiment, the present invention provides host cells capable of expressing a nucleic acid sequence of the invention. The host cell can be, for example, a higher eukaryotic cell, such as a mammalian cell, a lower eukaryotic cell, such as a yeast cell, a prokaryotic cell, such as a bacterial cell. Introduction of the construct into the host cell may be effected by calcium phosphate transfection, DEAE-Dextran mediated transfection, electroporation (Davis, L., Dibner, M., Battey, I., Basic Methods in Molecular Biology, 1986) or any other method known in the art.

Host cells are genetically engineered (transduced, transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the SNS sodium channel genes. The culture conditions, such as temperature, pH and the like, are those previously used with the host cell selected for expression, and will be apparent to the ordinarily skilled artisan.

The vector containing the appropriate DNA sequence as hereinabove described, as well as an appropriate promoter or control sequence, may be employed to transform an appropriate host to permit the host to express the protein. As representative examples of appropriate hosts, there may be mentioned: bacterial cells, such as *E. coli,* and *Salmonella typhimurium;* Streptomyces; fungal cells, such as yeast; insect cells such as Drosophila and *Spodoptera fugiperda* Sf9; animal cells such as CHO, COS or Bowes melanoma Ltk⁻- and Y1 adrenal carcinoma; plant cells, etc. The selection of an appropriate host is deemed to be within the scope of those skilled in the art based on the teachings herein. Preferred host cells include mammalian cell lines such as CHO-K11, COS-7; Y1 adrenal; carcinoma cells. More preferably, the host cells are CHO-K1 cells. Preferred host cells for transient expression of the SNS sodium channel include *Xenopus laevis* oocytes.

The sodium channel may be transiently expressed in *Xeropus laevis* oocytes. Cell-free translation systems can also be employed to produce such proteins using RNAs derived from the DNA constructs of the present invention. Appropriate cloning and expression vectors for use with prokaryotic and eukaryotic hosts are described in Sambrook et al., Molecular Cloning: A Laboratory Manual, Second Edition, Cold Spring Harbor, N.Y., (1989).

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C 127, 3T3, CHO, CHO-K1, HeLa, HEK 293, NIH 3T3 and BHK cell lines.

The constructs in host cells can be used in a conventional manner to produce the gene product encoded by the recombinant sequence. Alternatively, the proteins of the invention can be synthetically produced by conventional peptide synthesizers.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well-known to those skilled in the art.

The SNS sodium channel protein is recovered and purified from recombinant cell cultures by methods known in the art, including ammonium sulfate or ethanol precipitation, acid extraction, anion or cation exchange chromatography, phosphocellulose chromatography, hydrophobic interaction chromatography, hydroxyapatite chromatography and lectin chromatography. Protein refolding steps may be used, as necessary, in completing configuration of the mature protein. Finally, high performance liquid chromatography (HPLC) can be employed for final purification steps.

The SNS sodium channel protein of the present invention may be naturally purified products expressed from a high expressing cell line, or a product of chemical synthetic procedures, or produced by recombinant techniques from a prokaryotic or eukaryotic host (for example, by bacterial, yeast, higher plant, insect and mammalian cells in culture).

The present invention also provides antibodies specific for the SNS sodium channel hereinabove defined. The term antibody as used herein includes all immunoglobulins and fragments thereof which contain recognition sites for antigenic determinants of proteins of the present invention. The antibodies of the present invention may be polyclonal or preferably monoclonal, may be intact antibody molecules or fragments containing the active binding region of the antibody, e.g. Fab or $F(ab)_2$ and can be produced using techniques well established in the art [see e.g. R. A DeWeger et al; Immunological Rev., 62 p29–45 (1982)].

The proteins, their fragments or other derivatives, or analogs thereof, or cells expressing them can be used as an immunogen to produce antibodies thereto. These antibodies can be, for example, polyclonal or monoclonal antibodies. The present also includes chimeric, single chain and humanized antibodies, as well as Fab fragments, or the product of an Fab expression library. Various procedures known in the art may be used for the production of such antibodies and fragments.

Antibodies generated against the SNS sodium channel can be obtained by direct injection of the polypeptide into an animal or by administering the protein to an animal, preferably a nonhuman. The antibody so obtained will then bind the protein itself. In this manner, even a sequence encoding only a fragment of the protein can be used to generate antibodies binding the whole native protein. Such antibodies can then be used to locate the protein in tissue expressing that polypeptide. For preparation of monoclonal antibodies, any technique which provides antibodies produced by continuous cell line cultures can be used. Examples include the hybridoma technique (Kohler and Milstein, 1975, Nature 256:495–497), the trioma technique, the human B-cell hybridoma technique (Kozbor et al., 1983, Immunology Today 4:72), and the EBV-hybridoma technique to produce human monoclonal antibodies (Cole, 35 al., 1985, in Monoclonal Antibodies and Cancer Therapy, Alan R. Liss., pp. 77–96).

Techniques described for the production of single chain antibodies (U.S. Pat. No. 4,946,778) can be adapted to produce single chain antibodies to immunogenic polypeptide products of this invention.

The antibodies of the present invention may also be of interest in purifying a protein of the present invention and accordingly there is provided a method of purifying a protein of the present invention as hereinabove defined or any portion thereof or a metabolite or degration product thereof which method comprises the use of an antibody of the present invention.

The purification method of the present invention may be effected by any convenient technique known in the art for example by providing the antibody on a support and contacting the antibody with a solution containing the protein whereby the antibody binds to the protein of the present invention. The protein may be released from binding with the antibody by known methods for example by changing the ionic strength of the solution in contact with the complex of the protein/antibody.

The present invention also provides methods of identifying modulators of the sodium channel which is specifically located in sensory neurons comprising contacting a test compound with the sodium channel and detecting the activity of the sodium channel. Preferably, the methods of identifying modulators or screening assays employ transformed host cells that express the sodium channel. Typically, such assays will detect changes in the activity of the sodium channel due to the test compound, thus identifying modulators of the sodium channel. Modulators of the sodium channel are useful in modulating the sensation of pain. Blockers of the sodium channel will prevent the transmission of impulses along sensory neurons and thereby be useful in the treatment of acute, chronic or neuropathic pain.

The sodium channel can be used in a patch clamp or other type of assay, such as the assays disclosed herein in the examples, to identify small molecules, antibodies, peptides, proteins, or other types of compounds that inhibit, block, or otherwise interact with the sodium channel. Such modulators identified by the screening assays can then be used for treatment of pain in mammals.

For example, host cells expressing the SNS sodium channel can be employed in ion flux assays such as $^{22}$Na+ ion flux and $^{14}$C guanidinium ion assays, as described in the examples and in the art, as well as the SFBI fluorescent sodium indicator assays as described in Levi et al., (1994) J. Cardiovascular Electrophysiology 5:241–257. Host cells expressing the SNS sodium channel can also be employed in binding assays such as the 3H-batrachotoxin binding assay described in Sheldon et al., (1986) Molecular Pharmacology 30:617–623; the 3H-saxitoxin assay as described in Rogart et al (1983) Proc. Natl. Acad. Sci. USA 80:1106–1110; and the scorpion toxin assay described in West et al., (1992) Neuron 8:59–70. Additionally, the host cells expressing the SNS sodium channel can be used in electrophysiological assays using patch clamp or two electrode techniques. In general, a test compound is added to the assay and its effect on sodium flux is determined or the test compound's ability to competitively bind to the sodium channel is assessed. Test compounds having the desired effect on the SNS sodium channel are then selected. Modulators so selected can then be used for treating pain as described above.

Complementary strands of the nucleotide sequences as hereinabove defined can be used in gene therapy, such as disclosed in U.S. Pat. No. 5,399,346. For example, the cDNA sequence or fragments thereof could be used in gene therapy strategies to down regulate the sodium channel. Antisense technology can be used to control gene expression through triple-helix formation or antisense DNA or RNA, both of which methods are based on binding of a nucleic acid sequence to DNA or RNA. For example, the 5' coding portion of the nucleic acid sequence that encodes the sodium channel is used to design an antisense RNA oligonucleotide of from about 10 to about 40 base pairs in length. A DNA oligonucleotide is designed to be complimentary to a region of the gene involved in transcription (triple helix-see Lee et al., Nucl. Acids Res. 6:3073 (1979); Cooney et al, Science 241:456 (1988); and Deruau et al., Science 251:1360 (1991)), thereby preventing transcription and the product of the sodium channel. The antisense RNA oligonucleotide hybridizes to the mRNA in vivo and blocks translation of the mRNA into the sodium channel. Antisense oligonucleotides or an antisense construct driven by a strong constituitive promoter expressed in the target sensory neurons would be delivered either peripherally or to the spinal cord.

The regulatory regions controlling expression of the sodium channel gene could be used in gene therapy to control expression of a therapeutic construct in cells expressing the sodium channel.

Such regions would be isolated by using the cDNA as a probe to identify genomic clones carrying the gene and also flanking sequence e.g. cosmids. Fragments of the cosmids containing intron or flanking sequence would be used in a reporter gene assay in e.g. DRG cultures or transgenic animals and genomic fragments carrying e.g. promoter, enhancer or LCR activity identified.

The invention will now be further described with reference to the following examples:

EXAMPLE 1

Derivation of the Sequence of a Rat Dorsal Root Ganglia (DRG) Sodium Channel cDNA by Subtraction Hybridisation Methodology 1.1 cDNA Synthesis from DRG-derived poly-A+ RNA Dorsal root ganglia (DRG) from all spinal levels of neonatal Sprague-Dawley male and female rats were frozen in liquid nitrogen. RNA is extracted using guanidine isothiocyanate and phenol/chloroform extraction (Chomczynski and Sacchi 1987 Anal Biochem 162, 156–159).

Total RNA isolation—the nerve tissue is homogenised using a Polytron homogeniser in 1 ml extraction buffer (23.6 g guanidinium isothiocyanate, 5 ml of 250 mM sodium citrate (pH 7.0) made up to 50 ml with distilled water. To this is added 2.5 ml 10% sarcosyl and 0.36 ml β-mercaptoethanol). 0.1 ml of 2M sodium acetate (pH 4.0) is added followed by 1 ml phenol. After mixing, 0.2 ml chloroform is added and this is shaken vigorously and placed on ice for 5 minutes. This is then centrifuged at 12,000 revolutions per minute (rpm) for 30 minutes at 4° C. The aqueous phase is transferred to a fresh tube, 1 ml of isopropanol is added and this is left at −20° C. for an hour followed by centrifuging at 12000 rpm for 30 minutes at 4° C. The pellet is dissolved in 0.1 ml extraction buffer and is again extracted with isopropanol. The resulting pellet is washed with 70% ethanol and is resuspended in diethyl pyrocarbonate (DEPC)-treated water. 0.3M sodium acetate (pH5.2) and 2 volumes of ethanol are added and the mixture is placed at −20° C. for 1 hour. The RNA is precipitated, washed again with 70% ethanol and resuspended in DEPC-treated water. The optical density is measured at 260 nanometres (nm) to calculate the yield of total RNA. Poly A+ RNA is isolated from the total RNA by oligo-dT cellulose chromatography (Aviv and Leder 1972 Proc Natl Acad Sci 69,1408–1411). The following procedures are carried out at 4° C. as far as is possible. Oligo-dT cellulose (Sigma) is prepared by treatment with 0.1M sodium hydroxide for 5 minutes. The oligo-dT resin is poured into a column and is neutralised by washing with neutralising buffer (0.5 M potassium chloride, 0.01M Tris (Trizma base—Sigma-Tris (hydroxymethyl)aminomethane) (pH 7.5). The RNA solution is adjusted to 0.5M potassium chloride, 0.01M Tris (pH7.5) and is applied to the top of the column. The first column eluate is re-applied to the column to ensure sticking of the mRNA to the oligo-dT in the column. The column is then washed with 70 ml of neutralising buffer and the polyA+ RNA is eluted with 6 ml 0.01M Tris (pH7.5) and 1 ml fractions are collected. The poly A+ RNA is usually in fractions 2 to 5 and this is checked by measuring the optical density at 260 nm. These fractions are pooled and ethanol precipitated overnight at −70° C., washed in 70% ethanol and then redissolved in deionised water at a concentration of 1 mg/ml.

First strand CDNA was generated using 0.5 mg DRG poly A+ mRNA, ligo-dT/Not-I primer adapters and SuperScript reverse transcriptase (Gibco-BRL) using methodology as described in example 2. One half of the cDNA was labelled by including 2 MBq $^{32}$P dCTP (Amersham) in the reverse transcriptase reaction. Labelled cDNA is separated from unincorporated nucleotides on Nick columns (Sephadex G50-Pharmacia).

1.2 Enrichment of DRG-specific cDNA Using Subtraction Hybridisation

Poly A+ RNA from various tissues (10 µg) is incubated with 10 µg photoactivatable biotin (Clontech) in a total volume of 15 µl and irradiated at 4° C. for 30 minutes with a 250 watt sunlamp. The photobiotin is removed by extraction with butanol, and the cDNA co-precipitated with the biotinylated RNA without carrier RNA (Sive and St. John 1988 Nuc Ac Res 16,10937).

Hybridisation is carried out at 58° C. for 40 hours in 20% formamide, 50 mM 3-(N-morpholino)propanesulphonic acid (MOPS) (pH 7.6), 0.2% sodium dodecyl sulphate (SDS), 0.5M sodium chloride, 5 mM ethylenediaminetet-raacetate (EDTA—Sigma). The total reaction volume is 5 µl and the reaction is carried out under mineral oil, after an initial denaturation step of 2 minutes at 95° C. 100 µl 50 mM MOPS (pH 7.4), 0.5M sodium chloride, 5 mM EDTA containing 20 units of streptavidin (BRL) is then added to the reaction mixture at room temperature, and the aqueous phase retained after two phenol/chloroform extraction steps. After sequential hybridisation of the cDNA from Example 1.1 with biotinylated mRNA from liver and kidney, followed by cortex and cerebellum, a 80-fold concentration of DRG-specific transcripts is achieved.

One third of the 1–2 ng of residual cDNA is then G-tailed with terminal deoxynucleotide transferase at 37° C. for 30 minutes. The polymerase chain reaction is used to amplify the cDNA using an oligo-dT-Not-I primer adapter and oligo-dC primers starting with the sequence AATTCCGA (C)$_{10}$. Amplification is carried out using 2 cycles of 95° C. for 1 min, 45° C. for 1 min, 72° C. for 5 min, followed by 2 cycles of 95° C. for 1 minute, 58° C. for 1 minute and 72° C. for 5 minutes. The resulting products are then separated on a 2% Nu-sieve agarose gel, and material running at a size of greater than 0.5 kilobase pairs (kb) is eluted and further amplified with 6 cycles of 95° C. for 1 minute, 58° C. for 1 minute and 72° C. for 5 minutes. This material is further separated on a 2% Nu-sieve agarose gel, and the material running from 6 kb on the gel is eluted and further amplified using the same PCR conditions for 27 cycles. The amplified DNA derived from this high molecular weight region is then further fractionated on a 2% Nu-Sieve gel, and cDNA from 0.5 to 1.5 kb, and from 1.5 to 5 kb pooled.

1.3. Library Construction

10 µg of the bacteriophage vector lambda-zap II (Stratagene) is restriction digested with NotI and EcoRI in high salt buffer overnight at 37° C. followed by dephosphorylation using 1 unit of calf intestinal phosphatase (Promega) for 30 minutes at 37° C. in 10 mM Tris.HCl (pH9.5), 1 mM spermidine, 0.1 mM EDTA. DRG cDNA is digested with Klenow enzyme in the presence of dGTP and dCTP to construct an EcoRI site from the oligo-dC primer (see above) at the 5' end of the cDNA, and cut with NotI for directional cloning. The cDNA is ligated into the cloning vector bacteriophage lambda-zap II for 16 hours at 12° C. Recombinant phage DNA is then packaged into infective phage using Gigapack gold (Stratagene) and protocols specified by the suppliers. 0.1% of the packaged DNA is used to infect E.coli BB4 cells which are plated out to calculate the number of independent clones generated.

1.4 Differential Screening

The library is plated at a low density (10$^3$ clones/12×12 cm$^2$ dish) and screened using three sets of $^{32}$P-labelled cDNA probes and multiple filter lifts. Replica filters are made by laying them onto the plated library plates, briefly drying them and then laying onto fresh agar plates to increase the quantity of phage and the subsequent hybridisation signals of lifts taken from them. The probes are derived from: a) cortex and cerebellum poly (A)+ RNA, b) DRG poly (A)+ RNA, and c) subtracted cDNA from DRG. The two mRNA probes are labelled with $^{32}$P dCTP using a reaction mixture containing 2–5 µg RNA, 50 µl 5×RT buffer, 25 µl 0.1M dithiothreitol (DTT), 12.5 µl 10 mM dATP, dGTP, dCTP, 30 pM oligo-dT, 75 µl $^{32}$P-dCTP (30 MBq; Amersham), 25 µl 100 µM dCTP, 2 µl RNasin (2 units/µl) and 2 µl SuperScript reverse transcriptase (GibcoBRL) in a final volume of 250 µl. The reaction is incubated at 39° C. for 60 minutes, and the RNA subsequently destroyed by adding 250 µl water, 55 µl 1M NaOH, and incubating at 70° C. for 20 minutes. The reaction mixture is neutralised with acidified Tris base (pH 2.0) and precipitated with carrier tRNA (Boehringer) with isopropanol. The subtracted and amplified double-stranded DRG cDNA is random-prime labelled with $^{32}$P dATP (Gibco multiprime kit). Replica filters are then prehybridised for 4 hours at 68° C. in hybridisation buffer. Hybridisation was carried out for 20 hours at 68° C. in 4×SSC (20×SSC consists of 175.3 g of sodium chloride and 88.2 g of sodium citrate in 800 ml of distilled water. The pH is adjusted to 7.0 with 10N sodium hydroxide and this is made to 1 liter with distilled water), 5×Denhardts solution containing 150 µg/ml salmon sperm DNA, 20 µg/ml poly-U, 20 µg/ml poly-C, 0.5% SDS (Sigma), 5 mM EDTA. The filters are briefly washed in 2×SSC at room temperature, then twice with 2×SSC with 0.5% SDS at 68° C. for 15 minutes, followed by a 20 minute wash in 0.5% SDS, 0.2×SSC at 68° C. The filters are autoradiographed for up to I week on Kodak X-omat film. Plaques that hybridise with DRG probes but not cortex and cerebellum probes are picked, phage DNA prepared and the cloned inserts released for subcloning into pBluescript (Stratagene).

The positive plaques are picked by lining up the autoradiogram with the plate using orientation marks and taking a plug from the plate corresponding to the positive hybridisation signal. The phage is eluted from the plug in 0.5 ml phage dilution buffer (10 mM Tris chloride (pH7.5) 10 mM magnesium sulphate) and the phage re-infected into E.coli BB4 and replated at a density of 200 to 1000 plaques/150 mm plate as a secondary purification step to ensure purity of the clones. The positive secondaries are then picked as described previously. In order to sub-clone the insert DNA from the positive recombinant phage, they need to be amplified. This is accomplished by plate lysis where the phage totally lyse the E.coli BB4. 0.2 ml of phage suspension is mixed with 0.1 ml of an overnight culture of E.coli. This is added to 2.5 ml of top agar (16 g bacto-tryptone 10 g bacto-yeast extract, 5 g sodium chloride, 7 g bacto-agar in 900 mls distilled water) and plated onto 9 cm² agar plates. These are incubated overnight at 37° C. 5 ml of phage dilution buffer is then added to the plates and is incubated overnight at 4° C. or for 4 hours with gentle scraping at room temperature. The phage-containing buffer is then recovered, 0.1 ml chloroform is added and this phage stock is titrated as above and stored at 4° C. Phage DNA is prepared by first infecting $10^{10}$ *E.coli* B44 with $10^9$ plaque forming units (pfus) of phage in 3 ml of phage dilution buffer and shaking at 37° C. for 20 minutes. The infected bacteria are added to 400 ml of L broth (1.6% bactotryptone, 0.5% (w/v) Bacto yeast extract, 0.5% (w/v) magnesium sulphate) with vigorous shaking at 37° C. for 9 hours. When lysis has occurred, 10 ml of chloroform is added and shaking is continued for a further 30 minutes. The culture is then cooled to room temperature and pancreatic RNAase and DNAase are added to 1 ug/ml for 40 minutes. Sodium chloride is then added to 1M and is dissolved by swirling on ice. After centrifuging at 8000 rpm for 10 minutes the supernatant is recovered. Polyethylene glycol (PEG 6000) is added to 10% w/v and is dissolved by stirring whilst on ice for 2 hours. After centrifuging for 8000 rpm for 10 minutes at 4° C. the pellet is resuspended in 8 ml of phage dilution buffer. This is extracted with an equal volume of phenol/chloroform followed by purification on a caesium chloride gradient (0.675 g/ml caesium chloride—24 hours at 38000 rpm at 4° C.). The opaque phage band is removed from the centrifugation tube and dialysed against 10 mM sodium chloride, 50 mM Tris (pH8.0), 10 mM magnesium chloride for 2 hours. EDTA is then added to 20 mM, proteinase K to 50 µg/ml and SDS to 0.5% and is incubated at 65° C. for 1 hour. After dialysis overnight against TE pure phage DNA results. The cloned insert is digested from the purified phage DNA using restriction enzymes as previously described. Each phage insert is then ligated into a plasmid vector e.g. pBluescript—Clontech using a ligation reaction as previously described.

Clone Characterisation

The plasmids are cross hybridised with each other. Unique clones are further analysed by Northern blotting and sequencing. The clone/s showing transcript sizes and sequence comparable with sodium channels are then used as hybridisation probes to screen a neonatal rat DRG oligo dT-primed full length cDNA library to derive full length cDNA clones using methodology as described above and in example 2. Biological activity of the rat DRG sodium channel is confirmed as in examples 4 and 7 below.

EXAMPLE 2

Homology Cloning of the Human cDNA Homologous to the Rat DRG Sodium Channel cDNA (SNS-B)

2.1. Isolation of Human Ganglia Total RNA

The starting material for the derivation of the human cDNA homologue of the rat DRG sodium channel cDNA is isolated human dorsal root ganglia or trigeminal ganglia or other cranial ganglia from post-mortem human material or foetuses. Total ribonucleic acid (RNA) is isolated from the human neural tissue by extraction in guanidinium isothiocyanate (Chomczynski and Sacchi 1987 Anal Biochem 162,156–159) as described in example 1.

2.2 Determination of the Transcript Size of the Human Homologue of the Rat DRG Sodium Channel cDNA (SNS-B)

Human dorsal root ganglia total RNA is electrophoretically separated in a 1% (w/v) agarose gel containing a suitable denaturing agent e.g. formaldehyde (Lehrach et al 1977 Biochemistry 16,4743; Goldberg 1980 Proc Natl Acad Sci 77,5794; Seed 1982 in Genetic engineering: principles and methods (ed J K Setlow and A Hollaender) vol 4 p91 Plenum Publishing New York) or glyoxal/DMSO (McMaster G K and Carmichael G G 1977 Proc Natl Acad Sci 74,4835), followed by transfer of the RNA to a suitable membrane (e.g. nitrocellulose). The immobilised RNA is then hybridised to radioactive (or other suitable detection label) probes consisting of portions of the rat sodium channel cDNA sequence (see below). After washing of the membrane to remove non-hybridised probe, the hybridised probe is visualised using a suitable detection system (e.g. autoradiography for $^{32}$P labelled probes) thus revealing the size of the human homologous mRNA molecule. Specifically, 20–30 µg total RNA from neonatal rat tissues are separated on 1.2% agarose-formaldehyde gels, and capillary blotted onto Hybond-N (Amersham) (Ninkina et al. 1993 Nuc Ac Res 21,3175–3182). The amounts of RNA on the blot are roughly equivalent, as judged by ethidium bromide staining of ribosomal RNA or by hybridisation with the ubiquitously expressed L-27 ribosomal protein transcripts (Le Beau et al. 1991 Nuc Ac Res 19,1337). Each Northern blot contains human DRG, cortex, cerebellum, liver kidney, spleen and heart RNA. Probes (50 ng) are labelled with $^{32}$P-dATP (Amersham) by random priming. Filters are prehybridised in 50% formaldehyde 5×SSC containing 0.5% SDS, 5×Denhardts solution (50×Denhardts contains 5 g of Ficoll (Type 400, Pharmacia), 5 g of polyvinylpyrrolidone, 5 g of bovine serum albumin (Fraction V, Sigma) and water to 500 ml), 100 µg/ml boiled salmon sperm DNA, 10 µg/ml poly-U and 10 µg/ml poly-C at 45° C. for 6 hours. After 36 hours hybridisation in the same conditions, the filters are briefly washed in 2×SSC at room temperature, then twice with 2×SSC with 0.5% SDS at 68° C. for 15 minutes, followed by a 20 minute wash in 0.5% SDS, 0.2×SSC at 68° C. The filters are autoradiographed for up to 1 week on Kodak X-omat film. The transcript size is calculated from the signal from the gel in comparison with gel molecular weight standard markers.

2.3 Production of a Human DRG cDNA Library

In order to produce a representative cDNA library from the human dorsal root ganglia messenger RNA (poly A+ mRNA) is first isolated from the total RNA pool using oligo-dT cellulose chromatography (Aviv and Leder 1972 Proc Natl Acad Sci 69,1408–1411) using methodology described in example 1. Synthesis of the first strand of cDNA from the polyA+ RNA uses the enzyme RNA-dependent DNA polymerase (reverse transcriptase) to catalyse the reaction. The most commonly used method of second strand cDNA synthesis uses the product of first strand synthesis, a cDNA:mRNA hybrid, as a template for priming the second strand synthesis. (Gubler and Hoffman 1983 Gene 25,263)).

2.3.1. First Strand cDNA Synthesis

20 µg of human DRG polyA+ RNA is pre-treated to destroy secondary structure which may inhibit first strand cDNA synthesis. 20 µg of polyA+ RNA, 1 µl 1M Tris (pH7.5) are made up to a volume of 100 µl with distilled water. This is incubated at 90° C. for 2 minutes followed by cooling on ice. 4.8 µl of 100 mM methyl mercury is then added for 10 minutes at room temperature. 10 µl of 0.7M β-mercaptoethanol and 100 units of human placental RNAase inhibitor are then added for 5 minutes at room temperature. The first strand synthesis reaction consists of 8 µl 20 mM dATP, 5 µl 20 mM dCTP, 8 µl 20 mM dGTP 8 µl 20 mM dTTP, 10 µl 1 mg/ml oligo-dT (12–18), 20 µl 1M Tris (pH 8.3) (at 45° C.), 8 µl 3M potassium chloride, 3.3 µl 0.5M magnesium chloride, 3 µl a$^{32}$P dCTP, 100 units Superscript II reverse transcriptase (GibcoBRL) made up to 200 µl with distilled water. This reaction mixture is incubated at 45° C.

for 45 minutes after which another 50 units of Superscript reverse transcriptase is added and incubated for a further 30 minutes at 45° C. EDTA is then added to 10 mM to terminate the reaction and a phenol/chloroform extraction is carried out. The DNA is then precipitated using ammonium acetate (freezing in dry ice/ethanol before centrifuging), washed with 70% ethanol and resuspended in 50 ml distilled water. The size of the single stranded DNA is assessed by electrophoretically separating it out on an agarose gel (1% w/v) and autoradiographing the result against markers.

2.3.2 Second Strand Synthesis

The second strand synthesis reaction mixture consists of 0.5 μg human DRG single stranded DNA, 2 μl 1M Tris (pH7.5), 1 μl 0.5M magnesium chloride, 3.33 μl 3M potassium chloride, 2 μl 0.5M ammonium sulphate, 1.5 μl 10 mM βnicotinamide adenine dinucleotide (NAD), 4 μl of each of the 1 mM dNTPs, 5 μl 1 mg/ml bovine serum albumin (BSA), 1 unit RNAase-H, 25 units Klenow polymerase all made up to 100 μl with distilled water. This is incubated at 12° C. for 1 hour and then at 20° C. for 1 hour. The reaction is stopped by addition of EDTA to 20 mM followed by a phenol/chloroform extraction. The DNA is ethanol precipitated (−70° C. overnight) and is then washed with 70% ethanol followed by resuspension in 20 μl distilled water. Size is checked by gel electrophoresis and autoradiography.

2.3.3 Double Stranded cDNA end Repair

In order to add linkers to the end of the cDNA molecules for subsequent cloning, the ends must first be repaired. The human DRG cDNA is treated with 500 units/ml of S1 nuclease in 0.25M sodium chloride, 1 mM zinc sulphate, 50 mM sodium acetate (pH4.5). Incubation is at 30° C. for 40 minutes followed by neutralisation with Tris (pH 8.0) to 0.2M. The DNA is again ethanol precipitated, washed in 70% ethanol and resuspended in 20 μl distilled water. The size is again checked to ensure that S1 nuclease digestion has not radically reduced the average DNA fragment size. The repair reaction consists of 19 μl cDNA, 3 μl 10×T4 polymerase buffer (0.33M Tris acetate (pH7.9), 0.66M potassium acetate, 0.1M magnesium acetate, 1 mg/ml BSA and 5 mM DTT), 2 μl of each dNTP at 2 mM, 2 μl T4 polymerase and 4 μl distilled water. This is incubated at 37° C. for 30 minutes followed by addition of 1 μl Klenow polymerase for 1 hour at room temperature. The DNA is then ethanol precipitated, washed in 70% ethanol and resuspended in 5 μl distilled water. In order to protect naturally occurring restriction sites within the cDNA from being cleaved, the cDNA is treated with a methylase before the addition of linkers. The reaction mixture consists of 5 μl human DRG double stranded DNA, 1 μl S-adenosylmethionine, 2 μl 1 mg/ml BSA, 2 μl 5×methylase buffer (0.5M Tris (pH8.0), 5 mM EDTA), 0.2 μl EcoRI methylase (NEB). This is incubated at 37° C. for 20 minutes followed by phenol extraction, ethanol precipitation washing with 70% ethanol and resuspension in 20 μl distilled water.

2.3.4. Addition of Linkers to cDNA

EcoRI linkers are ligated to the cDNA molecules to facilitate cloning into lambda vectors. The ligation reaction mixture consists of 1 μl 10× ligation buffer (0.5M Tris chloride (pH7.5), 0.1M magnesium chloride and 0.05M DTT), 1 μl 10 mM ATP, 100 ng cDNA, 5 μg EcoRI linkers, 1 unit T4 DNA ligase, distilled water to 10 μl. The reaction is incubated at 37° C. for 1 hour, followed by addition of 6 more units of T4 ligase and a further incubation overnight at 15° C. The ligated samples are ethanol precipitated, washed in 70% ethanol and resuspended in 10 μl distilled water. The cDNA is then digested with EcoRI to cleave any linker concatamers formed in the ligation process. This restriction digestion reaction contains 10 μl cDNA, 2 μl high salt buffer (10 mM magnesium chloride, 50 mM Tris chloride (pH7.5), 1 mM DTT, 100 mM sodium chloride), 2 μl EcoRI (10 units/μl—NEB) and distilled water to 20 μl. The digestion is carried out for 3 hours. The ligation and digestion steps are monitored using gel elecrophoresis to monitor the size of the products.

2.3.5 Size Fractionation of cDNA

In order to assure that the library is not swamped with short cDNA molecules and to remove linker molecules a column purification is carried out. A 1 ml Sepharose 4B column is made in a 1 ml plastic pipette plugged with a small piece of glass wool. This is equilibrated with 0.1M sodium chloride in TE. The cDNA is loaded onto the column and 1 drop fractions are collected. 2 μl aliquots of each fraction are analysed by gel electrophoresis and autoradiography to determine the sizes of the cDNA in each fraction. Fractions containing cDNA of about 800 base pairs and above are pooled and purified by ethanol precipitation and resuspending in 10 μl distilled water.

2.3.6 Cloning of cDNA into Bacteriophage Vector

Bacteriophage vectors designed for the cloning and propagation of cDNA are provided ready-digested with EcoRI and with phosphatased ends from commercial sources (e.g. lambda gt10 from Stratagene). The prepared subtracted cDNA is ligated into lambda gt10 using a ligation rection consisting of ligase buffer and T4 DNA ligase (New England Biolabs) as described elsewhere in this document.

2.4 Labelling of cDNA Fragments (Probes) for Library Screening

The 3' untranslated region of the rat DRG sodium channel cDNA clone (SNS-B) is subcloned using appropriate restriction enzymes into a plasmid vector e.g. pBluescript—Stratagene. The cDNA insert which is to form the labelled probe is released from the vector via digestion with appropriate restriction enzymes and the insert is separated from the vector via electrophoresis in a 1% (w/v) agarose gel. After removal of the separated insert from the agarose gel and purification it is labelled by standard techniques such as random priming and polymerisation (Feinberg and Vogelstein 1983 Anal Biochem 132,6) or nick translation (Rigby et al 1977 J Mol Biol 113,237) with $^{32}$P or DIG-labelled nucleotides. Alternatively, if the probe cDNA insert is cloned into a vector containing strong bacteriophage promoters to which DNA-dependant RNA polymerases bind (SP6, T3 or T7 polymerases), synthetic cRNA is produced by in vitro transcription which incorporates $^{32}$P or digoxygenin nucleotides. Other regions of the rat DRG sodium channel cDNA can also be used as probes in a similar fashion for cDNA library screening or Northern blot analysis. Specifically, a probe is made using a kit such as the Pharmacia oligo labelling kit. This will radioactively label the rat DRG sodium channel cDNA fragment. 50 ng of denatured DNA (place in boiling waterbath for 5 minutes), 3 μl of $^{32}$PdCTP (Amersham) and 10 μl reagent mix is made up to 49 μl with distilled water. 1 μl of Klenow fragment is added and the mixture is incubated at 37° C. for one hour. To remove unincorporated nucleotides, the reaction mixture is applied to a Nick column (Sephadex G50-Pharmacia) followed by 400 μl of TE (10 mM Tris chloride (pH7.4) 1 mM EDTA (pH8.0)). Another 400 μl of TE is added and the eluate is collected. This contains the labelled DNA to be used as a hybridisation probe.

2.5 cDNA Library Screening

In order to detect recombinants containing human homologues of the rat DRG sodium channel the human DRG cDNA library is screened using moderate stringency hybridisation washes (50–60° C., 5×SSC, 30 minutes), using radiolabelled or other labelled DNA or cRNA probes derived from the 3' untranslated region as described above. Libraries are screened using standard methodologies involving the production of nitrocellulose or nylon membrane replicas of DNA from recombinant plaques formed on agar plates (Benton et al 1977 Science 196;180). These are then hybridised to single stranded nucleic acid probes (see above). Moderate stringency washes are carried out (see wash conditions for Northern analysis in section 2.2). Plaques which are positive on duplicate filters (i.e. not artefacts or background) are then purified by one or more rounds of replating after dilution to separate the colonies and further hybridisation screening. Resulting positive plaques are purified, DNA is extracted and the insert sizes of these clones is examined. The clones are cross-hybridised to each other using standard techniques (Sambrook et al 1989 Molecular Cloning Second Edition Cold Spring Harbor Laboratory Press, Cold Spring Harbor, N.Y.) and distinct positive clones identified. Detailed protocols for cDNA library screening are given in example 1.

2.6 Derivation of a Full-length Clone of the Human Homologue of the Rat DRG Sodium Channel cDNA Overlapping positive clones from above are identified by cross-hybridisation. They are then restriction mapped to identify their common portions and restriction fragments representing the separate portions from the overlapping clones are ligated together using standard cloning techniques (Sambrook et al 1989 Molecular Cloning Second Edition Cold Spring Harbor Laboratory Press). For example, the most 5' fragment will contain any 5' untranslated sequence, the start codon ATG and 5' coding sequence. The most 3' clone will contain the most 3' coding sequence, a stop codon and any 3' untranslated sequence, a poly A consensus sequence and possibly a poly A run. Thus a recombinant molecule is generated which contains the full cDNA sequence of the human homologue of the rat DRG sodium channel cDNA. If overlapping clones do not produce sufficient fragments to assemble a full length cDNA clone, the full length oligo dT-primed human DRG library is re-screened to isolate a full length clone. Alternatively, a full length clone is derived directly from the library screening.

2.7 Characterisation of the Human Homologue Full-length Clone

The cDNA sequence from the full-length clone is used as a probe in Northern blot analysis to detect the messenger RNA size in human tissue for comparison with the rat messenger RNA size (see sections 1.1 and 2.2 for methodology).

Confirmation of biological activity of the cloned cDNA is carried out via in vitro translation of the human sodium channel mRNA and its expression in Xenopus oocytes in an analogous manner to that for the rat DRG-specific TTXi resistant sodium channel as described in examples 4 and 7.

cDNA sequences which are shown to have activity as defined above are completely sequenced using dideoxy-mediated chain termination sequencing protocols (Sanger et al 1977 Proc Natl Acad Sci 74,5463).

EXAMPLE 3

Polymerase Chain Reaction (PCR) Approaches to Clone the Human DRG Sodium Channels Using DNA Sequence Derived from the Rat DRG Sodium Channel cDNA Clone Total RNA and poly A+ RNA is isolated from human dorsal root ganglia or trigeminal ganglia or other cranial ganglia from post-mortem human material or foetuses as described in example 2 above.

Random primers are hybridised to the RNA followed by polymerisation with MMLV reverse transcriptase to generate single stranded cDNA from the extracted human RNA.

Using degenerate PCR primers derived from relatively conserved regions of the known voltage-gated sodium channels (FIG. 2), amplify the cDNA using the polymerase chain reaction (Saiki et al 1985 Science 230,1350). It is appreciated by those skilled in the art that there are many variables which can be manipulated in a PCR reaction to derive the homologous sequences required. These include but are not limited to varying cycle and step temperatures, cycle and step times, number of cycles, thermostable polymerase, Mg2+ concentration. It is also appreciated that greater specificity can be gained by a second round of amplification utilising one or more nested primers derived from further conserved sequence from the sodium channels.

Specifically, the above can be accomplished in the following manner. The first strand cDNA reaction consists of 1 $\mu$g of total RNA made up to 13 $\mu$l with DEPC-treated water and 1 $\mu$l of 0.5 $\mu$g/$\mu$l oligo(dT). This is heated to 70° C. for 10 minutes and then incubated on ice for 1 minute. The following is then added: 2 $\mu$l of 10 × synthesis buffer (200 mM Tris chloride, 500 mM potassium chloride, 25 mM magnesium chloride, 1 $\mu$g/ml BSA), 2 $\mu$l of 0.1M DTT, 1 $\mu$l of 200 U/$\mu$l Superscript Reverse Transcriptase (Gibco BRL). This is incubated at room temperature for 10 minutes then at 42° C. for 50 minutes. The reaction is then terminated by incubating for 15 minutes at 70° C. 1 $\mu$l of E.coli RNase H (2 U/$\mu$l) is added to the tube which is then incubated for 20 minutes at 37° C.

The PCR reaction is set up in a 0.5 ml thin-walled Eppendorf tube. The following reagents are added: 10 $\mu$l 10× PCR buffer, 1 $\mu$l cDNA,16 $\mu$l dNTP's (25 $\mu$l of 100 $\mu$M dATP,dCTP, dCTP and dGTP into 900 $\mu$l sterile distilled water), 7 $\mu$l of 25 mM magnesium chloride, 1 $\mu$l of Taq DNA polymerase (Amplitaq Perkin-Elmer)plus sterile distilled water to 94 $\mu$l.

To each reaction tube a wax PCR bead is added (Perkin-Elmer) and the tube placed in a 70° C. hot block for 1 minute. The tubes are allowed to cool until the wax sets and 3 $\mu$l of each primer (33 pM/$\mu$l) are added above the wax. The tubes are placed in a thermal cycler (Perkin-Elmer) and the following 3-step program used after an initial 94° C. for 5 minutes; 92° C. for 2 minutes, 55° C. for 2 minutes, 72° C. for 2 minutes for 35 cycles. A final polymerisation step is added at 72° C. for 10 minutes. The reaction products are then run on a 1% agarose gel to assess the size of the products. In addition, control reactions are performed alongside the samples. These should be: 1) all components without cDNA (negative control) and 2) all reaction components with primers for constitutively expressed product e.g. $\alpha$-actin or HPRT.

The products of the PCR reactions are examined on 0.8%–1.2% (w/v) agarose gels. Bands on the gel (visualised by staining with ethidium bromide and viewing under UV light) representing amplification products of the approximate predicted size were then cut from the gel and the DNA purified. Further bands of interest are also identified by Southern blot analysis of the amplification products and probing of the resulting filters with labelled primers from further conserved regions e.g. those used for secondary amplification.

The resulting DNA is ligated into suitable vectors such as, but not limited to, pCR II (Invitrogen) or pGemT. Clones are then sequenced to identify those containing sequence with similarity to the rat DRG sodium channel sequence (SNS-B).

Clone Analysis

Candidate clones from above are used to screen a human cDNA DRG library constructed using methods described in example 2. If a full length clone is not identified, positive overlapping clones which code for the full length human cDNA homologue are identified and a full length clone is then assembled as described in example 1. Biological activity is then confirmed as described in examples 4 and 7.

EXAMPLE 4

In vitro Translation of Rat and Human DRG Sodium Channel in *Xenopus laevis* Oocytes In order to demonstrate the biological activity of the protein coded for by the rat DRG sodium channel cDNA sequence (SNS-B) and its human homologue the complete double-stranded cDNA coding sequences are ligated into in vitro transcription vectors (including but not limited to the pGEM series, Promega) using one or more of the available restriction enzyme sites such that the cDNAs are inserted in the correct orientation. The constructs are then used to transform bacteria and constructs with the correct sequence in the correct orientation are identified via diagnostic restriction enzyme analysis and dideoxy-mediated chain termination DNA sequencing (Sanger et al 1977 Proc Natl Acad Sci 74,5463).

These constructs are then linearised at a restriction site downstream of the coding sequence and the linearised and purified plasmids are then utilised as a template for in vitro transcription. Sufficient quantities of synthetic mRNA are produced via in vitro transcription of the cloned DNA using a DNA-dependent RNA polymerase from a bacteriophage that recognises a bacteriophage promoter found in the cloning vector. Examples of such polymerases include (but are not limited to) T3, T7 and SP6 RNA polymerase.

A variation on the above method is the synthesis of mRNA containing a 5' terminal cap structure (7-methylguanosine) to increase its stability and enhance its translation efficiency (Nielson and Shapiro 1986 Nuc Ac Res 14,5936). This is accomplished by the addition of 7-methylguanosine to the reaction mixture used for synthetic mRNA synthesis. The cap structure is incorporated into the 5' end of the transcripts as polymerisation occurs. Kits are available to facilitate this process e.g. mCAP RNA Capping Kit—Stratagene).

The synthetic RNA produced from the in vitro transcription is isolated and purified. It is then translated via micro-injection into Xenopus laevis oocytes. 50 nls of 1 mg/ml synthetic RNA is micro-injected into stage 5 or stage 6 oocytes according to methods established in the literature (Gurdon et al (1983) Methods in Enzymol 101,370). After incubation to allow translation of the mRNAs the oocytes are analysed for expression of the DRG sodium channels via electrophysiological or other methods as described in example 7.

A further method for expression of functional sodium channels involves the nuclear injection of a Xenopus oocyte protein expression vector such as pOEV (Pfaff et al., Anal. Biochem. 188, 192–195 (1990)) which allows cloned DNA to be transcribed and translated directly in the oocyte. Since proteins translated in oocytes are post-translationally modified according to conserved eukaryotic signals, these cells offer a convenient system for performing structural and functional analyses of cloned genes. pOEV can be used for direct analysis of proteins encoded by cloned cDNAs without preparing mRNA in vitro, simplifying existing protocols for translating proteins in oocytes with a very high translational yield. Transcription of the vector in oocytes is driven by the promoter for the TFIIIA gene, which can generate 1–2 ng (per oocyte within 2 days) of stable mRNA template for translation. The vector also contains SP6 and T7 promoters for in vitro transcription to make mRNA and hybridization probes. DNA clones encoding SNS channel transcripts are injected into oocyte nuclei and protein accumulated in the cell over a 2- to 10-day period. The presence of functional protein is then assessed using twin electrode voltage clamp as described in example 7.

EXAMPLE 5

Expression of Rat and Human DRG Sodium Channel in Mammalian Cells

In order to be able to establish a mammalian cell expression system capable of producing the sodium channel in a stable bioactive manner, constructs have to be first generated consisting of the cDNA of the channel in the correct vectors suitable for the cell system in which it is desired to express the protein. There are available a range of vectors containing strong promoters which drive expression in mammalian cells.

i/Transient Expression

In order to determine rapidly the bioactivity of a given cDNA it can be introduced directly into cells and resulting protein activity assayed 48–72 hours later. Although this does not result in a cell line which is stably expressing the protein of interest it does give a quick answer as to the biological activity of the molecule. Specifically, the cDNA representing the human or rat DRG sodium channel is ligated into appropriate vectors (including but not limited to pRc/RSV, pRc/CMV, pcDNA1 (Invitrogen)) using appropriate restriction enzymes such that the resulting construct contains the cDNA in the correct orientation and such that the heterologous promoter can drive expression of the transcription unit. The resulting expression constructs are introduced into appropriate cell lines including but not limited to COS-7 cells (an African Green Monkey Kidney cell line), HEK 293 cells (a human embryonic kidney cell line) and NIH3T3 cells (a murine fibroblastic cell line). The DNA is introduced via standard methods (Sambrook et al 1989 Molecular Cloning Second Edition, Cold Spring Harbour Laboratory Press) including but not limited to calcium phosphate transfection, electroporation or lipofectamine (Gibco) transfection. After the required incubation time at 37° C. in a humidified incubator the cells are tested for the presence of an active rat DRG sodium channel using methods described in example 7.

ii/Stable Expression

The production of a stable expression system has several advantages over transient expression. A clonal cell line can be generated that a has a stable phenotype and in which the expression levels of the foreign protein can be characterised and, with some expression systems, controlled. Also, a range of vectors are available which incorporate genes coding for antibiotic resistance, thus allowing the selection of cells transfected with the constructs introduced. Cell lines of this type can be grown in tissue culture and can be frozen down for long-term storage. There are several systems available for accomplishing this e.g. CHO, CV-1, NIH-3T3.

Specifically COS-7 cells can be transfected by lipofection using Lipofectamine (GibcoBRL) in the following manner. For each sample $2\times10^6$ cells are seeded in a 90 mm tissue culture plate the day prior to transfection. These are incubated overnight at 37° C. in a $CO_2$ incubator to give 50–80% confluency the following day. The day of the transfection the following solutions are prepared in sterile 12×75 mm tubes: Solution A: For each transfection, dilute 10–50 µg of DNA into 990 µl of serum-free media (Opti-MEM I Reduced Serum Medium GibcoBRL). Solution B: For each transfection, dilute 50 μl of Lipofectamine Reagent into 950 μl serum-free medium. The two solutions are combined, mixed gently and incubated at room temp for 45 minutes. During this time the cells are rinsed once with serum-free medium. For each transfection 9 ml of serum-free medium is added to the DNA-lipofectamine tubes. This solution is mixed gently and overlayed on the rinsed cells. The plates are incubated for 5 hours at 37° C. in a $CO_2$ incubator. After the incubation the medium is replaced with fresh complete media and the cells returned to the incubator. Cells are assayed for activity 72 hours post transfection as detailed in examples 4 and 7. To ascertain the efficiency of transfection, β-galactosidase in pcDNA3 is transfected alongside the DRG sodium channel cDNA. This control plate is stained for 13-galactosidase activity using a chromogenic substrate and the proportion of cells staining calculated. For transient transfection of DRG the cDNA must first be cloned into a eucaryotic expression vector such as pcDNA3 (Invitrogen).

EXAMPLE 6

Expression of Rat DRG Sodium Channel in Insect Cells

The baculovirus expression system uses baculovirus such as *Autographa californica* nuclear polyhedrosis virus (AcNPV) to produce large amounts of target protein in insect cells such as the Sf9 or 21 clonal cell lines derived from *Spodoptera frugiperda* cells. Expression of the highly abundant polyhedrin gene is non-essential in tissue culture and its strong promoter (polh) can be used for the synthesis of foreign gene products (Smith et al 1983 Mol Cell Biol 3,2156–2165). The polyhedrin promoter is maximally expressed very late in infection (20 hours post infection).

A transfer vector, where the rat DRG sodium channel cDNA is cloned downstream of the polh promoter, or another late promoter such as p10, is transfected into insect cells in conjunction with modified AcNPV viral DNA such as but not limited to BaculoGold DNA (PharMingen). The modified DNA contains a lethal mutation and is incapable of producing infectious viral particles after transfection. Co-transfection with a complementing transfer vector such as (but not limited to) pAcYM1 (Matsuura et al 1987 J Gen Virol 68,1233–1250) or pVL1392/3 (InVitrogen) allows the production of viable recombinant virus. Although more than 99% of the resultant virus particles should be derived from plasmid-rescued virus it is desirable to further purify the virus particles by plaque assay. To ensure that the recombinant stock is clonal, a single plaque is picked from the plaque assay and amplified to produce a recombinant viral stock. Once the recombinant phenotype is verified the viral stock can be used to infect insect cells and express functional rat DRG sodium channel. There are a number of variations in the methodology of baculovirus expression which may give increased expression (O'Reilly et al 1992 Baculovirus Expression Vectors: A Laboratory Manual. Oxford University Press). The expression of the rat or human DRG sodium channel is achieved by cloning of the cDNA into pVL1392 and introducing this into Sf21 insect cells.

EXAMPLE 7

Electrophysiological Characterisation of Cloned Human and Rat DRG Sodium Channel Expression

*Xenopus laevis* oocytes are used to express the channel after injection of the mRNA or cDNA in an expression vector. Expression would be transient and thus functional studies would be made at appropriate times after the injections. Comparison with mock-injected oocytes would demonstrate lack of the novel channel as an endogenously expressed characteristic. Standard two electrode voltage clamp (TEVC) techniques as described, for example, in Fraser, Moon & Djamgoz (1993) Electrophysiology of Xenopus oocytes: an expression system in molecular neurobiology. In: Electrophysiology: A practical approach. Wallis, D. I., ed. Oxford University Press. Chapter 4 pp. 65–86, would be used to examine the characteristics of responses of ionic currents to changes in the applied membrane potential. Appropriately modified saline media would be used to manipulate the type of ionic currents detectable. The kinetics of activation and inactivation of the sodium current, its ionic selectivity, the effects of changes in ionic concentration of the extracellular medium on its reversal potential, and the sensitivity (or resistance) to TTX would be defining characteristics.

Similar electrophysiological studies would be undertaken to assess the success of functional expression in a permanently or transiently expressing mammalian cell line, but patch clamp methods would be more suitable than TEVC. Whole cell, cell-attached patch, inside-out patch or outside-out patch configurations as described for example by Hamill et al. (1981) Pflugers Arch. 391:85–100 and Fenwick et al. (1982) J. Physiol. 331 599–635 might be used to assess the channel characteristics.

For example, isolated transfected cells (see above) will be voltage-clamped using the whole-cell variant of the patch clamp technique for recording the expressed sodium channel current.

Recordings will be obtained at room temperature (22–24° C.). Both external and internal recording solutions will be used to isolate Na+ currents as previously described (Lalik et al., Am. J. Physiol. 264:C803–C809, 1992; West et al., Neuron 8:59–70, 1992). External solution (mM): sodium chloride, 65; choline chloride, 50; TEA-Cl, 20, KCl, 1.5; calcium chloride, 1; magnesium chloride, 5; glucose 5; HEPES, 5; at a pH 7.4 and and osmolality of 320. Internal solution (mM):CsF, 90; CsCl, 60; sodium chloride, 10; $MgCl_2$, 2;EGTA, 10; HEPES, 10 at pH 7.2 and an osmolarity of 315.

The kinetics and voltage parameters of the expressed sodium channel current will be examined and compared with data existing in the literature. These include current-voltage relationships and peak current amplitude. Cells will be voltage-clamped at −70 mV and depolarizing pulses to 50 mV (at 10 mV increments) will be used to generate currents.

The pharmacology of the expressed sodium channel current will be examined with the Na channel blocker, tetrodotoxin (TTX). To date sodium channels have been classified as TTX-sensitive and TTX-resistant: block by low (1–30 nM) and high (>1 μM) concentrations of TTX, respectively (Elliot & Elliot, J. Physiol. (Lond.) 463:39–56, 1993; Yang et al., J. Neurosci. 12:268–277, 1992; W1992).

The channel is unaffected by concentrations lower than 1 micromolar tetrodotoxin, and is only partially blocked by concentrations as high as 10 micromolar tetrodotoxin.

EXAMPLE 8

Production of Purified Channel

Using a commercial coupled transcription-translation system, 35-S methionine labelled protein products of the SNS clone can be generated (see FIG. 3). The size of the resulting protein when assessed by SDS-polyacrylamide gel electrophoresis confirms the predicted size of the protein deduced by DNA sequencing. The system used is the Promega TNT system (Promega Technical Bulletin 126 1993). The experiment is carried out precisely according to the protocol provided (see FIG. 3).

EXAMPLE 9
Use of Rat or Human Sodium Channel in Screening Assays

Cell lines expressing the cloned sodium channels could be used to determine the effects of drugs on the ability of the channels to pass sodium ions across the cell membranes, e.g to block the channels or to enhance their opening. Since the channel activation is voltage dependent, depolarising conditions will be required for observation of baseline activity that would be modified by drug actions. Depolarisation could be achieved by for example raising extracellular potassium ion concentration to 20 or 40 mM, or by repeated electrical pulses. Detection of the activation of sodium conducting channels could be achieved by flux of radiolabelled sodium ions, guanidine or by reporter gene activation leading to for example a colour change or to fluorescence of a light emitting protein. Subsequent confirmation of the effectiveness of the drug action on sodium channel activity would require electrophysiological studies similar to those described above.

EXAMPLE 10
In vitro Influx Assays 1. 22Na+ influx assay: A modified assay has been adapted from methods reported by Tamkum and Catterall, Mol Pharm. 19:78, (1981). Oocytes or cells expressing the sodium channel gene are suspended in a buffer containing 0.13 M sodium chloride, 5 mM KCl, 0.8 mM $MgSO_4$, 50 mM HEPES-Tris (pH 7.4), and 5.5 mM glucose. Aliquots of the cell suspension are added a buffer containing 22NaCl (1.3 $\mu$Ci/ml, New England Nuclear, Boston, Mass.), 0.128 M choline chloride, 2.66 mM sodium chloride, 5.4 mM KCl, 0.8 mM $MgSO_4$, 50 mM HEPES-Tris (pH 7.4), 5 mM ouabain, 1 mg/ml bovine serum albumin, and 5.5 mM glucose and then incubated at 37° C. for 20 sec in either the presence or absence of 100 $\mu$M veratridine (Sigma Chemical Co., St Louis, Mo.). The influx assay is stopped by the addition of 3 ml of ice-cold wash buffer containing 0.163 M sodium chloride, 0.8 mM $MgSO_4$, 1.8 mM $CaCl_2$, 50 mM HEPES-Tris (pH 7.4) and 1 mg/ml bovine serum albumin, collected on a glass fiber filter (Whatman GF/C), and washed twices with 3 ml of wash buffer. Radioactive incorporation is determined by with a gammacounter. The specific tetrodotoxin-resistant influx is measured by the difference in 22Na+ uptake in the absence or the presence of 10 $\mu$M transmethrin or 1 $\mu$M (+) trans allethrin. The tetrodotoxin-sensitive influx is measured by the difference in 22Na+ uptake in the absence or the presence of 1 $1\mu$M tetrodotoxin (Sigma Chemical Co., St Louis, Mo.).

Guanidine influx: Another assay is modified from the method described by Reith, Eur. J. Pharmacol. 188:33 (1990). In this assay sodium ions are substituted with guanidinium ions. Oocytes or cells are washed twice with a buffer containing 4.74 mM KCl, 1.25 mM $CaCl_2$, 1.2 mM KH2PO4, 1.18 mM $MgSO_4$, 22 mM HEPES (pH 7.2), 22 mM choline chloride and 11 mM glucose. The oocytes or cells are suspended in the same buffer containing 250 $\mu$M guanidine for 5 min at 19–25° C. An aliquot of 14C-labelled guanidine hydrochloride (30–50 mCi/mmol supplied by New England Nuclear, Boston, Mass.) is added in the absence or presence of 10 $\mu$M veratridine, and the mixture is incubated for 3 min. The uptake reaction is stopped by filtration through Whatman GF/F filters and followed by 25 ml washes with ice-cold 0.9% saline. Radioactive incorporation is determined by scintillation counting.

EXAMPLE 11
In order to measure the expression of sodium channels in in vitro systems, as well as to analyse distribution and relative level of expression in vivo, and to attempt to block function, polyclonal and monoclonal antibodies will be generated to peptide and protein fragments derived from SNS protein sequence shown in FIG. 1.

a) Immunogens

Glutathione-sulphotransferase (GST)—fusion proteins will be constructed (Smith and Johnson Gene 67:31–40 (1988)) using PGEX vectors obtained from Pharmacia. Fusion proteins including both intracellular and extracellular loops with little homology with known sodium channels other than SNS-B will be produced. One such method involves subcloning of fragments into pGex-5X3 or pGEX 4t-2 to produce in-frame fusion proteins encoding extracellular, intracellular or C-terminal domains as shown in detailed maps in FIG. 4. The pGEX fusion vectors are transformed into E. coli XL-1 blue cells or other appropriate cells grown in the presence of ampicillin. After the cultures have reached an optical density of OD600>0.5, fusion protein synthesis is induced by the addition of 100 micromolar IPTG, and the cultures further incubated for 1–4 hours. The cells are harvested by centrifugation and washed in ice cold phosphate buffered saline. The resulting pellet (dissolved in 300 microliters PBS from each 50 ml culture) is then sonicated on ice using a 2 mm diameter probe, and the lysed cells microfuged to remove debris. 50 microliters of glutathione-agarose beads are then added to each pellet, and after gentle mixing for 2 minutes at room temperature, the beads are washed by successive spins in PBS. The washed beads are then boiled in Laemmli gel sample buffer, and applied to 10% polyacrylamide SDS gels. Material migrating at the predicted molecular weight is identified on the gel by brief staining with coommassie blue, and comparison with molecular weight markers. This material is then electroeluted from the gel and used as an immunogen as described below.

b) Antibody Production

Female Balb/c mice are immunised intraperiteonally with 1–100 micrograms of GST fusion protein emulsified in Freunds complete adjuvant. After 4 weeks, the animals will be further immunised with fusion proteins (1–100 micrograms) emulsified in Freunds incomplete adjuvant. Four weeks later, the animals will be immunised intraperitoneally with a further 1–100 micrograms of GST fusion protein emulsified with Freunds incomplete adjuvant. Seven days later, the animals will be tail bled, and their serum assessed for the production of antibodies to the immunogen by the following screen; (protocols for the production of rabbit polyclonal serum are the same, except that all injections are subcutaneous, and 10 times as much immunogen is used. Polyclonal rabbit serum are isolated from ear-vein bleeds.)

Serial ten-fold dilutions of the sera (1;100 to 1; 1,000,000) in phosphate buffered saline (PBS) containing 0.5% NP-40 and 1% normal goat serum will be applied to 4% paraformaldehyde-fixed 10 micron sections of neonatal rat spinal cord previously treated with 10% goat serum in PBS, After overnight incubation, the sections are washed in PBS, and further incubated in the dark with 1;200 FITC-conjugated F(ab)2 fragment of goat anti-mouse antibodies for 2 hours in PBS containing 1% normal goat serum. The sections are further washed in PBS, mounted in Citifluor, and examined by fluorescence microscopy. Those sera that show specific staining of laminar II in the spinal cord will be retained, and the mice generating such antibodies subsequently used for the production of monoclonal antibodies. Three weeks later, mice producing useful antibodies are immunised with GST—fusion proteins without adjuvant.

After 3 days, the animals are killed, their spleens removed, and the lymphocytes fused with the thymidine kinase-negative myeloma line NSO or equivalent, using polyethylene glycol. The fused cells from each experiment are grown up in 3×24 well plates in the presence of DMEM medium containing 10% fotal calf serum and hypoxanthine, aminopterin and thymidine (HAT) medium to kill the myeloma cells (Kohler and Milstein, Eur. J. Immunol 6, 511–519 (1976)). The tissue culture supernatants from wells containing hybridomas are further screened by immunofluorescence as described above, and cells from positive wells cloned by limiting dilution. Antibody from the positive testing cloned hybridomas is then used to Western blot extracts of rat dorsal root ganglia, to detemine if the antibody recognises a band of size approximately 200,000, confirming the specificity of the monoclonal antibody for the SNS sodium channel. Those antibodies directed against extracellular domains that test positive by both of these criteria will then be assessed for function blocking activity in electrophysiological tests of sodium channel function (see example 7), and in screens relying on ion flux or dye-based assays in cells lines expressing sodium channel (see examples 9 and 10).

EXAMPLE 12
Cell-type Distribution of Expression

In situ hybridization demonstrates the presence of SNS in a subset of sensory neurons. An SNS fragment between positions 1740 and 1960 was sub-cloned into pGem4z, and DIG-UTP labeled sense or antisense cRNA generated. Sample preparation, hybridization, and visualization of in situ hybridization with alkaline phosphatase conjugated anti-DIG antibodies was carried out exactly as described in Schaeren-Wimers N. and Gerfin-Moser A. Histochemistry 100, 431–440 (1993).

EXAMPLE 13
Electrophysiological Properties of the Rat DRG Sodium Channel Expressed in Xenopus Oocytes pBluescript SK plasmid containing DNA encoding the SNS sodium channel was digested to position-21 upstream of the initiator methionine using a commercially available kit (Erase a base system, Promega, Madison, Wis., USA). The linearized and digested plasmid was cut with Kpn 1 and subcloned into an oocyte expression vector pSp64GL (Sma-Kpn1) sites. pSP64GL is derived from pSP64.T pSP64.T was cut with Sma1-EcoRI, blunt-ended with Klenow enzyme, and recircularized. Part of the pGem 72 (+) polylinker (Sma1-Kpn1-EcoR1-Xhol) was ligated into the blunt-ended Bgl II site of pSP64.T. This vector with an altered polylinker for DNA inserts (Sma1-Kpn1-EcoR1-Xhol) and linearization (Sal1-Xba 1-BamH1) was named pSP64GL. The resulting plasmid was linearized with Xba1, and cRNA transcribed with SP6 polymerase using 1 mM 7-methylGppG.

cRNA (70 ng) was injected into Xenopus oocytes 7–14 days before recording; immature, stage IV oocytes were chosen cause of their smaller diameter and therefore capacitance. Oocytes were impaled with 3M KCl electrodes (<1 MΩ) and perfused at 3–4 ml per minute with modified Ringer solution containing 115 mM NaCl, 2.5 mM KCl, 10 mM HEPES, 1.8 mM $MgCl_2$, and 1 mM $CaCl_2$, pH 7.2, at temperature of 19.5–20.5° C. Digital leak substraction of two electrode voltage-clamp current records was carried out using as leak currents produced by hyperpolarizing pulses of the same amplitude as the test depolarizing commands. Oocytes in which leak commands elicited time-dependent currents were discarded. Averages of 10 records were used for both test and leak.

Inward currents were evoked by depolarizing, in 10 mV steps, from −60 mV to a command potential of −20 to +40 mV in 10 mV steps and from −80 mV to a command potential of −30 to +2− mV in oocytes injected with sodium channel cRNA. Current traces are blanked for the first 1.5 ms from the onset of the voltage step to delete the capacity transients for clarity. The peak current is reached at the same command voltage for the two holding potentials, but is slightly smaller from −60 mV because of steady-state inactivation.

The effects of 50% or 100% replacement of external Na+ by N-methyl-D-glucosamine on the sodium channel current were elicited by stepping the depolarizing currents given to the oocyte from −60 to +1 mV. Data were fitted with the equation $h_x = 1/(1+\exp((V-V_{50})/k))$, where V is the prepulse potential, $V_{50}$ the potential of 50% inactivation and the k the slope factor (best squares fit). The effect of TTX (10 μM and 100 μM) on the peak $Na^+$ current (test pulse from −60 to +20 mV) was also determined. The effect was quickly reversible upon washout.

After a minimum incubation of 7 days from cRNA injection, step depolarizations to potentials positive to −30 mV elicited inward currents which peaked between +10 and +20 mV with an average maximum amplitude of 164±72 nA (from −60 mV holding potential, n=13) and a reversal potential of +35.5±2.2 mV (n=10). The inward current was reversed by total replacement of Na+ in the external medium with an impermeant cation (N-methyl-D-glucosamine). The current's reversal potential was shifted in 50% Na+ by 13.7±3.2 mV in the hyperpolarizing direction (n=3; predicted value for a Na+-selective channel, 17.5 mV). The inactivation produced by a 1s prepulse was half-maximal at -30.0±1.3 mV (slope factor 14.0±1.7 mV, n=5.

TTX had no effect at nanomolar concentrations, and produced only a 19.1±8.3% reduction at 10 μM, n=3). The estimated half-maximal inhibitory concentration ($IC_{50}$) was 59.6±10.1 μM TTX.

The local anesthetic lignocaine was also weakly inhibitory, producing a maximum block of 41.7±5.4% at 1 mM on the peak current elicited by depolarizing pulses from −60 mV to +10 mV (1 every min; n=3), whereas under the same conditions 100 μM phenytoin had no effect.

A similarity with the TTX-insensitive Na+ current of DRG neurons was the effectiveness and rank order of $Pb^{2+}$ versus $Cd^{2+}$ in reducing peak $Na^+$ currents (−63.9±18.1% for $Pb^{2+}$ versus −24.4±7.9% for $Cd^{2+}$ at 50 μM and 100 μM, respectively; n=3, P=0.0189). The electrophysiological and pharmacological characteristics of the oocyte expressed DRG sodium channel are thus similar to the properties of the sensory neuron TTX-insensitive channel, given the constraints of expression in an oocyte system. In oocytes expressing the DRG sodium channel, the peak of the I/V plot occurred at a more depolarized potential than that of the DRG TTX-insensitive current, despite a similar reversal potential. This difference may reflect the absence of the accessory β1 subunit found in DRG, which is known to shift activation to more negative potentials when expressed with the subunit of other $Na^+$ channels. In addition, splice variants that exhibit an activation threshold more negative to SNS sodium channel may shift activation to the more negative potentials observed in sensory neurons.

EXAMPLE 14
Distribution of DRG Sodium Channel in Neonatal and Adult Rat Tissuesand Cell Lines Northern blot and reverse transcriptase-polymerase chain reaction (RT-PCR) were used to examine neonatal and adult rat tissues for expression of the DRG sodium channel messenger RNA.

Random primed $^{32}$P-labeled DNA Pst -Acc1 fragment probes (50 ng, specific activity $2\times10^9$ c.p.m. per µg DNA) from interdomain region 1 (nucleotide position 1,478–1, 892) of the SNS sodium channel nucleic acid sequence were used to probe total RNA extracted from tissues. The following tissues and cell lines were tested: central nervous system and non-neuronal tissues from neonatal rats; peripheral nervous tissue including neonatal Schwann cells and sympathetic neurons, as well as C6 glioma, human embryonal carcinoma line N-tera-2 and N-tera-2 neuro, rat sensory neuron-derived lines ND7 and ND8, and human neuroblastomas SMS-KCN and PC12 cells grown in the presence of NGF; adult rat tissue including pituitary, superior cervical ganglia, coeliac ganglia, trigeminal mesencephalic nucleus, vas deferens, bladder, ileum and DRG of adult animals treated with capsaicin (50 mg/kg) at birth and neonatal DRG control. Total RNA (10 µg) or 25 µg of RNA from tissues apart from superior cervical ganglion sample (10 µg) and capsaicin-treated adult rat DRG (5 µg) were northern blotted.

Total RNA was separated on 1.2% agarose-formaldehyde gels, and capillary blotted onto Hibond-N filters (Amersham). The amounts of RNA on the blot were roughly equivalent, as judged by ethidium bromide staining of ribosomal RNA and by hybridization with the ubiquitously expressed L-27 ribosomal protein transcripts. Filters were prehybridized in 50% formamide, 5×SSC containing 0.5% sodium dodecyl sulfate, 5×Denhardts solution, 100 µg/ml boiled sonicated salmon sperm DNA (average size 300 bp),10 µg/ml poly-U and 10 µg/ml poly-C at 45° C. for 6 h. After 36 hours hybridization in the same conditions using $10^7$ c.p.m. per ml hybridization probe, the filters were briefly washed in 2×SSC at room temperature, then twice with 2×SSC with 0.5% SDS at 68° C. for 15 min, followed by a 20 min wash in 0.5% SDS, 0.2×SSC at 68° C. The filters were autoradiographed overnight or for 4 days on autoradiography film (Kodak X-omat).

For RT-PCR experiments, 10 µg total RNA from neonatal rat tissues (spleen, liver, kidney, lung, intestine, muscle, heart, superior cervical ganglia, spinal cord, brain stem, hippocampus, cerebellum, cortex and dorsal root ganglia), or 2 µg total RNA from control or capsaicin-treated rat DRG or DRG neurons in culture were treated with DNase I and extracted with acidic phenol to remove genomic DNA.

cDNA was synthesized with Superscript reverse transcriptase using oligo dT(12–18) primers and purified on Qiagen 5 tips. Polymerase chain reaction (PCR) was used to amplify cDNA (35 cycles, 94° C., 1 min; 55° C., 1 min; and 72° C., 1 min), and products separated on agarose gels before staining with ethidium bromide. L-27 primers (Ninkina et al. (1983) Nucleic Acids Res. 21, 3175–3182) were added to the PCR reaction 5 cycles after the start of the reaction with the DRG sodium channel specific primers which comprised 5'-CAGCTTCGCTCAGAAGTATCT-3+ (SEQ ID NO: 9) and

5'-TTCTCGCCGTTCCACACGGAGA-3' (SEQ ID NO: 10).

Transcription of mRNA coding for the DRG sodium channel could not be detected in any non-neuronal tissues or in the central nervous system using northern blots or reverse transcription of mRNA and the polymerase chain reaction. Sympathetic neurons from the superior cervical ganglion and Schwann cell-containing sciatic nerve preparations, as well as several neuronal cell lines were also negative. However, total RNA extracts from neonatal and adult rat DRG gave a strong signal of size about 7 kb on northern blots. These data suggest that the DRG sodium channel is not expressed only in early development.

RT-PCR of oligo dT-primed cDNA from various tissues using DRG sodium channel primers and L-27 ribosomal protein primer showed the presence of DRG sodium channel transcripts in DRG tissue only.

RT-PCR was also performed on DRG-sodium channel and L-27 transcripts from DRG neurons cultured and treated with capsaicin (overnight 10 µM) or dissected from neonatal animals treated with capsaicin (50 mg/kg on 2 consecutive days, followed by DRG isolation 5 days later. The signal from the L-27 probe was the same in capsaicin-treated cell cultures or animals as compared with controls that were not treated with capsaicin. There was a significant diminution in the DRG sodium channel signal from capsaicin-treated cultures or animals as compared with controls. Control PCR reactions without reverse transcriptase treatment were also done to control for contaminating genonic DNA.

When neonatal rats were treated with capsaicin and total adult DRG RNA subsequently examined by northern blotting, the signal was substantially reduced, suggesting that the DRG sodium channel transcript is expressed selectively by capsaicin-sensitive (predominantly nociceptive) neurons. These data were confirmed by RT-PCF experiments on both cultures of DRG neurons, and in whole animal studies.

EXAMPLE 15

Distribution of DRG Sodium Channel in Rat Tissue by in situ Hybridization

In situ hybridization was used to examine the expression of the DRG sodium channel transcripts at the single-cell level in both adult trigeninal ganglia and neonatal and adult rat DRG.

A SNS sodium channel PCR fragment of interdomain region I between positions 1,736 and 1,797 of the SNS sodium channel nucleic acid sequence was subcloned into pGem3Z (Promega, Madison, Wis., USA) and digoxygenin (DIG)-UTP (Boehringer-Mannheim, Germany) labeled sense or antisense cRNA generated using SP6 or T7 polymerase, respectively. Sample preparation, hybridization and visualization of in situ hybridization with alkaline phosphatase conjugated anti-DIG antibodies was carried out as described in Schaeren-Wimers, et al., A. (1993) Histochemistry 100: 431–440, with the following modifications. Frozen tissue sections (10 µM-thick) of neonatal rat lumbar DRG, and adult trigeminal ganglion neurons were fixed for 10 min in phosphate buffered saline (PBS) containing 4% paraformaldehyde. Sections were acetylated in 0.1 M triethanolamine, 0.25% acetic anhydride for 10 min. Prehybridization was carried out in 50% formamide, 4×SSC, 100 µg/ml boiled and sonicated ssDNA, 50 µg/ml yeast tRNA, 2×Denhardts solution at room temperature for 1 h. Hybridization was carried out overnight in the same buffer at 65° C. Probe concentration was 50 ng/ml. Sections were washed in 2×SSC for 30 min at 72° C. for 1 hr and twice in 0.1 SSC for 30 min at 72° C. before visualization at room temperature with anti-digoxygenin alkaline phosphatase conjugated antibodies. The same sections were then stained with mouse monoclonal antibody RT97 which is specific for neurofilaments found in large diameter neurons.

Subsets of sensory neurons from both tissues showed intense signals with a DRG sodium channel-specific probe. Combined immunohistochemistry with the large-diameter neuron-specific monoclonal antibody RT97 and the DRG sodium channel specific probe showed that most of the large diameter neurons did not express the DRG sodium channel transcript. Small diameter neurons were stained with the

EXAMPLE 16
Site Directed Mutagenesis of SNS Sodium Channel-TTX Sensitivity

The SNS sodium channel is 65% homologous to the tetrodotoxin-insensitive cardiac sodium channel. A number of residues that line the channel atrium have been implicated in tetrodotoxin binding. The amino acid sequence of the SNS sodium channel exhibits sequence identity to other tetrodotoxin-sensitive sodium channels in 7 out of 9 such residues. One difference is a conservative substitution at D(905)E. A single residue (C-357) has been shown to play a critical role in tetrodotoxin binding to the sodium channel. In the SNS sodium channel, a hydrophilic serine is found at this position, whereasa other sodium channels that are sensitive to TTX have phenylalanine in this position.

Site-directed mutagenesis using standard techniques and primers having the sequence TGACGCAGGACTCCTGG-GAGCGCC (SEQ ID NO: 31) was used to substitute phenylalanine for serine at position 357 in the SNS sodium channel. The mutated SNS sodium channel, when expressed in Xenopus oocytes produces voltage-gated currents similar in amplitude and time course to the native channel. However, sensitivity to TTX is restored to give an $IC_{50}$ of 2.5 nM (+−0.4, n=5), similar to other voltage-gated sodium channels that have aromatic residues at the equivalent position. The table below shows $IC_{50}$ for SNS sodium channel, and the rat brain iia, muscle type 1, and cardiac tetrodotoxin-insensitive sodium channels.

TTX Sensitivity

| Sodium Channel | ss1 domain | ss2 domain | $IC_{50}$ |
|---|---|---|---|
| Rat brain iia | FRLM | TQDFWENLY | 18 nM |
| muscle type 1 | FRLM | TQDYWENLY | 40 nM |
| cardiac TTXi | FRLM | TQDCWERLY | 950 nM |
| SNS | FRLM | TQDSWERLY | 60 micromolar |
| SNS mutant | FRLM | TQDFWERLY | 2.5 nM |

FRLM—SEQ ID NO: 11; TQDFWENLY—SEQ ID NO: 12;
TQDYWENLY—SEQ ID NO: 13; TQDCWERLY—SEQ ID NO: 14;
TQDSWERLY—SEQ ID NO: 15; TQDFWERLY—SEQ ID NO: 16

EXAMPLE 18

Polyclonal antibodies were raised in rabbits against the following peptides derived from the SNS sodium channel protein amino acid sequence:

Peptide 1 TQDSWER (SEQ ID NO:17)
Peptide 2 GSTDDNRSPQSDPYN (SEQ ID NO: 18)
Peptide 3 SPKENHGDFI (SEQ ID NO: 19)
Peptide 4 PNHNGSRGN (SEQ ID NO: 20)

The peptides were conjugated to Keyhole limpet heocyanin (KLH) and injected repeatedly into rabbits. Sera from the rabbits was treated by Western blotting. Several sera showed positive results indicating the presence of antibodies specific for the peptide in the sera.

REFERENCES

Catterall W. A. (1992) Physiol. Rev. 72, S4–S47.
Cohen S. A. and Barchi R. L. (1993) Int. Rev. Cytology 137c, 55–103.
Hodgkin A. L. and Huxley A. F. (1952) J. Physiol. 116, 473–496.
Hille B. (1991) Ionic channels in excitable membranes (Sinauer Sunderland Mass.)
Jeftjina S. (1994) Brain Res. 639, 125–134.
Kohler G. and Milstein C. (1976) Eur J. Immunol 6, 511–519
Lewin B. (1995) Genes V Oxford University Press, Oxford.
Melton D. et al. (1984) Nucleic Acids Res. 12, 7035
Nowycky M. (1993) in Sensory Neurons (Ed Scott S.) OUP, Oxford.
Omri G. and Meir H. (1990) J. Membrane Biol. 115, 13–29
Pearce R. J. and Duchen M. R. (1994) Neuroscience 63, 1041–1056
Pfaff S L; Tamkun-M M; Taylor-W L (1990 Anal-Biochem. 1990 188 192–195
Schaeren-Wimers N. and Gerfin-Moser A. (1993) Histochemistry 100, 431–440.
Smith D. B. and Johnson K. S. (1988) Gene 67, 31–40.

---

SEQUENCE LISTING (1) GENERAL INFORMATION:

(iii) NUMBER OF SEQUENCES: 31

(2) INFORMATION FOR SEQ ID NO:1:

(i) SEQUENCE CHARACTERISTICS:
        (A) LENGTH: 6524 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 204..6077

(xi) SEQUENCE DESCRIPTION: SEQ ID NO:1:

```
TAGCTTGCTT CTGCTAATGC TACCCCAGGC CTTTAGACAG AGAACAGATG GCAGATGGAG        60

TTTCTTATTG CCATGCGCAA ACGCTGAGCC CACCTCATGA TCCCGGACCC CATGGTTTTC       120

AGTAGACAAC CTGGGCTAAG AAGAGATCTC CGACCTTATA GAGCAGCAAA GAGTGTAAAT       180

TCTTCCCCAA GAAGAATGAG AAG ATG GAG CTC CCC TTT GCG TCC GTG GGA          230
                          Met Glu Leu Pro Phe Ala Ser Val Gly
                            1               5

ACT ACC AAT TTC AGA CGG TTC ACT CCA GAG TCA CTG GCA GAG ATC GAG        278
Thr Thr Asn Phe Arg Arg Phe Thr Pro Glu Ser Leu Ala Glu Ile Glu
 10              15                  20                  25

AAG CAG ATT GCT GCT CAC CGC GCA GCC AAG AAG GCC AGA ACC AAG CAC        326
Lys Gln Ile Ala Ala His Arg Ala Ala Lys Lys Ala Arg Thr Lys His
                 30                  35                  40

AGA GGA CAG GAG GAC AAG GGC GAG AAG CCC AGG CCT CAG CTG GAC TTG        374
Arg Gly Gln Glu Asp Lys Gly Glu Lys Pro Arg Pro Gln Leu Asp Leu
             45                  50                  55

AAA GAC TGT AAC CAG CTG CCC AAG TTC TAT GGT GAG CTC CCA GCA GAA        422
Lys Asp Cys Asn Gln Leu Pro Lys Phe Tyr Gly Glu Leu Pro Ala Glu
         60                  65                  70

CTG GTC GGG GAG CCC CTG GAG GAC CTA GAC CCT TTC TAC AGC ACA CAC        470
Leu Val Gly Glu Pro Leu Glu Asp Leu Asp Pro Phe Tyr Ser Thr His
     75                  80                  85

CGG ACA TTC ATG GTG TTG AAT AAA AGC AGG ACC ATT TCC AGA TTC AGT        518
Arg Thr Phe Met Val Leu Asn Lys Ser Arg Thr Ile Ser Arg Phe Ser
 90                  95                 100                 105

GCC ACT TGG GCC CTG TGG CTC TTC AGT CCC TTC AAC CTG ATC AGA AGA        566
Ala Thr Trp Ala Leu Trp Leu Phe Ser Pro Phe Asn Leu Ile Arg Arg
                110                 115                 120

ACA GCC ATC AAA GTG TCT GTC CAT TCC TGG TTC TCC ATA TTC ATC ACC        614
Thr Ala Ile Lys Val Ser Val His Ser Trp Phe Ser Ile Phe Ile Thr
            125                 130                 135

ATC ACT ATT TTG GTC AAC TGC GTG TGC ATG ACC CGA ACT GAT CTT CCA        662
Ile Thr Ile Leu Val Asn Cys Val Cys Met Thr Arg Thr Asp Leu Pro
        140                 145                 150

GAG AAA GTC GAG TAC GTC TTC ACT GTC ATT TAC ACC TTC GAG GCT CTG        710
Glu Lys Val Glu Tyr Val Phe Thr Val Ile Tyr Thr Phe Glu Ala Leu
    155                 160                 165

ATT AAG ATA CTG GCA AGA GGG TTT TGT CTA AAT GAG TTC ACT TAT CTT        758
Ile Lys Ile Leu Ala Arg Gly Phe Cys Leu Asn Glu Phe Thr Tyr Leu
170                 175                 180                 185

CGA GAT CCG TGG AAC TGG CTG GAC TTC AGT GTC ATT ACC TTG GCG TAT        806
Arg Asp Pro Trp Asn Trp Leu Asp Phe Ser Val Ile Thr Leu Ala Tyr
                190                 195                 200

GTG GGT GCA GCG ATA GAC CTC CGA GGA ATC TCA GGC CTG CGG ACA TTC        854
Val Gly Ala Ala Ile Asp Leu Arg Gly Ile Ser Gly Leu Arg Thr Phe
            205                 210                 215

CGA GTT CTC AGA GCC CTG AAA ACT GTT TCT GTG ATC CCA GGA CTG AAG        902
Arg Val Leu Arg Ala Leu Lys Thr Val Ser Val Ile Pro Gly Leu Lys
        220                 225                 230

GTC ATC GTG GGA GCC CTG ATC CAC TCA GTG AGG AAG CTG GCC GAC GTG        950
Val Ile Val Gly Ala Leu Ile His Ser Val Arg Lys Leu Ala Asp Val
    235                 240                 245

ACT ATC CTC ACA GTC TTC TGC CTG AGC GTC TTC GCC TTG GTG GGC CTG        998
Thr Ile Leu Thr Val Phe Cys Leu Ser Val Phe Ala Leu Val Gly Leu
250                 255                 260                 265

CAG CTC TTT AAG GGG AAC CTT AAG AAC AAA TGC ATC AGG AAC GGA ACA       1046
Gln Leu Phe Lys Gly Asn Leu Lys Asn Lys Cys Ile Arg Asn Gly Thr
                270                 275                 280
```

```
GAT CCC CAC AAG GCT GAC AAC CTC TCA TCT GAA ATG GCA GAA TAC GTC      1094
Asp Pro His Lys Ala Asp Asn Leu Ser Ser Glu Met Ala Glu Tyr Val
            285                 290                 295

TCC ATC AAG CCT GGT ACT ACG GAT CCC TTA CTG TGC GGC AAT GGG TCT      1142
Ser Ile Lys Pro Gly Thr Thr Asp Pro Leu Leu Cys Gly Asn Gly Ser
        300                 305                 310

GAT GCT GGT CAC TGC CCT GGA GGC TAT GTC TGC CTG AAA ACT CCT GAC      1190
Asp Ala Gly His Cys Pro Gly Gly Tyr Val Cys Leu Lys Thr Pro Asp
            315                 320                 325

AAC CCG GAT TTT AAC TAC ACC AGC TTT GAT TCC TTT GCG TGG GCA TTC      1238
Asn Pro Asp Phe Asn Tyr Thr Ser Phe Asp Ser Phe Ala Trp Ala Phe
330                 335                 340                 345

CTC TCA CTG TTC CGC CTC ATG ACG CAG GAC TCC TGG GAG CGC CTG TAC      1286
Leu Ser Leu Phe Arg Leu Met Thr Gln Asp Ser Trp Glu Arg Leu Tyr
            350                 355                 360

CAG CAG ACA CTC CGG GCT TCT GGG AAA ATG TAC ATG GTC TTT TTC GTG      1334
Gln Gln Thr Leu Arg Ala Ser Gly Lys Met Tyr Met Val Phe Phe Val
            365                 370                 375

CTG GTT ATT TTC CTT GGA TCG TTC TAC CTG GTC AAT TTG ATC TTG GCC      1382
Leu Val Ile Phe Leu Gly Ser Phe Tyr Leu Val Asn Leu Ile Leu Ala
            380                 385                 390

GTG GTC ACC ATG GCG TAT GAA GAG CAG AGC CAG GCA ACA ATT GCA GAA      1430
Val Val Thr Met Ala Tyr Glu Glu Gln Ser Gln Ala Thr Ile Ala Glu
        395                 400                 405

ATC GAA GCC AAG GAA AAA AAG TTC CAG GAA GCC CTT GAG GTG CTG CAG      1478
Ile Glu Ala Lys Glu Lys Lys Phe Gln Glu Ala Leu Glu Val Leu Gln
410                 415                 420                 425

AAG GAA CAG GAG GTG CTG GCA GCC CTG GGG ATT GAC ACG ACC TCG CTC      1526
Lys Glu Gln Glu Val Leu Ala Ala Leu Gly Ile Asp Thr Thr Ser Leu
            430                 435                 440

CAG TCC CAC AGT GGA TCA CCC TTA GCC TCC AAA AAC GCC AAT GAG AGA      1574
Gln Ser His Ser Gly Ser Pro Leu Ala Ser Lys Asn Ala Asn Glu Arg
            445                 450                 455

AGA CCC AGG GTG AAA TCA AGG GTG TCA GAG GGC TCC ACG GAT GAC AAC      1622
Arg Pro Arg Val Lys Ser Arg Val Ser Glu Gly Ser Thr Asp Asp Asn
            460                 465                 470

AGG TCA CCC CAA TCT GAC CCT TAC AAC CAG CGC AGG ATG TCT TTC CTA      1670
Arg Ser Pro Gln Ser Asp Pro Tyr Asn Gln Arg Arg Met Ser Phe Leu
475                 480                 485

GGC CTG TCT TCA GGA AGA CGC AGG GCT AGC CAC GGC AGT GTG TTC CAC      1718
Gly Leu Ser Ser Gly Arg Arg Arg Ala Ser His Gly Ser Val Phe His
490                 495                 500                 505

TTC CGA GCG CCC AGC CAA GAC ATC TCA TTT CCT GAC GGG ATC ACC CCT      1766
Phe Arg Ala Pro Ser Gln Asp Ile Ser Phe Pro Asp Gly Ile Thr Pro
            510                 515                 520

GAT GAT GGG GTC TTT CAC GGA GAC CAG GAA AGC CGT CGA GGT TCC ATA      1814
Asp Asp Gly Val Phe His Gly Asp Gln Glu Ser Arg Arg Gly Ser Ile
            525                 530                 535

TTG CTG GGC AGG GGT GCT GGG CAG ACA GGT CCA CTC CCC AGG AGC CCA      1862
Leu Leu Gly Arg Gly Ala Gly Gln Thr Gly Pro Leu Pro Arg Ser Pro
            540                 545                 550

CTG CCT CAG TCC CCC AAC CCT GGC CGT AGA CAT GGA GAA GAG GGA CAG      1910
Leu Pro Gln Ser Pro Asn Pro Gly Arg Arg His Gly Glu Glu Gly Gln
555                 560                 565

CTC GGA GTG CCC ACT GGT GAG CTT ACC GCT GGA GCG CCT GAA GGC CCG      1958
Leu Gly Val Pro Thr Gly Glu Leu Thr Ala Gly Ala Pro Glu Gly Pro
570                 575                 580                 585

GCA CTG CAC ACT ACA GGG CAG AAG AGC TTC CTG TCT GCG GGC TAC TTG      2006
Ala Leu His Thr Thr Gly Gln Lys Ser Phe Leu Ser Ala Gly Tyr Leu
```

-continued

```
                      590                      595                      600
AAC GAA CCT TTC CGA GCA CAG AGG GCC ATG AGC GTT GTC AGT ATC ATG            2054
Asn Glu Pro Phe Arg Ala Gln Arg Ala Met Ser Val Val Ser Ile Met
            605                     610                     615

ACT TCT GTC ATT GAG GAG CTT GAA GAG TCT AAG CTG AAG TGC CCA CCC            2102
Thr Ser Val Ile Glu Glu Leu Glu Glu Ser Lys Leu Lys Cys Pro Pro
            620                     625                     630

TGC TTG ATC AGC TTC GCT CAG AAG TAT CTG ATC TGG GAG TGC TGC CCC            2150
Cys Leu Ile Ser Phe Ala Gln Lys Tyr Leu Ile Trp Glu Cys Cys Pro
            635                     640                     645

AAG TGG AGG AAG TTC AAG ATG GCG CTG TTC GAG CTG GTG ACT GAC CCC            2198
Lys Trp Arg Lys Phe Lys Met Ala Leu Phe Glu Leu Val Thr Asp Pro
650                     655                     660                     665

TTC GCA GAG CTT ACC ATC ACC CTC TGC ATC GTG GTG AAC ACC GTC TTC            2246
Phe Ala Glu Leu Thr Ile Thr Leu Cys Ile Val Val Asn Thr Val Phe
                        670                     675                     680

ATG GCC ATG GAG CAC TAC CCC ATG ACC GAT GCC TTC GAT GCC ATG CTT            2294
Met Ala Met Glu His Tyr Pro Met Thr Asp Ala Phe Asp Ala Met Leu
            685                     690                     695

CAA GCC GGC AAC ATT GTC TTC ACC GTG TTT TTC ACA ATG GAG ATG GCC            2342
Gln Ala Gly Asn Ile Val Phe Thr Val Phe Phe Thr Met Glu Met Ala
            700                     705                     710

TTC AAG ATC ATT GCC TTC GAC CCC TAC TAT TAC TTC CAG AAG AAG TGG            2390
Phe Lys Ile Ile Ala Phe Asp Pro Tyr Tyr Tyr Phe Gln Lys Lys Trp
            715                     720                     725

AAT ATC TTC GAC TGT GTC ATC GTC ACC GTG AGC CTT CTG GAG CTG AGT            2438
Asn Ile Phe Asp Cys Val Ile Val Thr Val Ser Leu Leu Glu Leu Ser
730                     735                     740                     745

GCA TCC AAG AAG GGC AGC CTG TCT GTG CTC CGT ACC TTA CGC TTG CTG            2486
Ala Ser Lys Lys Gly Ser Leu Ser Val Leu Arg Thr Leu Arg Leu Leu
                        750                     755                     760

CGG GTC TTC AAG CTG GCC AAG TCC TGG CCC ACC CTG AAC ACC CTC ATC            2534
Arg Val Phe Lys Leu Ala Lys Ser Trp Pro Thr Leu Asn Thr Leu Ile
            765                     770                     775

AAG ATC ATC GGG AAC TCA GTG GGG GCC CTG GGC AAC CTG ACC TTT ATC            2582
Lys Ile Ile Gly Asn Ser Val Gly Ala Leu Gly Asn Leu Thr Phe Ile
            780                     785                     790

CTG GCC ATC ATC GTC TTC ATC TTC GCC CTG GTC GGA AAG CAG CTT CTC            2630
Leu Ala Ile Ile Val Phe Ile Phe Ala Leu Val Gly Lys Gln Leu Leu
            795                     800                     805

TCA GAG GAC TAC GGG TGC CGC AAG GAC GGC GTC TCC GTG TGG AAC GGC            2678
Ser Glu Asp Tyr Gly Cys Arg Lys Asp Gly Val Ser Val Trp Asn Gly
810                     815                     820                     825

GAG AAG CTC CGC TGG CAC ATG TGT GAC TTC TTC CAT TCC TTC CTG GTC            2726
Glu Lys Leu Arg Trp His Met Cys Asp Phe Phe His Ser Phe Leu Val
                        830                     835                     840

GTC TTC CGA ATC CTC TGC GGG GAG TGG ATC GAG AAC ATG TGG GTC TGC            2774
Val Phe Arg Ile Leu Cys Gly Glu Trp Ile Glu Asn Met Trp Val Cys
            845                     850                     855

ATG GAG GTC AGC CAG AAA TCC ATC TGC CTC ATC CTC TTC TTG ACT GTG            2822
Met Glu Val Ser Gln Lys Ser Ile Cys Leu Ile Leu Phe Leu Thr Val
            860                     865                     870

ATG GTG CTG GGC AAC CTA GTG GTG CTC AAC CTT TTC ATC GCT TTA CTG            2870
Met Val Leu Gly Asn Leu Val Val Leu Asn Leu Phe Ile Ala Leu Leu
            875                     880                     885

CTG AAC TCC TTC AGC GCG GAC AAC CTC ACG GCT CCA GAG GAT GAC GGG            2918
Leu Asn Ser Phe Ser Ala Asp Asn Leu Thr Ala Pro Glu Asp Asp Gly
890                     895                     900                     905

GAG GTG AAC AAC TTG CAG TTA GCA CTG GCC AGG ATC CAG GTA CTT GGC            2966
```

```
                    Glu Val Asn Asn Leu Gln Leu Ala Leu Ala Arg Ile Gln Val Leu Gly
                                    910                 915                 920

CAT CGG GCC AGC AGG GCC AGC GCC AGT TAC ATC AGC AGC CAC TGC CGA              3014
His Arg Ala Ser Arg Ala Ser Ala Ser Tyr Ile Ser Ser His Cys Arg
                925                 930                 935

TTC CAC TGG CCC AAG GTG GAG ACC CAG CTG GGC ATG AAG CCC CCA CTC              3062
Phe His Trp Pro Lys Val Glu Thr Gln Leu Gly Met Lys Pro Pro Leu
            940                 945                 950

ACC AGC TCA GAG GCC AAG AAC CAC ATT GCC ACT GAT GCT GTC AGT GCT              3110
Thr Ser Ser Glu Ala Lys Asn His Ile Ala Thr Asp Ala Val Ser Ala
        955                 960                 965

GCA GTG GGG AAC CTG ACA AAG CCA GCT CTC AGT AGC CCC AAG GAG AAC              3158
Ala Val Gly Asn Leu Thr Lys Pro Ala Leu Ser Ser Pro Lys Glu Asn
970                 975                 980                 985

CAC GGG GAC TTC ATC ACT GAT CCC AAC GTG TGG GTC TCT GTG CCC ATT              3206
His Gly Asp Phe Ile Thr Asp Pro Asn Val Trp Val Ser Val Pro Ile
                990                 995                 1000

GCT GAG GGG GAA TCT GAC CTC GAC GAG CTC GAG GAA GAT ATG GAG CAG              3254
Ala Glu Gly Glu Ser Asp Leu Asp Glu Leu Glu Glu Asp Met Glu Gln
                1005                1010                1015

GCT TCG CAG AGC TCC TGG CAG GAA GAG GAC CCC AAG GGA CAG CAG GAG              3302
Ala Ser Gln Ser Ser Trp Gln Glu Glu Asp Pro Lys Gly Gln Gln Glu
            1020                1025                1030

CAG TTG CCA CAA GTC CAA AAG TGT GAA AAC CAC CAG GCA GCC AGA AGC              3350
Gln Leu Pro Gln Val Gln Lys Cys Glu Asn His Gln Ala Ala Arg Ser
        1035                1040                1045

CCA GCC TCC ATG ATG TCC TCT GAG GAC CTG GCT CCA TAC CTG GGT GAG              3398
Pro Ala Ser Met Met Ser Ser Glu Asp Leu Ala Pro Tyr Leu Gly Glu
1050                1055                1060                1065

AGC TGG AAG AGG AAG GAT AGC CCT CAG GTC CCT GCC GAG GGA GTG GAT              3446
Ser Trp Lys Arg Lys Asp Ser Pro Gln Val Pro Ala Glu Gly Val Asp
                1070                1075                1080

GAC ACG AGC TCC TCT GAG GGC AGC ACG GTG GAC TGC CCG GAC CCA GAG              3494
Asp Thr Ser Ser Ser Glu Gly Ser Thr Val Asp Cys Pro Asp Pro Glu
                1085                1090                1095

GAA ATC CTG AGG AAG ATC CCC GAG CTG GCA CAT GAC CTG GAC GAG CCC              3542
Glu Ile Leu Arg Lys Ile Pro Glu Leu Ala His Asp Leu Asp Glu Pro
            1100                1105                1110

GAT GAC TGT TTC AGA GAA GGC TGC ACT CGC CGC TGT CCC TGC TGC AAC              3590
Asp Asp Cys Phe Arg Glu Gly Cys Thr Arg Arg Cys Pro Cys Cys Asn
        1115                1120                1125

GTG AAT ACT AGC AAG TCT CCT TGG GCC ACA GGC TGG CAG GTG CGC AAG              3638
Val Asn Thr Ser Lys Ser Pro Trp Ala Thr Gly Trp Gln Val Arg Lys
1130                1135                1140                1145

ACC TGC TAC CGC ATC GTG GAG CAC AGC TGG TTT GAG AGT TTC ATC ATC              3686
Thr Cys Tyr Arg Ile Val Glu His Ser Trp Phe Glu Ser Phe Ile Ile
                1150                1155                1160

TTC ATG ATC CTG CTC AGC AGT GGA GCG CTG GCC TTT GAG GAT AAC TAC              3734
Phe Met Ile Leu Leu Ser Ser Gly Ala Leu Ala Phe Glu Asp Asn Tyr
                1165                1170                1175

CTG GAA GAG AAA CCC CGA GTG AAG TCC GTG CTG GAG TAC ACT GAC CGA              3782
Leu Glu Glu Lys Pro Arg Val Lys Ser Val Leu Glu Tyr Thr Asp Arg
            1180                1185                1190

GTG TTC ACC TTC ATC TTC GTC TTT GAG ATG CTG CTC AAG TGG GTA GCC              3830
Val Phe Thr Phe Ile Phe Val Phe Glu Met Leu Leu Lys Trp Val Ala
        1195                1200                1205

TAT GGC TTC AAA AAG TAT TTC ACC AAT GCC TGG TGC TGG CTG GAC TTC              3878
Tyr Gly Phe Lys Lys Tyr Phe Thr Asn Ala Trp Cys Trp Leu Asp Phe
1210                1215                1220                1225
```

```
CTC ATT GTG AAC ATC TCC CTG ACA AGC CTC ATA GCG AAG ATC CTT GAG          3926
Leu Ile Val Asn Ile Ser Leu Thr Ser Leu Ile Ala Lys Ile Leu Glu
            1230                1235                1240

TAT TCC GAC GTG GCG TCC ATC AAA GCC CTT CGG ACT CTC CGT GCC CTC          3974
Tyr Ser Asp Val Ala Ser Ile Lys Ala Leu Arg Thr Leu Arg Ala Leu
            1245                1250                1255

CGA CCG CTG CGG GCT CTG TCT CGA TTC GAA GGC ATG AGG GTA GTG GTG          4022
Arg Pro Leu Arg Ala Leu Ser Arg Phe Glu Gly Met Arg Val Val Val
            1260                1265                1270

GAT GCC CTC GTG GGC GCC ATC CCC TCC ATC ATG AAC GTC CTC CTC GTC          4070
Asp Ala Leu Val Gly Ala Ile Pro Ser Ile Met Asn Val Leu Leu Val
            1275                1280                1285

TGC CTC ATC TTC TGG CTC ATC TTC AGC ATC ATG GGC GTG AAC CTC TTC          4118
Cys Leu Ile Phe Trp Leu Ile Phe Ser Ile Met Gly Val Asn Leu Phe
1290                1295                1300                1305

GCC GGG AAA TTT TCG AAG TGC GTC GAC ACC AGA AAT AAC CCA TTT TCC          4166
Ala Gly Lys Phe Ser Lys Cys Val Asp Thr Arg Asn Asn Pro Phe Ser
            1310                1315                1320

AAC GTG AAT TCG ACG ATG GTG AAT AAC AAG TCC GAG TGT CAC AAT CAA          4214
Asn Val Asn Ser Thr Met Val Asn Asn Lys Ser Glu Cys His Asn Gln
            1325                1330                1335

AAC AGC ACC GGC CAC TTC TTC TGG GTC AAC GTC AAA GTC AAC TTC GAC          4262
Asn Ser Thr Gly His Phe Phe Trp Val Asn Val Lys Val Asn Phe Asp
            1340                1345                1350

AAC GTC GCT ATG GGC TAC CTC GCA CTT CTT CAG GTG GCA ACC TTC AAA          4310
Asn Val Ala Met Gly Tyr Leu Ala Leu Leu Gln Val Ala Thr Phe Lys
            1355                1360                1365

GGC TGG ATG GAC ATA ATG TAT GCA GCT GTT GAT TCC GGA GAG ATC AAC          4358
Gly Trp Met Asp Ile Met Tyr Ala Ala Val Asp Ser Gly Glu Ile Asn
1370                1375                1380                1385

AGT CAG CCT AAC TGG GAG AAC AAC TTG TAC ATG TAC CTG TAC TTC GTC          4406
Ser Gln Pro Asn Trp Glu Asn Asn Leu Tyr Met Tyr Leu Tyr Phe Val
            1390                1395                1400

GTT TTC ATC ATT TTC GGT GGC TTC TTC ACG CTG AAT CTC TTT GTT GGG          4454
Val Phe Ile Ile Phe Gly Gly Phe Phe Thr Leu Asn Leu Phe Val Gly
            1405                1410                1415

GTC ATA ATC GAC AAC TTC AAC CAA CAG AAA AAA AAG CTA GGA GGC CAG          4502
Val Ile Ile Asp Asn Phe Asn Gln Gln Lys Lys Lys Leu Gly Gly Gln
            1420                1425                1430

GAC ATC TTC ATG ACA GAA GAG CAG AAG AAG TAC TAC AAT GCC ATG AAG          4550
Asp Ile Phe Met Thr Glu Glu Gln Lys Lys Tyr Tyr Asn Ala Met Lys
            1435                1440                1445

AAG CTG GGC TCC AAG AAA CCC CAG AAG CCC ATC CCA CGG CCC CTG AAT          4598
Lys Leu Gly Ser Lys Lys Pro Gln Lys Pro Ile Pro Arg Pro Leu Asn
1450                1455                1460                1465

AAG TAC CAA GGC TTC GTG TTT GAC ATC GTG ACC AGG CAA GCC TTT GAC          4646
Lys Tyr Gln Gly Phe Val Phe Asp Ile Val Thr Arg Gln Ala Phe Asp
            1470                1475                1480

ATC ATC ATC ATG GTT CTC ATC TGC CTC AAC ATG ATC ACC ATG ATG GTG          4694
Ile Ile Ile Met Val Leu Ile Cys Leu Asn Met Ile Thr Met Met Val
            1485                1490                1495

GAG ACC GAC GAG CAG GGC GAG GAG AAG ACG AAG GTT CTG GGC AGA ATC          4742
Glu Thr Asp Glu Gln Gly Glu Glu Lys Thr Lys Val Leu Gly Arg Ile
            1500                1505                1510

AAC CAG TTC TTT GTG GCC GTC TTC ACG GGC GAG TGT GTG ATG AAG ATG          4790
Asn Gln Phe Phe Val Ala Val Phe Thr Gly Glu Cys Val Met Lys Met
            1515                1520                1525

TTC GCC CTG CGA CAG TAC TAC TTC ACC AAC GGC TGG AAC GTG TTC GAC          4838
Phe Ala Leu Arg Gln Tyr Tyr Phe Thr Asn Gly Trp Asn Val Phe Asp
1530                1535                1540                1545
```

```
TTC ATA GTG GTG ATC CTG TCC ATT GGG AGT CTG CTG TTT TCT GCA ATC      4886
Phe Ile Val Val Ile Leu Ser Ile Gly Ser Leu Leu Phe Ser Ala Ile
                1550                1555                1560

CTT AAG TCA CTG GAA AAC TAC TTC TCC CCG ACG CTC TTC CGG GTC ATC      4934
Leu Lys Ser Leu Glu Asn Tyr Phe Ser Pro Thr Leu Phe Arg Val Ile
                1565                1570                1575

CGT CTG GCC AGG ATC GGC CGC ATC CTC AGG CTG ATC CGA GCA GCC AAG      4982
Arg Leu Ala Arg Ile Gly Arg Ile Leu Arg Leu Ile Arg Ala Ala Lys
                1580                1585                1590

GGG ATT CGC ACG CTG CTC TTC GCC CTC ATG ATG TCC CTG CCC GCC CTC      5030
Gly Ile Arg Thr Leu Leu Phe Ala Leu Met Met Ser Leu Pro Ala Leu
                1595                1600                1605

TTC AAC ATC GGC CTC CTC CTC TTC CTC GTC ATG TTC ATC TAC TCC ATC      5078
Phe Asn Ile Gly Leu Leu Leu Phe Leu Val Met Phe Ile Tyr Ser Ile
1610                1615                1620                1625

TTC GGC ATG GCC AGC TTC GCT AAC GTC GTG GAC GAG GCC GGC ATC GAC      5126
Phe Gly Met Ala Ser Phe Ala Asn Val Val Asp Glu Ala Gly Ile Asp
                1630                1635                1640

GAC ATG TTC AAC TTC AAG ACC TTT GGC AAC AGC ATG CTG TGC CTG TTC      5174
Asp Met Phe Asn Phe Lys Thr Phe Gly Asn Ser Met Leu Cys Leu Phe
                1645                1650                1655

CAG ATC ACC ACC TCG GCC GGC TGG GAC GGC CTC CTC AGC CCC ATC CTC      5222
Gln Ile Thr Thr Ser Ala Gly Trp Asp Gly Leu Leu Ser Pro Ile Leu
                1660                1665                1670

AAC ACG GGG CCT CCC TAC TGC GAC CCC AAC CTG CCC AAC AGC AAC GGC      5270
Asn Thr Gly Pro Pro Tyr Cys Asp Pro Asn Leu Pro Asn Ser Asn Gly
                1675                1680                1685

TCC CGG GGG AAC TGC GGG AGC CCG GCG GTG GGC ATC ATC TTC TTC ACC      5318
Ser Arg Gly Asn Cys Gly Ser Pro Ala Val Gly Ile Ile Phe Phe Thr
1690                1695                1700                1705

ACC TAC ATC ATC ATC TCC TTC CTC ATC GTG GTC AAC ATG TAC ATC GCA      5366
Thr Tyr Ile Ile Ile Ser Phe Leu Ile Val Val Asn Met Tyr Ile Ala
                1710                1715                1720

GTG ATT CTG GAG AAC TTC AAC GTA GCC ACC GAG GAG AGC ACG GAG CCC      5414
Val Ile Leu Glu Asn Phe Asn Val Ala Thr Glu Glu Ser Thr Glu Pro
                1725                1730                1735

CTG AGC GAG GAC GAC TTC GAC ATG TTC TAT GAG ACC TGG GAG AAG TTC      5462
Leu Ser Glu Asp Asp Phe Asp Met Phe Tyr Glu Thr Trp Glu Lys Phe
                1740                1745                1750

GAC CCG GAG GCC ACC CAG TTC ATT GCC TTT TCT GCC CTC TCA GAC TTC      5510
Asp Pro Glu Ala Thr Gln Phe Ile Ala Phe Ser Ala Leu Ser Asp Phe
                1755                1760                1765

GCG GAC ACG CTC TCC GGC CCT CTT AGA ATC CCC AAA CCC AAC CAG AAT      5558
Ala Asp Thr Leu Ser Gly Pro Leu Arg Ile Pro Lys Pro Asn Gln Asn
1770                1775                1780                1785

ATA TTA ATC CAG ATG GAC CTG CCG TTG GTC CCC GGG GAT AAG ATC CAC      5606
Ile Leu Ile Gln Met Asp Leu Pro Leu Val Pro Gly Asp Lys Ile His
                1790                1795                1800

TGT CTG GAC ATC CTT TTT GCC TTC ACA AAG AAC GTC TTG GGA GAA TCC      5654
Cys Leu Asp Ile Leu Phe Ala Phe Thr Lys Asn Val Leu Gly Glu Ser
                1805                1810                1815

GGG GAG TTG GAC TCC CTG AAG ACC AAT ATG GAA GAG AAG TTT ATG GCG      5702
Gly Glu Leu Asp Ser Leu Lys Thr Asn Met Glu Glu Lys Phe Met Ala
                1820                1825                1830

ACC AAT CTC TCC AAA GCA TCC TAT GAA CCA ATA GCC ACC ACC CTC CGG      5750
Thr Asn Leu Ser Lys Ala Ser Tyr Glu Pro Ile Ala Thr Thr Leu Arg
                1835                1840                1845

TGG AAG CAG GAA GAC CTC TCA GCC ACA GTC ATT CAA AAG GCC TAC CGG      5798
Trp Lys Gln Glu Asp Leu Ser Ala Thr Val Ile Gln Lys Ala Tyr Arg
```

|  |  |  |  |  |  |  |  |  |  |  |  |  |  |  |  |
|---|---|---|---|---|---|---|---|---|---|---|---|---|---|---|---|
| AGC | TAC | ATG | CTG | CAC | CGC | TCC | TTG | ACA | CTC | TCC | AAC | ACC | CTG | CAT | GTG | 5846 |
| Ser | Tyr | Met | Leu | His | Arg | Ser | Leu | Thr | Leu | Ser | Asn | Thr | Leu | His | Val |
|  |  |  | 1870 |  |  |  | 1875 |  |  |  |  | 1880 |

```
AGC TAC ATG CTG CAC CGC TCC TTG ACA CTC TCC AAC ACC CTG CAT GTG    5846
Ser Tyr Met Leu His Arg Ser Leu Thr Leu Ser Asn Thr Leu His Val
            1870                1875                1880

CCC AGG GCT GAG GAG GAT GGC GTG TCA CTT CCC GGG GAA GGC TAC ATT    5894
Pro Arg Ala Glu Glu Asp Gly Val Ser Leu Pro Gly Glu Gly Tyr Ile
            1885                1890                1895

ACA TTC ATG GCA AAC AGT GGA CTC CCG GAC AAA TCA GAA ACT GCC TCT    5942
Thr Phe Met Ala Asn Ser Gly Leu Pro Asp Lys Ser Glu Thr Ala Ser
            1900                1905                1910

GCT ACG TCT TTC CCG CCA TCC TAT GAC AGT GTC ACC AGG GGC CTG AGT    5990
Ala Thr Ser Phe Pro Pro Ser Tyr Asp Ser Val Thr Arg Gly Leu Ser
            1915                1920                1925

GAC CGG GCC AAC ATT AAC CCA TCT AGC TCA ATG CAA AAT GAA GAT GAG    6038
Asp Arg Ala Asn Ile Asn Pro Ser Ser Ser Met Gln Asn Glu Asp Glu
1930            1935                1940                1945

GTC GCT GCT AAG GAA GGA AAC AGC CCT GGA CCT CAG  TGAAGGCACT         6084
Val Ala Ala Lys Glu Gly Asn Ser Pro Gly Pro Gln
            1950                1955

CAGGCATGCA CAGGGCAGGT TCCAATGTCT TTCTCTGCTG TACTAACTCC TTCCCTCTGG   6144

AGGTGGCACC AACCTCCAGC CTCCACCAAT GCATGTCACT GGTCATGGTG TCAGAACTGA   6204

ATGGGGACAT CCTTGAGAAA GCCCCCACCC AATAGGAAT  CAAAAGCCAA GGATACTCCT   6264

CCATTCTGAC GTCCCTTCCG AGTTCCCAGA AGATGTCATT GCTCCCTTCT GTTTGTGACC   6324

AGAGACGTGA TTCACCAACT TCTCGGAGCC AGAGACACAT AGCAAAGACT TTTCTGCTGG   6384

TGTCGGGCAG TCTTAGAGAA GTCACGTAGG GGTTGGTACT GAGAATTAGG GTTTGCATGA   6444

CTGCATGCTC ACAGCTGCCG GACAATACCT GTGAGTCGGC CATTAAAATT AATATTTTTA   6504

AAGTTAAAAA AAAAAAAAA                                                6524

(2) INFORMATION FOR SEQ ID NO:2:

(i) SEQUENCE CHARACTERISTICS:
        (A) LENGTH: 1957 amino acids
        (B) TYPE: amino acid
        (D) TOPOLOGY: linear (ii) MOLECULE TYPE: protein (xi) SEQUENCE DESCRIPTION: SEQ ID NO:2:

Met Glu Leu Pro Phe Ala Ser Val Gly Thr Thr Asn Phe Arg Arg Phe
  1               5                  10                  15

Thr Pro Glu Ser Leu Ala Glu Ile Glu Lys Gln Ile Ala Ala His Arg
             20                  25                  30

Ala Ala Lys Lys Ala Arg Thr Lys His Arg Gly Gln Glu Asp Lys Gly
         35                  40                  45

Glu Lys Pro Arg Pro Gln Leu Asp Leu Lys Asp Cys Asn Gln Leu Pro
     50                  55                  60

Lys Phe Tyr Gly Glu Leu Pro Ala Glu Leu Val Gly Glu Pro Leu Glu
 65                  70                  75                  80

Asp Leu Asp Pro Phe Tyr Ser Thr His Arg Thr Phe Met Val Leu Asn
                 85                  90                  95

Lys Ser Arg Thr Ile Ser Arg Phe Ser Ala Thr Trp Ala Leu Trp Leu
            100                 105                 110

Phe Ser Pro Phe Asn Leu Ile Arg Arg Thr Ala Ile Lys Val Ser Val
        115                 120                 125

His Ser Trp Phe Ser Ile Phe Ile Thr Ile Thr Ile Leu Val Asn Cys
```

```
                130                 135                 140
Val Cys Met Thr Arg Thr Asp Leu Pro Glu Lys Val Glu Tyr Val Phe
145                 150                 155                 160

Thr Val Ile Tyr Thr Phe Glu Ala Leu Ile Lys Ile Leu Ala Arg Gly
                165                 170                 175

Phe Cys Leu Asn Glu Phe Thr Tyr Leu Arg Asp Pro Trp Asn Trp Leu
                180                 185                 190

Asp Phe Ser Val Ile Thr Leu Ala Tyr Val Gly Ala Ala Ile Asp Leu
                195                 200                 205

Arg Gly Ile Ser Gly Leu Arg Thr Phe Arg Val Leu Arg Ala Leu Lys
        210                 215                 220

Thr Val Ser Val Ile Pro Gly Leu Lys Val Ile Val Gly Ala Leu Ile
225                 230                 235                 240

His Ser Val Arg Lys Leu Ala Asp Val Thr Ile Leu Thr Val Phe Cys
                245                 250                 255

Leu Ser Val Phe Ala Leu Val Gly Leu Gln Leu Phe Lys Gly Asn Leu
                260                 265                 270

Lys Asn Lys Cys Ile Arg Asn Gly Thr Asp Pro His Lys Ala Asp Asn
        275                 280                 285

Leu Ser Ser Glu Met Ala Glu Tyr Val Ser Ile Lys Pro Gly Thr Thr
290                 295                 300

Asp Pro Leu Leu Cys Gly Asn Gly Ser Asp Ala Gly His Cys Pro Gly
305                 310                 315                 320

Gly Tyr Val Cys Leu Lys Thr Pro Asp Asn Pro Asp Phe Asn Tyr Thr
                325                 330                 335

Ser Phe Asp Ser Phe Ala Trp Ala Phe Leu Ser Leu Phe Arg Leu Met
                340                 345                 350

Thr Gln Asp Ser Trp Glu Arg Leu Tyr Gln Gln Thr Leu Arg Ala Ser
        355                 360                 365

Gly Lys Met Tyr Met Val Phe Phe Val Leu Val Ile Phe Leu Gly Ser
        370                 375                 380

Phe Tyr Leu Val Asn Leu Ile Leu Ala Val Val Thr Met Ala Tyr Glu
385                 390                 395                 400

Glu Gln Ser Gln Ala Thr Ile Ala Glu Ile Glu Ala Lys Glu Lys Lys
                405                 410                 415

Phe Gln Glu Ala Leu Glu Val Leu Gln Lys Glu Gln Glu Val Leu Ala
                420                 425                 430

Ala Leu Gly Ile Asp Thr Thr Ser Leu Gln Ser His Ser Gly Ser Pro
        435                 440                 445

Leu Ala Ser Lys Asn Ala Asn Glu Arg Arg Pro Arg Val Lys Ser Arg
450                 455                 460

Val Ser Glu Gly Ser Thr Asp Asp Asn Arg Ser Pro Gln Ser Asp Pro
465                 470                 475                 480

Tyr Asn Gln Arg Arg Met Ser Phe Leu Gly Leu Ser Ser Gly Arg Arg
                485                 490                 495

Arg Ala Ser His Gly Ser Val Phe His Phe Arg Ala Pro Ser Gln Asp
                500                 505                 510

Ile Ser Phe Pro Asp Gly Ile Thr Pro Asp Asp Gly Val Phe His Gly
        515                 520                 525

Asp Gln Glu Ser Arg Arg Gly Ser Ile Leu Leu Gly Arg Gly Ala Gly
        530                 535                 540

Gln Thr Gly Pro Leu Pro Arg Ser Pro Leu Pro Gln Ser Pro Asn Pro
545                 550                 555                 560
```

```
Gly Arg Arg His Gly Glu Glu Gly Gln Leu Gly Val Pro Thr Gly Glu
            565                 570                 575
Leu Thr Ala Gly Ala Pro Glu Gly Pro Ala Leu His Thr Thr Gly Gln
            580                 585                 590
Lys Ser Phe Leu Ser Ala Gly Tyr Leu Asn Glu Pro Phe Arg Ala Gln
            595                 600                 605
Arg Ala Met Ser Val Val Ser Ile Met Thr Ser Val Ile Glu Glu Leu
            610                 615                 620
Glu Glu Ser Lys Leu Lys Cys Pro Pro Cys Leu Ile Ser Phe Ala Gln
625                 630                 635                 640
Lys Tyr Leu Ile Trp Glu Cys Cys Pro Lys Trp Arg Lys Phe Lys Met
            645                 650                 655
Ala Leu Phe Glu Leu Val Thr Asp Pro Phe Ala Glu Leu Thr Ile Thr
            660                 665                 670
Leu Cys Ile Val Val Asn Thr Val Phe Met Ala Met Glu His Tyr Pro
            675                 680                 685
Met Thr Asp Ala Phe Asp Ala Met Leu Gln Ala Gly Asn Ile Val Phe
            690                 695                 700
Thr Val Phe Phe Thr Met Glu Met Ala Phe Lys Ile Ile Ala Phe Asp
705                 710                 715                 720
Pro Tyr Tyr Tyr Phe Gln Lys Lys Trp Asn Ile Phe Asp Cys Val Ile
            725                 730                 735
Val Thr Val Ser Leu Leu Glu Leu Ser Ala Ser Lys Lys Gly Ser Leu
            740                 745                 750
Ser Val Leu Arg Thr Leu Arg Leu Leu Arg Val Phe Lys Leu Ala Lys
            755                 760                 765
Ser Trp Pro Thr Leu Asn Thr Leu Ile Lys Ile Ile Gly Asn Ser Val
            770                 775                 780
Gly Ala Leu Gly Asn Leu Thr Phe Ile Leu Ala Ile Ile Val Phe Ile
785                 790                 795                 800
Phe Ala Leu Val Gly Lys Gln Leu Leu Ser Glu Asp Tyr Gly Cys Arg
            805                 810                 815
Lys Asp Gly Val Ser Val Trp Asn Gly Glu Lys Leu Arg Trp His Met
            820                 825                 830
Cys Asp Phe Phe His Ser Phe Leu Val Val Phe Arg Ile Leu Cys Gly
            835                 840                 845
Glu Trp Ile Glu Asn Met Trp Val Cys Met Glu Val Ser Gln Lys Ser
            850                 855                 860
Ile Cys Leu Ile Leu Phe Leu Thr Val Met Val Leu Gly Asn Leu Val
865                 870                 875                 880
Val Leu Asn Leu Phe Ile Ala Leu Leu Leu Asn Ser Phe Ser Ala Asp
            885                 890                 895
Asn Leu Thr Ala Pro Glu Asp Asp Gly Glu Val Asn Asn Leu Gln Leu
            900                 905                 910
Ala Leu Ala Arg Ile Gln Val Leu Gly His Arg Ala Ser Arg Ala Ser
            915                 920                 925
Ala Ser Tyr Ile Ser Ser His Cys Arg Phe His Trp Pro Lys Val Glu
            930                 935                 940
Thr Gln Leu Gly Met Lys Pro Pro Leu Thr Ser Ser Glu Ala Lys Asn
945                 950                 955                 960
His Ile Ala Thr Asp Ala Val Ser Ala Ala Val Gly Asn Leu Thr Lys
            965                 970                 975
```

-continued

```
Pro Ala Leu Ser Ser Pro Lys Glu Asn His Gly Asp Phe Ile Thr Asp
            980                 985                 990

Pro Asn Val Trp Val Ser Val Pro Ile Ala Glu Gly Glu Ser Asp Leu
            995                 1000                1005

Asp Glu Leu Glu Glu Asp Met Glu Gln Ala Ser Gln Ser Ser Trp Gln
        1010                1015                1020

Glu Glu Asp Pro Lys Gly Gln Gln Glu Gln Leu Pro Gln Val Gln Lys
1025                1030                1035                1040

Cys Glu Asn His Gln Ala Ala Arg Ser Pro Ala Ser Met Met Ser Ser
                1045                1050                1055

Glu Asp Leu Ala Pro Tyr Leu Gly Glu Ser Trp Lys Arg Lys Asp Ser
            1060                1065                1070

Pro Gln Val Pro Ala Glu Gly Val Asp Asp Thr Ser Ser Ser Glu Gly
            1075                1080                1085

Ser Thr Val Asp Cys Pro Asp Pro Glu Glu Ile Leu Arg Lys Ile Pro
            1090                1095                1100

Glu Leu Ala His Asp Leu Asp Glu Pro Asp Asp Cys Phe Arg Glu Gly
1105                1110                1115                1120

Cys Thr Arg Arg Cys Pro Cys Cys Asn Val Asn Thr Ser Lys Ser Pro
                1125                1130                1135

Trp Ala Thr Gly Trp Gln Val Arg Lys Thr Cys Tyr Arg Ile Val Glu
            1140                1145                1150

His Ser Trp Phe Glu Ser Phe Ile Ile Phe Met Ile Leu Leu Ser Ser
            1155                1160                1165

Gly Ala Leu Ala Phe Glu Asp Asn Tyr Leu Glu Glu Lys Pro Arg Val
            1170                1175                1180

Lys Ser Val Leu Glu Tyr Thr Asp Arg Val Phe Thr Phe Ile Phe Val
1185                1190                1195                1200

Phe Glu Met Leu Leu Lys Trp Val Ala Tyr Gly Phe Lys Lys Tyr Phe
            1205                1210                1215

Thr Asn Ala Trp Cys Trp Leu Asp Phe Leu Ile Val Asn Ile Ser Leu
            1220                1225                1230

Thr Ser Leu Ile Ala Lys Ile Leu Glu Tyr Ser Asp Val Ala Ser Ile
            1235                1240                1245

Lys Ala Leu Arg Thr Leu Arg Ala Leu Arg Pro Leu Arg Ala Leu Ser
1250                1255                1260

Arg Phe Glu Gly Met Arg Val Val Asp Ala Leu Val Gly Ala Ile
1265                1270                1275                1280

Pro Ser Ile Met Asn Val Leu Leu Val Cys Leu Ile Phe Trp Leu Ile
            1285                1290                1295

Phe Ser Ile Met Gly Val Asn Leu Phe Ala Gly Lys Phe Ser Lys Cys
            1300                1305                1310

Val Asp Thr Arg Asn Asn Pro Phe Ser Asn Val Asn Ser Thr Met Val
            1315                1320                1325

Asn Asn Lys Ser Glu Cys His Asn Gln Asn Ser Thr Gly His Phe Phe
            1330                1335                1340

Trp Val Asn Val Lys Val Asn Phe Asp Asn Val Ala Met Gly Tyr Leu
1345                1350                1355                1360

Ala Leu Leu Gln Val Ala Thr Phe Lys Gly Trp Met Asp Ile Met Tyr
            1365                1370                1375

Ala Ala Val Asp Ser Gly Glu Ile Asn Ser Gln Pro Asn Trp Glu Asn
            1380                1385                1390

Asn Leu Tyr Met Tyr Leu Tyr Phe Val Val Phe Ile Ile Phe Gly Gly
```

```
                1395            1400              1405
Phe Phe Thr Leu Asn Leu Phe Val Gly Val Ile Ile Asp Asn Phe Asn
    1410            1415             1420

Gln Gln Lys Lys Lys Leu Gly Gly Gln Asp Ile Phe Met Thr Glu Glu
1425            1430             1435            1440

Gln Lys Lys Tyr Tyr Asn Ala Met Lys Lys Leu Gly Ser Lys Lys Pro
            1445             1450            1455

Gln Lys Pro Ile Pro Arg Pro Leu Asn Lys Tyr Gln Gly Phe Val Phe
            1460             1465            1470

Asp Ile Val Thr Arg Gln Ala Phe Asp Ile Ile Met Val Leu Ile
            1475             1480            1485

Cys Leu Asn Met Ile Thr Met Met Val Glu Thr Asp Glu Gln Gly Glu
    1490            1495             1500

Glu Lys Thr Lys Val Leu Gly Arg Ile Asn Gln Phe Phe Val Ala Val
1505            1510             1515            1520

Phe Thr Gly Glu Cys Val Met Lys Met Phe Ala Leu Arg Gln Tyr Tyr
            1525             1530            1535

Phe Thr Asn Gly Trp Asn Val Phe Asp Phe Ile Val Val Ile Leu Ser
            1540             1545            1550

Ile Gly Ser Leu Leu Phe Ser Ala Ile Leu Lys Ser Leu Glu Asn Tyr
            1555             1560            1565

Phe Ser Pro Thr Leu Phe Arg Val Ile Arg Leu Ala Arg Ile Gly Arg
            1570             1575            1580

Ile Leu Arg Leu Ile Arg Ala Ala Lys Gly Ile Arg Thr Leu Leu Phe
1585            1590             1595            1600

Ala Leu Met Met Ser Leu Pro Ala Leu Phe Asn Ile Gly Leu Leu Leu
            1605             1610            1615

Phe Leu Val Met Phe Ile Tyr Ser Ile Phe Gly Met Ala Ser Phe Ala
            1620             1625            1630

Asn Val Val Asp Glu Ala Gly Ile Asp Asp Met Phe Asn Phe Lys Thr
            1635             1640            1645

Phe Gly Asn Ser Met Leu Cys Leu Phe Gln Ile Thr Thr Ser Ala Gly
            1650             1655            1660

Trp Asp Gly Leu Leu Ser Pro Ile Leu Asn Thr Gly Pro Pro Tyr Cys
1665            1670             1675            1680

Asp Pro Asn Leu Pro Asn Ser Asn Gly Ser Arg Gly Asn Cys Gly Ser
            1685             1690            1695

Pro Ala Val Gly Ile Ile Phe Phe Thr Thr Tyr Ile Ile Ser Phe
            1700             1705            1710

Leu Ile Val Val Asn Met Tyr Ile Ala Val Ile Leu Glu Asn Phe Asn
            1715             1720            1725

Val Ala Thr Glu Glu Ser Thr Glu Pro Leu Ser Glu Asp Asp Phe Asp
    1730            1735             1740

Met Phe Tyr Glu Thr Trp Glu Lys Phe Asp Pro Glu Ala Thr Gln Phe
1745            1750             1755            1760

Ile Ala Phe Ser Ala Leu Ser Asp Phe Ala Asp Thr Leu Ser Gly Pro
            1765             1770            1775

Leu Arg Ile Pro Lys Pro Asn Gln Asn Ile Leu Ile Gln Met Asp Leu
            1780             1785            1790

Pro Leu Val Pro Gly Asp Lys Ile His Cys Leu Asp Ile Leu Phe Ala
            1795             1800            1805

Phe Thr Lys Asn Val Leu Gly Glu Ser Gly Glu Leu Asp Ser Leu Lys
    1810            1815             1820
```

```
Thr Asn Met Glu Glu Lys Phe Met Ala Thr Asn Leu Ser Lys Ala Ser
1825                1830                1835                1840

Tyr Glu Pro Ile Ala Thr Thr Leu Arg Trp Lys Gln Glu Asp Leu Ser
            1845                1850                1855

Ala Thr Val Ile Gln Lys Ala Tyr Arg Ser Tyr Met Leu His Arg Ser
            1860                1865                1870

Leu Thr Leu Ser Asn Thr Leu His Val Pro Arg Ala Glu Glu Asp Gly
            1875                1880                1885

Val Ser Leu Pro Gly Glu Gly Tyr Ile Thr Phe Met Ala Asn Ser Gly
            1890                1895                1900

Leu Pro Asp Lys Ser Glu Thr Ala Ser Ala Thr Ser Phe Pro Pro Ser
1905                1910                1915                1920

Tyr Asp Ser Val Thr Arg Gly Leu Ser Asp Arg Ala Asn Ile Asn Pro
            1925                1930                1935

Ser Ser Ser Met Gln Asn Glu Asp Glu Val Ala Ala Lys Glu Gly Asn
            1940                1945                1950

Ser Pro Gly Pro Gln
            1955
```

(2) INFORMATION FOR SEQ ID NO:3:

(i) SEQUENCE CHARACTERISTICS:
        (A) LENGTH: 2573 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 561..2126

(xi) SEQUENCE DESCRIPTION: SEQ ID NO:3:

```
CTGGGAGAGA AAGCGTCTCG CCTAGCGACT CCCAGAGCTT TAAGCCGGGA AGGGACAAGC      60

GTCAGGACAT CTCAGAATCC CGAACCTTCT AGGGAGGGAG GTTCTTACCT CCATGCTTCC     120

CGTAGGAACC TAATCCCAAT TATTTAGCTG TATTTATAAT ACAAAATATG AATGTTAAAT     180

GTACAAAATG CTTTCCCAGC ATGCCTGCAT CTCCTCCTAG AGTCCTGTTC CCAAGCCCTC     240

TCTACTCTCA GTACTGTAGA AAAGAAATAA GCTTTACGTG AGAAACCCAG GCACTGGATC     300

TTATCCAGGT GCTCACCTCA GAGTCTTTAG TGGGTGTAGC GCTGTGGTAG AGCATTTGGT     360

TATAGATACA AACCCAGGGC AGGGAGACTG CAGTGGCCAT TCTCTCCCAG GCCAGACGTG     420

CCCTGATCCT TCCCACAGAG ATGAGAAGGC TGGAACCAGA ACACTCAGGT TTTGGCTTCT     480

CTTGGGGGAG GAGAGGTAAT CTTGTTACTT TAATAACATC AGTGTGTCCC TCTCCTCTAC     540

TAGGAGGCCA GGACATCTTC ATG ACA GAA GAG CAG AAG AAG TAC TAC AAT         590
                       Met Thr Glu Glu Gln Lys Lys Tyr Tyr Asn
                         1               5                  10

GCC ATG AAG AAG CTG GGC TCC AAG AAA CCC CAG AAG CCC ATC CCA CGG       638
Ala Met Lys Lys Leu Gly Ser Lys Lys Pro Gln Lys Pro Ile Pro Arg
             15                  20                  25

CCC CTG AAT AAG TAC CAA GGC TTC GTG TTT GAC ATC GTG ACC AGG CAA       686
Pro Leu Asn Lys Tyr Gln Gly Phe Val Phe Asp Ile Val Thr Arg Gln
                 30                  35                  40

GCC TTT GAC ATC ATC ATC ATG GTT CTC ATC TGC CTC AAC ATG ATC ACC       734
Ala Phe Asp Ile Ile Ile Met Val Leu Ile Cys Leu Asn Met Ile Thr
     45                  50                  55
```

```
ATG ATG GTG GAG ACC GAC GAG CAG GGC GAG GAG AAG ACG AAG GTT CTG        782
Met Met Val Glu Thr Asp Glu Gln Gly Glu Glu Lys Thr Lys Val Leu
     60                  65                  70

GGC AGA ATC AAC CAG TTC TTT GTG GCC GTC TTC ACG GGC GAG TGT GTG        830
Gly Arg Ile Asn Gln Phe Phe Val Ala Val Phe Thr Gly Glu Cys Val
 75                  80                  85                  90

ATG AAG ATG TTC GCC CTG CGA CAG TAC TAC TTC ACC AAC GGC TGG AAC        878
Met Lys Met Phe Ala Leu Arg Gln Tyr Tyr Phe Thr Asn Gly Trp Asn
                 95                 100                 105

GTG TTC GAC TTC ATA GTG GTG ATC CTG TCC ATT GGG AGT CTG CTG TTT        926
Val Phe Asp Phe Ile Val Val Ile Leu Ser Ile Gly Ser Leu Leu Phe
            110                 115                 120

TCT GCA ATC CTT AAG TCA CTG GAA AAC TAC TTC TCC CCG ACG CTC TTC        974
Ser Ala Ile Leu Lys Ser Leu Glu Asn Tyr Phe Ser Pro Thr Leu Phe
        125                 130                 135

CGG GTC ATC CGT CTG GCC AGG ATC GGC CGC ATC CTC AGG CTG ATC CGA       1022
Arg Val Ile Arg Leu Ala Arg Ile Gly Arg Ile Leu Arg Leu Ile Arg
    140                 145                 150

GCA GCC AAG GGG ATT CGC ACG CTG CTC TTC GCC CTC ATG ATG TCC CTG       1070
Ala Ala Lys Gly Ile Arg Thr Leu Leu Phe Ala Leu Met Met Ser Leu
155                 160                 165                 170

CCC GCC CTC TTC AAC ATC GGC CTC CTC CTC TTC CTC GTC ATG TTC ATC       1118
Pro Ala Leu Phe Asn Ile Gly Leu Leu Leu Phe Leu Val Met Phe Ile
                175                 180                 185

TAC TCC ATC TTC GGC ATG GCC AGC TTC GCT AAC GTC GTG GAC GAG GCC       1166
Tyr Ser Ile Phe Gly Met Ala Ser Phe Ala Asn Val Val Asp Glu Ala
            190                 195                 200

GGC ATC GAC GAC ATG TTC AAC TTC AAG ACC TTT GGC AAC AGC ATG CTG       1214
Gly Ile Asp Asp Met Phe Asn Phe Lys Thr Phe Gly Asn Ser Met Leu
        205                 210                 215

TGC CTG TTC CAG ATC ACC ACC TCG GCC GGC TGG GAC GGC CTC CTC AGC       1262
Cys Leu Phe Gln Ile Thr Thr Ser Ala Gly Trp Asp Gly Leu Leu Ser
    220                 225                 230

CCC ATC CTC AAC ACG GGG CCT CCC TAC TGC GAC CCC AAC CTG CCC AAC       1310
Pro Ile Leu Asn Thr Gly Pro Pro Tyr Cys Asp Pro Asn Leu Pro Asn
235                 240                 245                 250

AGC AAC GGC TCC CGG GGG AAC TGC GGG AGC CCG GCG GTG GGC ATC ATC       1358
Ser Asn Gly Ser Arg Gly Asn Cys Gly Ser Pro Ala Val Gly Ile Ile
                255                 260                 265

TTC TTC ACC ACC TAC ATC ATC ATC TCC TTC CTC ATC GTG GTC AAC ATG       1406
Phe Phe Thr Thr Tyr Ile Ile Ile Ser Phe Leu Ile Val Val Asn Met
            270                 275                 280

TAC ATC GCA GTG ATT CTG GAG AAC TTC AAC GTA GCC ACC GAG GAG AGC       1454
Tyr Ile Ala Val Ile Leu Glu Asn Phe Asn Val Ala Thr Glu Glu Ser
        285                 290                 295

ACG GAG CCC CTG AGC GAG GAC GAC TTC GAC ATG TTC TAT GAG ACC TGG       1502
Thr Glu Pro Leu Ser Glu Asp Asp Phe Asp Met Phe Tyr Glu Thr Trp
    300                 305                 310

GAG AAG TTC GAC CCG GAG GCC ACC CAG TTC ATT GCC TTT TCT GCC CTC       1550
Glu Lys Phe Asp Pro Glu Ala Thr Gln Phe Ile Ala Phe Ser Ala Leu
315                 320                 325                 330

TCA GAC TTC GCG GAC ACG CTC TCC GGC CCT CTT AGA ATC CCC AAA CCC       1598
Ser Asp Phe Ala Asp Thr Leu Ser Gly Pro Leu Arg Ile Pro Lys Pro
                335                 340                 345

AAC CAG AAT ATA TTA ATC CAG ATG GAC CTG CCG TTG GTC CCC GGG GAT       1646
Asn Gln Asn Ile Leu Ile Gln Met Asp Leu Pro Leu Val Pro Gly Asp
            350                 355                 360

AAG ATC CAC TGT CTG GAC ATC CTT TTT GCC TTC ACA AAG AAC GTC TTG       1694
Lys Ile His Cys Leu Asp Ile Leu Phe Ala Phe Thr Lys Asn Val Leu
        365                 370                 375
```

```
GGA GAA TCC GGG GAG TTG GAC TCC CTG AAG ACC AAT ATG GAA GAG AAG    1742
Gly Glu Ser Gly Glu Leu Asp Ser Leu Lys Thr Asn Met Glu Glu Lys
    380                 385                 390

TTT ATG GCG ACC AAT CTC TCC AAA GCA TCC TAT GAA CCA ATA GCC ACC    1790
Phe Met Ala Thr Asn Leu Ser Lys Ala Ser Tyr Glu Pro Ile Ala Thr
395                 400                 405                 410

ACC CTC CGG TGG AAG CAG GAA GAC CTC TCA GCC ACA GTC ATT CAA AAG    1838
Thr Leu Arg Trp Lys Gln Glu Asp Leu Ser Ala Thr Val Ile Gln Lys
                415                 420                 425

GCC TAC CGG AGC TAC ATG CTG CAC CGC TCC TTG ACA CTC TCC AAC ACC    1886
Ala Tyr Arg Ser Tyr Met Leu His Arg Ser Leu Thr Leu Ser Asn Thr
        430                 435                 440

CTG CAT GTG CCC AGG GCT GAG GAG GAT GGC GTG TCA CTT CCC GGG GAA    1934
Leu His Val Pro Arg Ala Glu Glu Asp Gly Val Ser Leu Pro Gly Glu
            445                 450                 455

GGC TAC ATT ACA TTC ATG GCA AAC AGT GGA CTC CCG GAC AAA TCA GAA    1982
Gly Tyr Ile Thr Phe Met Ala Asn Ser Gly Leu Pro Asp Lys Ser Glu
460                 465                 470

ACT GCC TCT GCT ACG TCT TTC CCG CCA TCC TAT GAC AGT GTC ACC AGG    2030
Thr Ala Ser Ala Thr Ser Phe Pro Pro Ser Tyr Asp Ser Val Thr Arg
475                 480                 485                 490

GGC CTG AGT GAC CGG GCC AAC ATT AAC CCA TCT AGC TCA ATG CAA AAT    2078
Gly Leu Ser Asp Arg Ala Asn Ile Asn Pro Ser Ser Ser Met Gln Asn
                495                 500                 505

GAA GAT GAG GTC GCT GCT AAG GAA GGA AAC AGC CCT GGA CCT CAG TGAAGGCA 2133
Glu Asp Glu Val Ala Ala Lys Glu Gly Asn Ser Pro Gly Pro Gln
        510                 515                 520

CAGGCATGCA CAGGGCAGGT TCCAATGTCT TTCTCTGCTG TACTAACTCC TTCCCTCTGG   2193

AGGTGGCACC AACCTCCAGC CTCCACCAAT GCATGTCACT GGTCATGGTG TCAGAACTGA   2253

ATGGGGACAT CCTTGAGAAA GCCCCCACCC AATAGGAAT CAAAAGCCAA GGATACTCCT    2313

CCATTCTGAC GTCCCTTCCG AGTTCCAGA AGATGTCATT GCTCCCTTCT GTTTGTGACC    2373

AGAGACGTGA TTCACCAACT TCTCGGAGCC AGAGACACAT AGCAAAGACT TTTCTGCTGG   2433

TGTCGGGCAG TCTTAGAGAA GTCACGTAGG GGTTGGTACT GAGAATTAGG GTTTGCATGA   2493

CTGCATGCTC ACAGCTGCCG GACAATACCT GTGAGTCGGC CATTAAAATT AATATTTTTA   2553

AAGTTAAAAA AAAAAAAAA                                                2573
```

(2) INFORMATION FOR SEQ ID NO:4:

(i) SEQUENCE CHARACTERISTICS:
        (A) LENGTH: 521 amino acids
        (B) TYPE: amino acid
        (D) TOPOLOGY: linear (ii) MOLECULE TYPE: protein (xi) SEQUENCE DESCRIPTION: SEQ ID NO:4:

```
Met Thr Glu Glu Gln Lys Lys Tyr Tyr Asn Ala Met Lys Lys Leu Gly
1               5                   10                  15

Ser Lys Lys Pro Gln Lys Pro Ile Pro Arg Pro Leu Asn Lys Tyr Gln
                20                  25                  30

Gly Phe Val Phe Asp Ile Val Thr Arg Gln Ala Phe Asp Ile Ile Ile
            35                  40                  45

Met Val Leu Ile Cys Leu Asn Met Ile Thr Met Met Val Glu Thr Asp
        50                  55                  60

Glu Gln Gly Glu Glu Lys Thr Lys Val Leu Gly Arg Ile Asn Gln Phe
65              70                  75                  80
```

-continued

```
Phe Val Ala Val Phe Thr Gly Glu Cys Val Met Lys Met Phe Ala Leu
                 85                  90                  95

Arg Gln Tyr Tyr Phe Thr Asn Gly Trp Asn Val Phe Asp Phe Ile Val
            100                 105                 110

Val Ile Leu Ser Ile Gly Ser Leu Leu Phe Ser Ala Ile Leu Lys Ser
        115                 120                 125

Leu Glu Asn Tyr Phe Ser Pro Thr Leu Phe Arg Val Ile Arg Leu Ala
    130                 135                 140

Arg Ile Gly Arg Ile Leu Arg Leu Ile Arg Ala Ala Lys Gly Ile Arg
145                 150                 155                 160

Thr Leu Leu Phe Ala Leu Met Met Ser Leu Pro Ala Leu Phe Asn Ile
                165                 170                 175

Gly Leu Leu Leu Phe Leu Val Met Phe Ile Tyr Ser Ile Phe Gly Met
                180                 185                 190

Ala Ser Phe Ala Asn Val Val Asp Glu Ala Gly Ile Asp Asp Met Phe
            195                 200                 205

Asn Phe Lys Thr Phe Gly Asn Ser Met Leu Cys Leu Phe Gln Ile Thr
    210                 215                 220

Thr Ser Ala Gly Trp Asp Gly Leu Leu Ser Pro Ile Leu Asn Thr Gly
225                 230                 235                 240

Pro Pro Tyr Cys Asp Pro Asn Leu Pro Asn Ser Asn Gly Ser Arg Gly
                245                 250                 255

Asn Cys Gly Ser Pro Ala Val Gly Ile Ile Phe Phe Thr Thr Tyr Ile
            260                 265                 270

Ile Ile Ser Phe Leu Ile Val Val Asn Met Tyr Ile Ala Val Ile Leu
    275                 280                 285

Glu Asn Phe Asn Val Ala Thr Glu Glu Ser Thr Glu Pro Leu Ser Glu
290                 295                 300

Asp Asp Phe Asp Met Phe Tyr Glu Thr Trp Glu Lys Phe Asp Pro Glu
305                 310                 315                 320

Ala Thr Gln Phe Ile Ala Phe Ser Ala Leu Ser Asp Phe Ala Asp Thr
                325                 330                 335

Leu Ser Gly Pro Leu Arg Ile Pro Lys Pro Asn Gln Asn Ile Leu Ile
            340                 345                 350

Gln Met Asp Leu Pro Leu Val Pro Gly Asp Lys Ile His Cys Leu Asp
    355                 360                 365

Ile Leu Phe Ala Phe Thr Lys Asn Val Leu Gly Glu Ser Gly Glu Leu
    370                 375                 380

Asp Ser Leu Lys Thr Asn Met Glu Glu Lys Phe Met Ala Thr Asn Leu
385                 390                 395                 400

Ser Lys Ala Ser Tyr Glu Pro Ile Ala Thr Thr Leu Arg Trp Lys Gln
                405                 410                 415

Glu Asp Leu Ser Ala Thr Val Ile Gln Lys Ala Tyr Arg Ser Tyr Met
            420                 425                 430

Leu His Arg Ser Leu Thr Leu Ser Asn Thr Leu His Val Pro Arg Ala
    435                 440                 445

Glu Glu Asp Gly Val Ser Leu Pro Gly Glu Gly Tyr Ile Thr Phe Met
450                 455                 460

Ala Asn Ser Gly Leu Pro Asp Lys Ser Glu Thr Ala Ser Ala Thr Ser
465                 470                 475                 480

Phe Pro Pro Ser Tyr Asp Ser Val Thr Arg Gly Leu Ser Asp Arg Ala
                485                 490                 495
```

```
Asn Ile Asn Pro Ser Ser Met Gln Asn Glu Asp Glu Val Ala Ala
            500                 505                 510
Lys Glu Gly Asn Ser Pro Gly Pro Gln
        515                 520

(2) INFORMATION FOR SEQ ID NO:5:

(i) SEQUENCE CHARACTERISTICS:
        (A) LENGTH: 7052 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 204..6602

(xi) SEQUENCE DESCRIPTION: SEQ ID NO:5:

TAGCTTGCTT CTGCTAATGC TACCCCAGGC CTTTAGACAG AGAACAGATG GCAGATGGAG      60

TTTCTTATTG CCATGCGCAA ACGCTGAGCC CACCTCATGA TCCCGGACCC CATGGTTTTC    120

AGTAGACAAC CTGGGCTAAG AAGAGATCTC CGACCTTATA GAGCAGCAAA GAGTGTAAAT    180

TCTTCCCCAA GAAGAATGAG AAG ATG GAG CTC CCC TTT GCG TCC GTG GGA        230
                         Met Glu Leu Pro Phe Ala Ser Val Gly
                          1               5

ACT ACC AAT TTC AGA CGG TTC ACT CCA GAG TCA CTG GCA GAG ATC GAG      278
Thr Thr Asn Phe Arg Arg Phe Thr Pro Glu Ser Leu Ala Glu Ile Glu
 10              15                  20                  25

AAG CAG ATT GCT GCT CAC CGG GCA GCC AAG AAG GCC AGA ACC AAG CAC      326
Lys Gln Ile Ala Ala His Arg Ala Ala Lys Lys Ala Arg Thr Lys His
            30                  35                  40

AGA GGA CAG GAG GAC AAG GGC GAG AAG CCC AGG CCT CAG CTG GAC TTG      374
Arg Gly Gln Glu Asp Lys Gly Glu Lys Pro Arg Pro Gln Leu Asp Leu
                45                  50                  55

AAA GAC TGT AAC CAG CTG CCC AAG TTC TAT GGT GAG CTC CCA GCA GAA      422
Lys Asp Cys Asn Gln Leu Pro Lys Phe Tyr Gly Glu Leu Pro Ala Glu
            60                  65                  70

CTG GTC GGG GAG CCC CTG GAG GAC CTA GAC CCT TTC TAC AGC ACA CAC      470
Leu Val Gly Glu Pro Leu Glu Asp Leu Asp Pro Phe Tyr Ser Thr His
 75                  80                  85

CGG ACA TTC ATG GTG TTG AAT AAA AGC AGG ACC ATT TCC AGA TTC AGT      518
Arg Thr Phe Met Val Leu Asn Lys Ser Arg Thr Ile Ser Arg Phe Ser
 90                  95                 100                 105

GCC ACT TGG GCC CTG TGG CTC TTC AGT CCC TTC AAC CTG ATC AGA AGA      566
Ala Thr Trp Ala Leu Trp Leu Phe Ser Pro Phe Asn Leu Ile Arg Arg
            110                 115                 120

ACA GCC ATC AAA GTG TCT GTC CAT TCC TGG TTC TCC ATA TTC ATC ACC      614
Thr Ala Ile Lys Val Ser Val His Ser Trp Phe Ser Ile Phe Ile Thr
            125                 130                 135

ATC ACT ATT TTG GTC AAC TGC GTG TGC ATG ACC CGA ACT GAT CTT CCA      662
Ile Thr Ile Leu Val Asn Cys Val Cys Met Thr Arg Thr Asp Leu Pro
            140                 145                 150

GAG AAA GTC GAG TAC GTC TTC ACT GTC ATT TAC ACC TTC GAG GCT CTG      710
Glu Lys Val Glu Tyr Val Phe Thr Val Ile Tyr Thr Phe Glu Ala Leu
 155                 160                 165

ATT AAG ATA CTG GCA AGA GGG TTT TGT CTA AAT GAG TTC ACT TAT CTT      758
Ile Lys Ile Leu Ala Arg Gly Phe Cys Leu Asn Glu Phe Thr Tyr Leu
170                 175                 180                 185

CGA GAT CCG TGG AAC TGG CTG GAC TTC AGT GTC ATT ACC TTG GCG TAT      806
Arg Asp Pro Trp Asn Trp Leu Asp Phe Ser Val Ile Thr Leu Ala Tyr
```

```
                   190                 195                 200
GTG GGT GCA GCG ATA GAC CTC CGA GGA ATC TCA GGC CTG CGG ACA TTC       854
Val Gly Ala Ala Ile Asp Leu Arg Gly Ile Ser Gly Leu Arg Thr Phe
                205                 210                 215

CGA GTT CTC AGA GCC CTG AAA ACT GTT TCT GTG ATC CCA GGA CTG AAG       902
Arg Val Leu Arg Ala Leu Lys Thr Val Ser Val Ile Pro Gly Leu Lys
            220                 225                 230

GTC ATC GTG GGA GCC CTG ATC CAC TCA GTG AGG AAG CTG GCC GAC GTG       950
Val Ile Val Gly Ala Leu Ile His Ser Val Arg Lys Leu Ala Asp Val
        235                 240                 245

ACT ATC CTC ACA GTC TTC TGC CTG AGC GTC TTC GCC TTG GTG GGC CTG       998
Thr Ile Leu Thr Val Phe Cys Leu Ser Val Phe Ala Leu Val Gly Leu
250                 255                 260                 265

CAG CTC TTT AAG GGG AAC CTT AAG AAC AAA TGC ATC AGG AAC GGA ACA      1046
Gln Leu Phe Lys Gly Asn Leu Lys Asn Lys Cys Ile Arg Asn Gly Thr
                270                 275                 280

GAT CCC CAC AAG GCT GAC AAC CTC TCA TCT GAA ATG GCA GAA TAC ATC      1094
Asp Pro His Lys Ala Asp Asn Leu Ser Ser Glu Met Ala Glu Tyr Ile
            285                 290                 295

TTC ATC AAG CCT GGT ACT ACG GAT CCC TTA CTG TGC GGC AAT GGG TCT      1142
Phe Ile Lys Pro Gly Thr Thr Asp Pro Leu Leu Cys Gly Asn Gly Ser
        300                 305                 310

GAT GCT GGT CAC TGC CCT GGA GGC TAT GTC TGC CTG AAA ACT CCT GAC      1190
Asp Ala Gly His Cys Pro Gly Gly Tyr Val Cys Leu Lys Thr Pro Asp
315                 320                 325

AAC CCG GAT TTT AAC TAC ACC AGC TTT GAT TCC TTT GCG TGG GCA TTC      1238
Asn Pro Asp Phe Asn Tyr Thr Ser Phe Asp Ser Phe Ala Trp Ala Phe
330                 335                 340                 345

CTC TCA CTG TTC CGC CTC ATG ACG CAG GAC TCC TGG GAG CGC CTG TAC      1286
Leu Ser Leu Phe Arg Leu Met Thr Gln Asp Ser Trp Glu Arg Leu Tyr
                350                 355                 360

CAG CAG ACA CTC CGG GCT TCT GGG AAA ATG TAC ATG GTC TTT TTC GTG      1334
Gln Gln Thr Leu Arg Ala Ser Gly Lys Met Tyr Met Val Phe Phe Val
            365                 370                 375

CTG GTT ATT TTC CTT GGA TCG TTC TAC CTG GTC AAT TTG ATC TTG GCC      1382
Leu Val Ile Phe Leu Gly Ser Phe Tyr Leu Val Asn Leu Ile Leu Ala
        380                 385                 390

GTG GTC ACC ATG GCG TAT GAA GAG CAG AGC CAG GCA ACA ATT GCA GAA      1430
Val Val Thr Met Ala Tyr Glu Glu Gln Ser Gln Ala Thr Ile Ala Glu
395                 400                 405

ATC GAA GCC AAG GAA AAA AAG TTC CAG GAA GCC CTT GAG GTG CTG CAG      1478
Ile Glu Ala Lys Glu Lys Lys Phe Gln Glu Ala Leu Glu Val Leu Gln
410                 415                 420                 425

AAG GAA CAG GAG GTG CTG GCA GCC CTG GGG ATT GAC ACG ACC TCG CTC      1526
Lys Glu Gln Glu Val Leu Ala Ala Leu Gly Ile Asp Thr Thr Ser Leu
                430                 435                 440

CAG TCC CAC AGT GGA TCA CCC TTA GCC TCC AAA AAC GCC AAT GAG AGA      1574
Gln Ser His Ser Gly Ser Pro Leu Ala Ser Lys Asn Ala Asn Glu Arg
            445                 450                 455

AGA CCC AGG GTG AAA TCA AGG GTG TCA GAG GGC TCC ACG GAT GAC AAC      1622
Arg Pro Arg Val Lys Ser Arg Val Ser Glu Gly Ser Thr Asp Asp Asn
        460                 465                 470

AGG TCA CCC CAA TCT GAC CCT TAC AAC CAG CGC AGG ATG TCT TTC CTA      1670
Arg Ser Pro Gln Ser Asp Pro Tyr Asn Gln Arg Arg Met Ser Phe Leu
475                 480                 485

GGC CTG TCT TCA GGA AGA CGC AGG GCT AGC CAC GGC AGT GTG TTC CAC      1718
Gly Leu Ser Ser Gly Arg Arg Arg Ala Ser His Gly Ser Val Phe His
490                 495                 500                 505

TTC CGA GCG CCC AGC CAA GAC ATC TCA TTT CCT GAC GGG ATC ACC CCT      1766
```

-continued

```
Phe Arg Ala Pro Ser Gln Asp Ile Ser Phe Pro Asp Gly Ile Thr Pro
            510                 515                 520

GAT GAT GGG GTC TTT CAC GGA GAC CAG GAA AGC CGT CGA GGT TCC ATA    1814
Asp Asp Gly Val Phe His Gly Asp Gln Glu Ser Arg Arg Gly Ser Ile
            525                 530                 535

TTG CTG GGC AGG GGT GCT GGG CAG ACA GGT CCA CTC CCC AGG AGC CCA    1862
Leu Leu Gly Arg Gly Ala Gly Gln Thr Gly Pro Leu Pro Arg Ser Pro
            540                 545                 550

CTG CCT CAG TCC CCC AAC CCT GGC CGT AGA CAT GGA GAA GAG GGA CAG    1910
Leu Pro Gln Ser Pro Asn Pro Gly Arg Arg His Gly Glu Glu Gly Gln
555                 560                 565

CTC GGA GTG CCC ACT GGT GAG CTT ACC GCT GGA GCG CCT GAA GGC CCG    1958
Leu Gly Val Pro Thr Gly Glu Leu Thr Ala Gly Ala Pro Glu Gly Pro
570                 575                 580                 585

GCA CTC GAC ACT ACA GGG CAG AAG AGC TTC CTG TCT GCG GGC TAC TTG    2006
Ala Leu Asp Thr Thr Gly Gln Lys Ser Phe Leu Ser Ala Gly Tyr Leu
            590                 595                 600

AAC GAA CCT TTC CGA GCA CAG AGG GCC ATG AGC GTT GTC AGT ATC ATG    2054
Asn Glu Pro Phe Arg Ala Gln Arg Ala Met Ser Val Val Ser Ile Met
            605                 610                 615

ACT TCT GTC ATT GAG GAG CTT GAA GAG TCT AAG CTG AAG TGC CCA CCC    2102
Thr Ser Val Ile Glu Glu Leu Glu Glu Ser Lys Leu Lys Cys Pro Pro
            620                 625                 630

TGC TTG ATC AGC TTC GCT CAG AAG TAT CTG ATC TGG GAG TGC TGC CCC    2150
Cys Leu Ile Ser Phe Ala Gln Lys Tyr Leu Ile Trp Glu Cys Cys Pro
            635                 640                 645

AAG TGG AGG AAG TTC AAG ATG GCG CTG TTC GAG CTG GTG ACT GAC CCC    2198
Lys Trp Arg Lys Phe Lys Met Ala Leu Phe Glu Leu Val Thr Asp Pro
650                 655                 660                 665

TTC GCA GAG CTT ACC ATC ACC CTC TGC ATC GTG GTG AAC ACC GTC TTC    2246
Phe Ala Glu Leu Thr Ile Thr Leu Cys Ile Val Val Asn Thr Val Phe
            670                 675                 680

ATG GCC ATG GAG CAC TAC CCC ATG ACC GAT GCC TTC GAT GCC ATG CTT    2294
Met Ala Met Glu His Tyr Pro Met Thr Asp Ala Phe Asp Ala Met Leu
            685                 690                 695

CAA GCC GGC AAC ATT GTC TTC ACC GTG TTT TTC ACA ATG GAG ATG GCC    2342
Gln Ala Gly Asn Ile Val Phe Thr Val Phe Phe Thr Met Glu Met Ala
            700                 705                 710

TTC AAG ATC ATT GCC TTC GAC CCC TAC TAT TAC TTC CAG AAG AAG TGG    2390
Phe Lys Ile Ile Ala Phe Asp Pro Tyr Tyr Tyr Phe Gln Lys Lys Trp
            715                 720                 725

AAT ATC TTC GAC TGT GTC ATC GTC ACC GTG AGC CTT CTG GAG CTG AGT    2438
Asn Ile Phe Asp Cys Val Ile Val Thr Val Ser Leu Leu Glu Leu Ser
730                 735                 740                 745

GCA TCC AAG AAG GGC AGC CTG TCT GTG CTC CGT TCC TTA CGC TTG GCA    2486
Ala Ser Lys Lys Gly Ser Leu Ser Val Leu Arg Ser Leu Arg Leu Ala
            750                 755                 760

CTC GAC ACT ACA GGG CAG AAG AGC TTC CTG TCT GCG GGC TAC TTG AAC    2534
Leu Asp Thr Thr Gly Gln Lys Ser Phe Leu Ser Ala Gly Tyr Leu Asn
            765                 770                 775

GAA CCT TTC CGA GCA CAG AGG GCC ATG AGC GTT GTC AGT ATC ATG ACT    2582
Glu Pro Phe Arg Ala Gln Arg Ala Met Ser Val Val Ser Ile Met Thr
            780                 785                 790

TCT GTC ATT GAG GAG CTT GAA GAG TCT AAG CTG AAG TGC CCA CCC TGC    2630
Ser Val Ile Glu Glu Leu Glu Glu Ser Lys Leu Lys Cys Pro Pro Cys
            795                 800                 805

TTG ATC AGC TTC GCT CAG AAG TAT CTG ATC TGG GAG TGC TGC CCC AAG    2678
Leu Ile Ser Phe Ala Gln Lys Tyr Leu Ile Trp Glu Cys Cys Pro Lys
810                 815                 820                 825
```

```
TGG AGG AAG TTC AAG ATG GCG CTG TTC GAG CTG GTG ACT GAC CCC TTC      2726
Trp Arg Lys Phe Lys Met Ala Leu Phe Glu Leu Val Thr Asp Pro Phe
            830                 835                 840

GCA GAG CTT ACC ATC ACC CTC TGC ATC GTG GTG AAC ACC GTC TTC ATG      2774
Ala Glu Leu Thr Ile Thr Leu Cys Ile Val Val Asn Thr Val Phe Met
            845                 850                 855

GCC ATG GAG CAC TAC CCC ATG ACC GAT GCC TTC GAT GCC ATG CTT CAA      2822
Ala Met Glu His Tyr Pro Met Thr Asp Ala Phe Asp Ala Met Leu Gln
            860                 865                 870

GCC GGC AAC ATT GTC TTC ACC GTG TTT TTC ACA ATG GAG ATG GCC TTC      2870
Ala Gly Asn Ile Val Phe Thr Val Phe Phe Thr Met Glu Met Ala Phe
            875                 880                 885

AAG ATC ATT GCC TTC GAC CCC TAC TAT TAC TTC CAG AAG AAG TGG AAT      2918
Lys Ile Ile Ala Phe Asp Pro Tyr Tyr Tyr Phe Gln Lys Lys Trp Asn
890                 895                 900                 905

ATC TTC GAC TGT GTC ATC GTC ACC GTG AGC CTT CTG GAG CTG AGT GCA      2966
Ile Phe Asp Cys Val Ile Val Thr Val Ser Leu Leu Glu Leu Ser Ala
                910                 915                 920

TCC AAG AAG GGC AGC CTG TCT GTG CTC CGT TCC TTA CGC TTG CTG CGG      3014
Ser Lys Lys Gly Ser Leu Ser Val Leu Arg Ser Leu Arg Leu Leu Arg
            925                 930                 935

GTC TTC AAG CTG GCC AAG TCC TGG CCC ACC CTG AAC ACC CTC ATC AAG      3062
Val Phe Lys Leu Ala Lys Ser Trp Pro Thr Leu Asn Thr Leu Ile Lys
            940                 945                 950

ATC ATC GGG AAC TCA GTG GGG GCC CTG GGC AAC CTG ACC TTT ATC CTG      3110
Ile Ile Gly Asn Ser Val Gly Ala Leu Gly Asn Leu Thr Phe Ile Leu
955                 960                 965

GCC ATC ATC GTC TTC ATC TTC GCC CTG GTC GGA AAG CAG CTT CTC TCA      3158
Ala Ile Ile Val Phe Ile Phe Ala Leu Val Gly Lys Gln Leu Leu Ser
970                 975                 980                 985

GAG GAC TAC GGG TGC CGC AAG GAC GGC GTC TCC GTG TGG AAC GGC GAG      3206
Glu Asp Tyr Gly Cys Arg Lys Asp Gly Val Ser Val Trp Asn Gly Glu
                990                 995                 1000

AAG CTC CGC TGG CAC ATG TGT GAC TTC TTC CAT TCC TTC CTG GTC GTC      3254
Lys Leu Arg Trp His Met Cys Asp Phe Phe His Ser Phe Leu Val Val
            1005                1010                1015

TTC CGA ATC CTC TGC GGG GAG TGG ATC GAG AAC ATG TGG GTC TGC ATG      3302
Phe Arg Ile Leu Cys Gly Glu Trp Ile Glu Asn Met Trp Val Cys Met
            1020                1025                1030

GAG GTC AGC CAG AAA TCC ATC TGC CTC ATC CTC TTC TTG ACT GTG ATG      3350
Glu Val Ser Gln Lys Ser Ile Cys Leu Ile Leu Phe Leu Thr Val Met
            1035                1040                1045

GTG CTG GGC AAC CTA GTG GTG CTC AAC CTT TTC ATC GCT TTA CTG CTG      3398
Val Leu Gly Asn Leu Val Val Leu Asn Leu Phe Ile Ala Leu Leu Leu
1050                1055                1060                1065

AAC TCC TTC AGC GCG GAC AAC CTC ACG GCT CCA GAG GAT GAC GGG GAG      3446
Asn Ser Phe Ser Ala Asp Asn Leu Thr Ala Pro Glu Asp Asp Gly Glu
            1070                1075                1080

GTG AAC AAC TTG CAG TTA GCA CTG GCC AGG ATC CAG GTA CTT GGC CAT      3494
Val Asn Asn Leu Gln Leu Ala Leu Ala Arg Ile Gln Val Leu Gly His
            1085                1090                1095

CGG GCC AGC AGG GCC ATC GCC AGT TAC ATC AGC AGC CAC TGC CGA TTC      3542
Arg Ala Ser Arg Ala Ile Ala Ser Tyr Ile Ser Ser His Cys Arg Phe
            1100                1105                1110

CGC TGG CCC AAG GTG GAG ACC CAG CTG GGC ATG AAG CCC CCA CTC ACC      3590
Arg Trp Pro Lys Val Glu Thr Gln Leu Gly Met Lys Pro Pro Leu Thr
            1115                1120                1125

AGC TCA GAG GCC AAG AAC CAC ATT GCC ACT GAT GCT GTC AGT GCT GCA      3638
Ser Ser Glu Ala Lys Asn His Ile Ala Thr Asp Ala Val Ser Ala Ala
1130                1135                1140                1145
```

```
GTG GGG AAC CTG ACA AAG CCA GCT CTC AGT AGC CCC AAG GAG AAT CAC         3686
Val Gly Asn Leu Thr Lys Pro Ala Leu Ser Ser Pro Lys Glu Asn His
            1150                1155                1160

GGG GAC TTC ATC ACT GAT CCC AAC GTG TGG GTC TCT GTG CCC ATT GCT         3734
Gly Asp Phe Ile Thr Asp Pro Asn Val Trp Val Ser Val Pro Ile Ala
            1165                1170                1175

GAG GGG GAA TCT GAC CTC GAC GAG CTC GAG GAA GAT ATG GAG CAG GCT         3782
Glu Gly Glu Ser Asp Leu Asp Glu Leu Glu Glu Asp Met Glu Gln Ala
            1180                1185                1190

TCG CAG AGC TCC TGG CAG GAA GAG GAC CCC AAG GGA CAG CAG GAG CAG         3830
Ser Gln Ser Ser Trp Gln Glu Glu Asp Pro Lys Gly Gln Gln Glu Gln
            1195                1200                1205

TTG CCA CAA GTC CAA AAG TGT GAA AAC CAC CAG GCA GCC AGA AGC CCA         3878
Leu Pro Gln Val Gln Lys Cys Glu Asn His Gln Ala Ala Arg Ser Pro
1210                1215                1220                1225

GCC TCC ATG ATG TCC TCT GAG GAC CTG GCT CCA TAC CTG GGT GAG AGC         3926
Ala Ser Met Met Ser Ser Glu Asp Leu Ala Pro Tyr Leu Gly Glu Ser
            1230                1235                1240

TGG AAG AGG AAG GAT AGC CCT CAG GTC CCT GCC GAG GGA GTG GAT GAC         3974
Trp Lys Arg Lys Asp Ser Pro Gln Val Pro Ala Glu Gly Val Asp Asp
            1245                1250                1255

ACG AGC TCC TCT GAG GGC AGC ACG GTG GAC TGC CCG GAC CCA GAG GAA         4022
Thr Ser Ser Ser Glu Gly Ser Thr Val Asp Cys Pro Asp Pro Glu Glu
            1260                1265                1270

ATC CTG AGG AAG ATC CCC GAG CTG GCA GAT GAC CTG GAC GAG CCC GAT         4070
Ile Leu Arg Lys Ile Pro Glu Leu Ala Asp Asp Leu Asp Glu Pro Asp
            1275                1280                1285

GAC TGT TTC ACA GAA GGC TGC ACT CGC CGC TGT CCC TGC TGC AAC GTG         4118
Asp Cys Phe Thr Glu Gly Cys Thr Arg Arg Cys Pro Cys Cys Asn Val
1290                1295                1300                1305

AAT ACT AGC AAG TCT CCT TGG GCC ACA GGC TGG CAG GTG CGC AAG ACC         4166
Asn Thr Ser Lys Ser Pro Trp Ala Thr Gly Trp Gln Val Arg Lys Thr
            1310                1315                1320

TGC TAC CGC ATC GTG GAG CAC AGC TGG TTT GAG AGT TTC ATC ATC TTC         4214
Cys Tyr Arg Ile Val Glu His Ser Trp Phe Glu Ser Phe Ile Ile Phe
            1325                1330                1335

ATG ATC CTG CTC AGC AGT GGA GCG CTG GCC TTT GAG GAT AAC TAC CTG         4262
Met Ile Leu Leu Ser Ser Gly Ala Leu Ala Phe Glu Asp Asn Tyr Leu
            1340                1345                1350

GAA GAG AAA CCC CGA GTG AAG TCC GTG CTG GAG TAC ACT GAC CGA GTG         4310
Glu Glu Lys Pro Arg Val Lys Ser Val Leu Glu Tyr Thr Asp Arg Val
            1355                1360                1365

TTC ACC TTC ATC TTC GTC TTT GAG ATG CTG CTC AAG TGG GTA GCC TAT         4358
Phe Thr Phe Ile Phe Val Phe Glu Met Leu Leu Lys Trp Val Ala Tyr
1370                1375                1380                1385

GGC TTC AAA AAG TAT TTC ACC AAT GCC TGG TGC TGG CTG GAC TTC CTC         4406
Gly Phe Lys Lys Tyr Phe Thr Asn Ala Trp Cys Trp Leu Asp Phe Leu
            1390                1395                1400

ATT GTG AAC ATC TCC CTG ACA AGC CTC ATA GCG AAG ATC CTT GAG TAT         4454
Ile Val Asn Ile Ser Leu Thr Ser Leu Ile Ala Lys Ile Leu Glu Tyr
            1405                1410                1415

TCC GAC GTG GCG TCC ATC AAA GCC CTT CGG ACT CTC CGT GCC CTC CGA         4502
Ser Asp Val Ala Ser Ile Lys Ala Leu Arg Thr Leu Arg Ala Leu Arg
            1420                1425                1430

CCG CTG CGG GCT CTG TCT CGA TTC GAA GGC ATG AGG GTA GTG GTG GAT         4550
Pro Leu Arg Ala Leu Ser Arg Phe Glu Gly Met Arg Val Val Val Asp
            1435                1440                1445

GCC CTC GTG GGC GCC ATC CCC TCC ATC ATG AAC GTC CTC CTC GTC TGC         4598
Ala Leu Val Gly Ala Ile Pro Ser Ile Met Asn Val Leu Leu Val Cys
```

```
                    -continued
1450             1455             1460             1465

CTC ATC TTC TGG CTC ATC TTC AGC ATC ATG GGC GTG AAC CTC TTC GCC    4646
Leu Ile Phe Trp Leu Ile Phe Ser Ile Met Gly Val Asn Leu Phe Ala
            1470             1475             1480

GGG AAA TTT TCG AAG TGC GTC GAC ACC AGA AAT AAC CCA TTT TCC AAC    4694
Gly Lys Phe Ser Lys Cys Val Asp Thr Arg Asn Asn Pro Phe Ser Asn
            1485             1490             1495

GTG AAT TCG ACG ATG GTG AAT AAC AAG TCC GAG TGT CAC AAT CAA AAC    4742
Val Asn Ser Thr Met Val Asn Asn Lys Ser Glu Cys His Asn Gln Asn
            1500             1505             1510

AGC ACC GGC CAC TTC TTC TGG GTC AAC GTC AAA GTC AAC TTC GAC AAC    4790
Ser Thr Gly His Phe Phe Trp Val Asn Val Lys Val Asn Phe Asp Asn
            1515             1520             1525

GTC GCT ATG GGC TAC CTC GCA CTT CTT CAG GTG GCA ACC TTC AAA GGC    4838
Val Ala Met Gly Tyr Leu Ala Leu Leu Gln Val Ala Thr Phe Lys Gly
1530             1535             1540             1545

TGG ATG GAC ATA ATG TAT GCA GCT GTT GAT TCC GGA GAG ATC AAC AGT    4886
Trp Met Asp Ile Met Tyr Ala Ala Val Asp Ser Gly Glu Ile Asn Ser
            1550             1555             1560

CAG CCT AAC TGG GAG AAC AAC TTG TAC ATG TAC CTG TAC TTC GTC GTT    4934
Gln Pro Asn Trp Glu Asn Asn Leu Tyr Met Tyr Leu Tyr Phe Val Val
            1565             1570             1575

TTC ATC ATT TTC GGT GGC TTC TTC ACG CTG AAT CTC TTT GTT GGG GTC    4982
Phe Ile Ile Phe Gly Gly Phe Phe Thr Leu Asn Leu Phe Val Gly Val
            1580             1585             1590

ATA ATC GAC AAC TTC AAC CAA CAG AAA AAA AAG CTA GGA GGC CAG GAC    5030
Ile Ile Asp Asn Phe Asn Gln Gln Lys Lys Lys Leu Gly Gly Gln Asp
            1595             1600             1605

ATC TTC ATG ACA GAA GAG CAG AAG AAG TAC TAC AAT GCC ATG AAG AAG    5078
Ile Phe Met Thr Glu Glu Gln Lys Lys Tyr Tyr Asn Ala Met Lys Lys
1610             1615             1620             1625

CTG GGC TCC AAG AAA CCC CAG AAG CCC ATC CCA CGG CCC CTG AAT AAG    5126
Leu Gly Ser Lys Lys Pro Gln Lys Pro Ile Pro Arg Pro Leu Asn Lys
            1630             1635             1640

TAC CAA GGC TTC GTG TTT GAC ATC GTG ACC AGG CAA GCC TTT GAC ATC    5174
Tyr Gln Gly Phe Val Phe Asp Ile Val Thr Arg Gln Ala Phe Asp Ile
            1645             1650             1655

ATC ATC ATG GTT CTC ATC TGC CTC AAC ATG ATC ACC ATG ATG GTG GAG    5222
Ile Ile Met Val Leu Ile Cys Leu Asn Met Ile Thr Met Met Val Glu
            1660             1665             1670

ACC GAC GAG CAG GGC GAG GAG AAG ACG AAG GTT CTG GGC AGA ATC AAC    5270
Thr Asp Glu Gln Gly Glu Glu Lys Thr Lys Val Leu Gly Arg Ile Asn
            1675             1680             1685

CAG TTC TTT GTG GCC GTC TTC ACG GGC GAG TGT GTG ATG AAG ATG TTC    5318
Gln Phe Phe Val Ala Val Phe Thr Gly Glu Cys Val Met Lys Met Phe
1690             1695             1700             1705

GCC CTG CGA CAG TAC TAC TTC ACC AAC GGC TGG AAC GTG TTC GAC TTC    5366
Ala Leu Arg Gln Tyr Tyr Phe Thr Asn Gly Trp Asn Val Phe Asp Phe
            1710             1715             1720

ATA GTG GTG ATC CTG TCC ATT GGG AGT CTG CTG TTT TCT GCA ATC CTT    5414
Ile Val Val Ile Leu Ser Ile Gly Ser Leu Leu Phe Ser Ala Ile Leu
            1725             1730             1735

AAG TCA CTG GAA AAC TAC TTC TCC CCG ACG CTC TTC CGG GTC ATC CGT    5462
Lys Ser Leu Glu Asn Tyr Phe Ser Pro Thr Leu Phe Arg Val Ile Arg
            1740             1745             1750

CTG GCC AGG ATC GGC CGC ATC CTC AGG CTG ATC CGA GCA GCC AAG GGG    5510
Leu Ala Arg Ile Gly Arg Ile Leu Arg Leu Ile Arg Ala Ala Lys Gly
            1755             1760             1765

ATT CGC ACG CTG CTC TTC GCC CTC ATG ATG TCC CTG CCC GCC CTC TTC    5558
```

```
Ile Arg Thr Leu Leu Phe Ala Leu Met Met Ser Leu Pro Ala Leu Phe
1770                1775                1780                1785

AAC ATC GGC CTC CTC CTC TTC CTC GTC ATG TTC ATC TAC TCC ATC TTC      5606
Asn Ile Gly Leu Leu Leu Phe Leu Val Met Phe Ile Tyr Ser Ile Phe
                    1790                1795                1800

GGC ATG GCC AGC TTC GCT AAC GTC GTG GAC GAG GCC GGC ATC GAC GAC      5654
Gly Met Ala Ser Phe Ala Asn Val Val Asp Glu Ala Gly Ile Asp Asp
            1805                1810                1815

ATG TTC AAC TTC AAG ACC TTT GGC AAC AGC ATG CTG TGC CTG TTC CAG      5702
Met Phe Asn Phe Lys Thr Phe Gly Asn Ser Met Leu Cys Leu Phe Gln
        1820                1825                1830

ATC ACC ACC TCG GCC GGC TGG GAC GGC CTC CTC AGC CCC ATC CTC AAC      5750
Ile Thr Thr Ser Ala Gly Trp Asp Gly Leu Leu Ser Pro Ile Leu Asn
    1835                1840                1845

ACG GGG CCT CCC TAC TGC GAC CCC AAC CTG CCC AAC AGC AAC GGC TCC      5798
Thr Gly Pro Pro Tyr Cys Asp Pro Asn Leu Pro Asn Ser Asn Gly Ser
1850                1855                1860                1865

CGG GGG AAC TGC GGG AGC CCG GCG GTG GGC ATC ATC TTC TTC ACC ACC      5846
Arg Gly Asn Cys Gly Ser Pro Ala Val Gly Ile Ile Phe Phe Thr Thr
                    1870                1875                1880

TAC ATC ATC ATC TCC TTC CTC ATC GTG GTC AAC ATG TAC ATC GCA GTG      5894
Tyr Ile Ile Ile Ser Phe Leu Ile Val Val Asn Met Tyr Ile Ala Val
                1885                1890                1895

ATT CTG GAG AAC TTC AAC GTA GCC ACC GAG GAG AGC ACG GAG CCC CTG      5942
Ile Leu Glu Asn Phe Asn Val Ala Thr Glu Glu Ser Thr Glu Pro Leu
            1900                1905                1910

AGC GAG GAC GAC TTC GAC ATG TTC TAT GAG ACC TGG GAG AAG TTC GAC      5990
Ser Glu Asp Asp Phe Asp Met Phe Tyr Glu Thr Trp Glu Lys Phe Asp
        1915                1920                1925

CCG GAG GCC ACC CAG TTC ATT GCC TTT TCT GCC CTC TCA GAC TTC GCG      6038
Pro Glu Ala Thr Gln Phe Ile Ala Phe Ser Ala Leu Ser Asp Phe Ala
1930                1935                1940                1945

GAC ACG CTC TCC GGC CCT CTT AGA ATC CCC AAA CCC AAC CAG AAT ATA      6086
Asp Thr Leu Ser Gly Pro Leu Arg Ile Pro Lys Pro Asn Gln Asn Ile
                    1950                1955                1960

TTA ATC CAG ATG GAC CTG CCG TTG GTC CCC GGG GAT AAG ATC CAC TGT      6134
Leu Ile Gln Met Asp Leu Pro Leu Val Pro Gly Asp Lys Ile His Cys
                1965                1970                1975

CTG GAC ATC CTT TTT GCC TTC ACA AAG AAC GTC TTG GGA GAA TCC GGG      6182
Leu Asp Ile Leu Phe Ala Phe Thr Lys Asn Val Leu Gly Glu Ser Gly
            1980                1985                1990

GAG TTG GAC TCC CTG AAG ACC AAT ATG GAA GAG AAG TTT ATG GCG ACC      6230
Glu Leu Asp Ser Leu Lys Thr Asn Met Glu Glu Lys Phe Met Ala Thr
        1995                2000                2005

AAT CTC TCC AAA GCA TCC TAT GAA CCA ATA GCC ACC ACC CTC CGG TGG      6278
Asn Leu Ser Lys Ala Ser Tyr Glu Pro Ile Ala Thr Thr Leu Arg Trp
2010                2015                2020                2025

AAG CAG GAA GAC CTC TCA GCC ACA GTC ATT CAA AAG GCC TAC CGG AGC      6326
Lys Gln Glu Asp Leu Ser Ala Thr Val Ile Gln Lys Ala Tyr Arg Ser
                    2030                2035                2040

TAC ATG CTG CAC CGC TCC TTG ACA CTC TCC AAC ACC CTG CAT GTG CCC      6374
Tyr Met Leu His Arg Ser Leu Thr Leu Ser Asn Thr Leu His Val Pro
                2045                2050                2055

AGG GCT GAG GAG GAT GGC GTG TCA CTT CCC GGG GAA GGC TAC AGT ACA      6422
Arg Ala Glu Glu Asp Gly Val Ser Leu Pro Gly Glu Gly Tyr Ser Thr
            2060                2065                2070

TTC ATG GCA AAC AGT GGA CTC CCG GAC AAA TCA GAA ACT GCC TCT GCT      6470
Phe Met Ala Asn Ser Gly Leu Pro Asp Lys Ser Glu Thr Ala Ser Ala
        2075                2080                2085
```

```
ACG TCT TTC CCG CCA TCC TAT GAC AGT GTC ACC AGG GGC CTG AGT GAC      6518
Thr Ser Phe Pro Pro Ser Tyr Asp Ser Val Thr Arg Gly Leu Ser Asp
2090                2095                2100                2105

CGG GCC AAC ATT AAC CCA TCT AGC TCA ATG CAA AAT GAA GAT GAG GTC      6566
Arg Ala Asn Ile Asn Pro Ser Ser Ser Met Gln Asn Glu Asp Glu Val
                2110                2115                2120

GCT GCT AAG GAA GGA AAC AGC CCT GGA CCT CAG TGAAGGCACT CAGGCATGCA    6619
Ala Ala Lys Glu Gly Asn Ser Pro Gly Pro Gln
            2125                2130

CAGGGCAGGT TCCAATGTCT TTCTCTGCTG TACTAACTCC TTCCCTCTGG AGGTGGCACC    6679

AACCTCCAGC CTCCACCAAT GCATGTCACT GGTCATGGTG TCAGAACTGA ATGGGACAT     6739

CCTTGAGAAA GCCCCCACCC CAATAGGAAT CAAAAGCCAA GGATACTCCT CCATTCTGAC    6799

GTCCCTTCCG AGTTCCCAGA AGATGTCATT GCTCCCTTCT GTTTGTGACC AGAGACGTGA    6859

TTCACCAACT TCTCGGAGCC AGAGACACAT AGCAAAGACT TTTCTGCTGG TGTCGGGCAG    6919

TCTTAGAGAA GTCACGTAGG GGTTGGTACT GAGAATTAGG GTTTGCATGA CTGCATGCTC    6979

ACAGCTGCCG GACAATACCT GTGAGTCGGC CATTAAAATT AATATTTTTA AAGTTAAAAA    7039

AAAAAAAAAA AAA                                                       7052

(2) INFORMATION FOR SEQ ID NO:6:

(i) SEQUENCE CHARACTERISTICS:
        (A) LENGTH: 2132 amino acids
        (B) TYPE: amino acid
        (D) TOPOLOGY: linear (ii) MOLECULE TYPE: protein (xi) SEQUENCE DESCRIPTION: SEQ ID NO:6:

Met Glu Leu Pro Phe Ala Ser Val Gly Thr Thr Asn Phe Arg Arg Phe
  1               5                  10                  15

Thr Pro Glu Ser Leu Ala Glu Ile Glu Lys Gln Ile Ala Ala His Arg
                 20                  25                  30

Ala Ala Lys Lys Ala Arg Thr Lys His Arg Gly Gln Glu Asp Lys Gly
            35                  40                  45

Glu Lys Pro Arg Pro Gln Leu Asp Leu Lys Asp Cys Asn Gln Leu Pro
 50                  55                  60

Lys Phe Tyr Gly Glu Leu Pro Ala Glu Leu Val Gly Glu Pro Leu Glu
 65                  70                  75                  80

Asp Leu Asp Pro Phe Tyr Ser Thr His Arg Thr Phe Met Val Leu Asn
                 85                  90                  95

Lys Ser Arg Thr Ile Ser Arg Phe Ser Ala Thr Trp Ala Leu Trp Leu
                100                 105                 110

Phe Ser Pro Phe Asn Leu Ile Arg Arg Thr Ala Ile Lys Val Ser Val
            115                 120                 125

His Ser Trp Phe Ser Ile Phe Ile Thr Ile Thr Ile Leu Val Asn Cys
130                 135                 140

Val Cys Met Thr Arg Thr Asp Leu Pro Glu Lys Val Glu Tyr Val Phe
145                 150                 155                 160

Thr Val Ile Tyr Thr Phe Glu Ala Leu Ile Lys Ile Leu Ala Arg Gly
                165                 170                 175

Phe Cys Leu Asn Glu Phe Thr Tyr Leu Arg Asp Pro Trp Asn Trp Leu
            180                 185                 190

Asp Phe Ser Val Ile Thr Leu Ala Tyr Val Gly Ala Ala Ile Asp Leu
            195                 200                 205
```

```
Arg Gly Ile Ser Gly Leu Arg Thr Phe Arg Val Leu Arg Ala Leu Lys
    210                 215                 220

Thr Val Ser Val Ile Pro Gly Leu Lys Val Ile Val Gly Ala Leu Ile
225                 230                 235                 240

His Ser Val Arg Lys Leu Ala Asp Val Thr Ile Leu Thr Val Phe Cys
                245                 250                 255

Leu Ser Val Phe Ala Leu Val Gly Leu Gln Leu Phe Lys Gly Asn Leu
                260                 265                 270

Lys Asn Lys Cys Ile Arg Asn Gly Thr Asp Pro His Lys Ala Asp Asn
            275                 280                 285

Leu Ser Ser Glu Met Ala Glu Tyr Ile Phe Ile Lys Pro Gly Thr Thr
    290                 295                 300

Asp Pro Leu Leu Cys Gly Asn Gly Ser Asp Ala Gly His Cys Pro Gly
305                 310                 315                 320

Gly Tyr Val Cys Leu Lys Thr Pro Asp Asn Pro Asp Phe Asn Tyr Thr
                325                 330                 335

Ser Phe Asp Ser Phe Ala Trp Ala Phe Leu Ser Leu Phe Arg Leu Met
                340                 345                 350

Thr Gln Asp Ser Trp Glu Arg Leu Tyr Gln Gln Thr Leu Arg Ala Ser
            355                 360                 365

Gly Lys Met Tyr Met Val Phe Phe Val Leu Val Ile Phe Leu Gly Ser
    370                 375                 380

Phe Tyr Leu Val Asn Leu Ile Leu Ala Val Val Thr Met Ala Tyr Glu
385                 390                 395                 400

Glu Gln Ser Gln Ala Thr Ile Ala Glu Ile Glu Ala Lys Glu Lys Lys
                405                 410                 415

Phe Gln Glu Ala Leu Glu Val Leu Gln Lys Glu Gln Glu Val Leu Ala
                420                 425                 430

Ala Leu Gly Ile Asp Thr Thr Ser Leu Gln Ser His Ser Gly Ser Pro
            435                 440                 445

Leu Ala Ser Lys Asn Ala Asn Glu Arg Arg Pro Arg Val Lys Ser Arg
    450                 455                 460

Val Ser Glu Gly Ser Thr Asp Asp Asn Arg Ser Pro Gln Ser Asp Pro
465                 470                 475                 480

Tyr Asn Gln Arg Arg Met Ser Phe Leu Gly Leu Ser Ser Gly Arg Arg
                485                 490                 495

Arg Ala Ser His Gly Ser Val Phe His Phe Arg Ala Pro Ser Gln Asp
            500                 505                 510

Ile Ser Phe Pro Asp Gly Ile Thr Pro Asp Asp Gly Val Phe His Gly
    515                 520                 525

Asp Gln Glu Ser Arg Arg Gly Ser Ile Leu Leu Gly Arg Gly Ala Gly
530                 535                 540

Gln Thr Gly Pro Leu Pro Arg Ser Pro Leu Pro Gln Ser Pro Asn Pro
545                 550                 555                 560

Gly Arg Arg His Gly Glu Glu Gly Gln Leu Gly Val Pro Thr Gly Glu
                565                 570                 575

Leu Thr Ala Gly Ala Pro Glu Gly Pro Ala Leu Asp Thr Thr Gly Gln
                580                 585                 590

Lys Ser Phe Leu Ser Ala Gly Tyr Leu Asn Glu Pro Phe Arg Ala Gln
            595                 600                 605

Arg Ala Met Ser Val Val Ser Ile Met Thr Ser Val Ile Glu Glu Leu
            610                 615                 620

Glu Glu Ser Lys Leu Lys Cys Pro Pro Cys Leu Ile Ser Phe Ala Gln
```

-continued

```
625                 630                 635                 640
Lys Tyr Leu Ile Trp Glu Cys Cys Pro Lys Trp Arg Lys Phe Lys Met
                645                 650                 655

Ala Leu Phe Glu Leu Val Thr Asp Pro Phe Ala Glu Leu Thr Ile Thr
                660                 665                 670

Leu Cys Ile Val Val Asn Thr Val Phe Met Ala Met Glu His Tyr Pro
                675                 680                 685

Met Thr Asp Ala Phe Asp Ala Met Leu Gln Ala Gly Asn Ile Val Phe
                690                 695                 700

Thr Val Phe Phe Thr Met Glu Met Ala Phe Lys Ile Ile Ala Phe Asp
705                 710                 715                 720

Pro Tyr Tyr Tyr Phe Gln Lys Lys Trp Asn Ile Phe Asp Cys Val Ile
                725                 730                 735

Val Thr Val Ser Leu Leu Glu Leu Ser Ala Ser Lys Lys Gly Ser Leu
                740                 745                 750

Ser Val Leu Arg Ser Leu Arg Leu Ala Leu Asp Thr Thr Gly Gln Lys
                755                 760                 765

Ser Phe Leu Ser Ala Gly Tyr Leu Asn Glu Pro Phe Arg Ala Gln Arg
                770                 775                 780

Ala Met Ser Val Val Ser Ile Met Thr Ser Val Ile Glu Glu Leu Glu
785                 790                 795                 800

Glu Ser Lys Leu Lys Cys Pro Pro Cys Leu Ile Ser Phe Ala Gln Lys
                805                 810                 815

Tyr Leu Ile Trp Glu Cys Cys Pro Lys Trp Arg Lys Phe Lys Met Ala
                820                 825                 830

Leu Phe Glu Leu Val Thr Asp Pro Phe Ala Glu Leu Thr Ile Thr Leu
                835                 840                 845

Cys Ile Val Val Asn Thr Val Phe Met Ala Met Glu His Tyr Pro Met
850                 855                 860

Thr Asp Ala Phe Asp Ala Met Leu Gln Ala Gly Asn Ile Val Phe Thr
865                 870                 875                 880

Val Phe Phe Thr Met Glu Met Ala Phe Lys Ile Ile Ala Phe Asp Pro
                885                 890                 895

Tyr Tyr Tyr Phe Gln Lys Lys Trp Asn Ile Phe Asp Cys Val Ile Val
                900                 905                 910

Thr Val Ser Leu Leu Glu Leu Ser Ala Ser Lys Lys Gly Ser Leu Ser
                915                 920                 925

Val Leu Arg Ser Leu Arg Leu Leu Arg Val Phe Lys Leu Ala Lys Ser
                930                 935                 940

Trp Pro Thr Leu Asn Thr Leu Ile Lys Ile Ile Gly Asn Ser Val Gly
945                 950                 955                 960

Ala Leu Gly Asn Leu Thr Phe Ile Leu Ala Ile Ile Val Phe Ile Phe
                965                 970                 975

Ala Leu Val Gly Lys Gln Leu Leu Ser Glu Asp Tyr Gly Cys Arg Lys
                980                 985                 990

Asp Gly Val Ser Val Trp Asn Gly Glu Lys Leu Arg Trp His Met Cys
                995                 1000                1005

Asp Phe Phe His Ser Phe Leu Val Val Phe Arg Ile Leu Cys Gly Glu
                1010                1015                1020

Trp Ile Glu Asn Met Trp Val Cys Met Glu Val Ser Gln Lys Ser Ile
1025                1030                1035                1040

Cys Leu Ile Leu Phe Leu Thr Val Met Val Leu Gly Asn Leu Val Val
                1045                1050                1055
```

-continued

Leu Asn Leu Phe Ile Ala Leu Leu Asn Ser Phe Ser Ala Asp Asn
              1060                1065                1070

Leu Thr Ala Pro Glu Asp Gly Glu Val Asn Asn Leu Gln Leu Ala
        1075                1080                1085

Leu Ala Arg Ile Gln Val Leu Gly His Arg Ala Ser Arg Ala Ile Ala
        1090                1095                1100

Ser Tyr Ile Ser Ser His Cys Arg Phe Arg Trp Pro Lys Val Glu Thr
1105                1110                1115                1120

Gln Leu Gly Met Lys Pro Pro Leu Thr Ser Ser Glu Ala Lys Asn His
                1125                1130                1135

Ile Ala Thr Asp Ala Val Ser Ala Ala Val Gly Asn Leu Thr Lys Pro
                1140                1145                1150

Ala Leu Ser Ser Pro Lys Glu Asn His Gly Asp Phe Ile Thr Asp Pro
                1155                1160                1165

Asn Val Trp Val Ser Val Pro Ile Ala Glu Gly Glu Ser Asp Leu Asp
            1170                1175                1180

Glu Leu Glu Glu Asp Met Glu Gln Ala Ser Gln Ser Ser Trp Gln Glu
1185                1190                1195                1200

Glu Asp Pro Lys Gly Gln Gln Glu Gln Leu Pro Gln Val Gln Lys Cys
                1205                1210                1215

Glu Asn His Gln Ala Ala Arg Ser Pro Ala Ser Met Met Ser Ser Glu
                1220                1225                1230

Asp Leu Ala Pro Tyr Leu Gly Ser Trp Lys Arg Lys Asp Ser Pro
            1235                1240                1245

Gln Val Pro Ala Glu Gly Val Asp Asp Thr Ser Ser Ser Glu Gly Ser
        1250                1255                1260

Thr Val Asp Cys Pro Asp Pro Glu Glu Ile Leu Arg Lys Ile Pro Glu
1265                1270                1275                1280

Leu Ala Asp Asp Leu Asp Glu Pro Asp Asp Cys Phe Thr Glu Gly Cys
                1285                1290                1295

Thr Arg Arg Cys Pro Cys Cys Asn Val Asn Thr Ser Lys Ser Pro Trp
            1300                1305                1310

Ala Thr Gly Trp Gln Val Arg Lys Thr Cys Tyr Arg Ile Val Glu His
            1315                1320                1325

Ser Trp Phe Glu Ser Phe Ile Ile Phe Met Ile Leu Leu Ser Ser Gly
        1330                1335                1340

Ala Leu Ala Phe Glu Asp Asn Tyr Leu Glu Glu Lys Pro Arg Val Lys
1345                1350                1355                1360

Ser Val Leu Glu Tyr Thr Asp Arg Val Phe Thr Phe Ile Phe Val Phe
                1365                1370                1375

Glu Met Leu Leu Lys Trp Val Ala Tyr Gly Phe Lys Lys Tyr Phe Thr
                1380                1385                1390

Asn Ala Trp Cys Trp Leu Asp Phe Leu Ile Val Asn Ile Ser Leu Thr
                1395                1400                1405

Ser Leu Ile Ala Lys Ile Leu Glu Tyr Ser Asp Val Ala Ser Ile Lys
        1410                1415                1420

Ala Leu Arg Thr Leu Arg Ala Leu Arg Pro Leu Arg Ala Leu Ser Arg
1425                1430                1435                1440

Phe Glu Gly Met Arg Val Val Asp Ala Leu Val Gly Ala Ile Pro
            1445                1450                1455

Ser Ile Met Asn Val Leu Leu Val Cys Leu Ile Phe Trp Leu Ile Phe
        1460                1465                1470

```
                            -continued

Ser Ile Met Gly Val Asn Leu Phe Ala Gly Lys Phe Ser Lys Cys Val
            1475                1480                1485

Asp Thr Arg Asn Asn Pro Phe Ser Asn Val Asn Ser Thr Met Val Asn
        1490                1495                1500

Asn Lys Ser Glu Cys His Asn Gln Asn Ser Thr Gly His Phe Phe Trp
1505                1510                1515                1520

Val Asn Val Lys Val Asn Phe Asp Asn Val Ala Met Gly Tyr Leu Ala
            1525                1530                1535

Leu Leu Gln Val Ala Thr Phe Lys Gly Trp Met Asp Ile Met Tyr Ala
            1540                1545                1550

Ala Val Asp Ser Gly Glu Ile Asn Ser Gln Pro Asn Trp Glu Asn Asn
            1555                1560                1565

Leu Tyr Met Tyr Leu Tyr Phe Val Val Phe Ile Ile Phe Gly Gly Phe
            1570                1575                1580

Phe Thr Leu Asn Leu Phe Val Gly Val Ile Ile Asp Asn Phe Asn Gln
1585                1590                1595                1600

Gln Lys Lys Lys Leu Gly Gly Gln Asp Ile Phe Met Thr Glu Glu Gln
            1605                1610                1615

Lys Lys Tyr Tyr Asn Ala Met Lys Lys Leu Gly Ser Lys Lys Pro Gln
            1620                1625                1630

Lys Pro Ile Pro Arg Pro Leu Asn Lys Tyr Gln Gly Phe Val Phe Asp
            1635                1640                1645

Ile Val Thr Arg Gln Ala Phe Asp Ile Ile Met Val Leu Ile Cys
            1650                1655                1660

Leu Asn Met Ile Thr Met Met Val Glu Thr Asp Glu Gln Gly Glu Glu
1665                1670                1675                1680

Lys Thr Lys Val Leu Gly Arg Ile Asn Gln Phe Phe Val Ala Val Phe
            1685                1690                1695

Thr Gly Glu Cys Val Met Lys Met Phe Ala Leu Arg Gln Tyr Tyr Phe
            1700                1705                1710

Thr Asn Gly Trp Asn Val Phe Asp Phe Ile Val Val Ile Leu Ser Ile
            1715                1720                1725

Gly Ser Leu Leu Phe Ser Ala Ile Leu Lys Ser Leu Glu Asn Tyr Phe
            1730                1735                1740

Ser Pro Thr Leu Phe Arg Val Ile Arg Leu Ala Arg Ile Gly Arg Ile
1745                1750                1755                1760

Leu Arg Leu Ile Arg Ala Ala Lys Gly Ile Arg Thr Leu Leu Phe Ala
            1765                1770                1775

Leu Met Met Ser Leu Pro Ala Leu Phe Asn Ile Gly Leu Leu Leu Phe
            1780                1785                1790

Leu Val Met Phe Ile Tyr Ser Ile Phe Gly Met Ala Ser Phe Ala Asn
            1795                1800                1805

Val Val Asp Glu Ala Gly Ile Asp Asp Met Phe Asn Phe Lys Thr Phe
            1810                1815                1820

Gly Asn Ser Met Leu Cys Leu Phe Gln Ile Thr Thr Ser Ala Gly Trp
1825                1830                1835                1840

Asp Gly Leu Leu Ser Pro Ile Leu Asn Thr Gly Pro Pro Tyr Cys Asp
            1845                1850                1855

Pro Asn Leu Pro Asn Ser Asn Gly Ser Arg Gly Asn Cys Gly Ser Pro
            1860                1865                1870

Ala Val Gly Ile Ile Phe Phe Thr Thr Tyr Ile Ile Ser Phe Leu
            1875                1880                1885

Ile Val Val Asn Met Tyr Ile Ala Val Ile Leu Glu Asn Phe Asn Val
```

```
                    1890                  1895                 1900
Ala Thr Glu Glu Ser Thr Glu Pro Leu Ser Glu Asp Asp Phe Asp Met
1905                 1910                 1915                 1920

Phe Tyr Glu Thr Trp Glu Lys Phe Asp Pro Ala Thr Gln Phe Ile
                    1925                 1930                 1935

Ala Phe Ser Ala Leu Ser Asp Phe Ala Asp Thr Leu Ser Gly Pro Leu
               1940                 1945                 1950

Arg Ile Pro Lys Pro Asn Gln Asn Ile Leu Ile Gln Met Asp Leu Pro
          1955                 1960                 1965

Leu Val Pro Gly Asp Lys Ile His Cys Leu Asp Ile Leu Phe Ala Phe
     1970                 1975                 1980

Thr Lys Asn Val Leu Gly Glu Ser Gly Glu Leu Asp Ser Leu Lys Thr
1985                 1990                 1995                 2000

Asn Met Glu Glu Lys Phe Met Ala Thr Asn Leu Ser Lys Ala Ser Tyr
                    2005                 2010                 2015

Glu Pro Ile Ala Thr Thr Leu Arg Trp Lys Gln Glu Asp Leu Ser Ala
               2020                 2025                 2030

Thr Val Ile Gln Lys Ala Tyr Arg Ser Tyr Met Leu His Arg Ser Leu
          2035                 2040                 2045

Thr Leu Ser Asn Thr Leu His Val Pro Arg Ala Glu Glu Asp Gly Val
     2050                 2055                 2060

Ser Leu Pro Gly Glu Gly Tyr Ser Thr Phe Met Ala Asn Ser Gly Leu
2065                 2070                 2075                 2080

Pro Asp Lys Ser Glu Thr Ala Ser Ala Thr Ser Phe Pro Pro Ser Tyr
                    2085                 2090                 2095

Asp Ser Val Thr Arg Gly Leu Ser Asp Arg Ala Asn Ile Asn Pro Ser
               2100                 2105                 2110

Ser Ser Met Gln Asn Glu Asp Glu Val Ala Ala Lys Glu Gly Asn Ser
          2115                 2120                 2125

Pro Gly Pro Gln
     2130

(2) INFORMATION FOR SEQ ID NO:7:

(i) SEQUENCE CHARACTERISTICS:
        (A) LENGTH: 6527 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 204..6077

(xi) SEQUENCE DESCRIPTION: SEQ ID NO:7:

TAGCTTGCTT CTGCTAATGC TACCCCAGGC CTTTAGACAG AGAACAGATG GCAGATGGAG      60

TTTCTTATTG CCATGCGCAA ACGCTGAGCC CACCTCATGA TCCCGGACCC CATGGTTTTC     120

AGTAGACAAC CTGGGCTAAG AAGAGATCTC CGACCTTATA GAGCAGCAAA GAGTGTAAAT     180

TCTTCCCCAA GAAGAATGAG AAG ATG GAG CTC CCC TTT GCG TCC GTG GGA        230
                          Met Glu Leu Pro Phe Ala Ser Val Gly
                           1               5

ACT ACC AAT TTC AGA CGG TTC ACT CCA GAG TCA CTG GCA GAG ATC GAG      278
Thr Thr Asn Phe Arg Arg Phe Thr Pro Glu Ser Leu Ala Glu Ile Glu
 10                  15                  20                  25

AAG CAG ATT GCT GCT CAC CGG GCA GCC AAG AAG GCC AGA ACC AAG CAC      326
```

-continued

```
                Lys Gln Ile Ala Ala His Arg Ala Ala Lys Lys Ala Arg Thr Lys His
                                30                  35                  40

AGA GGA CAG GAG GAC AAG GGC GAG AAG CCC AGG CCT CAG CTG GAC TTG           374
Arg Gly Gln Glu Asp Lys Gly Glu Lys Pro Arg Pro Gln Leu Asp Leu
            45                  50                  55

AAA GAC TGT AAC CAG CTG CCC AAG TTC TAT GGT GAG CTC CCA GCA GAA           422
Lys Asp Cys Asn Gln Leu Pro Lys Phe Tyr Gly Glu Leu Pro Ala Glu
        60                  65                  70

CTG GTC GGG GAG CCC CTG GAG GAC CTA GAC CCT TTC TAC AGC ACA CAC           470
Leu Val Gly Glu Pro Leu Glu Asp Leu Asp Pro Phe Tyr Ser Thr His
    75                  80                  85

CGG ACA TTC ATG GTG TTG AAT AAA AGC AGG ACC ATT TCC AGA TTC AGT           518
Arg Thr Phe Met Val Leu Asn Lys Ser Arg Thr Ile Ser Arg Phe Ser
 90                  95                 100                 105

GCC ACT TGG GCC CTG TGG CTC TTC AGT CCC TTC AAC CTG ATC AGA AGA           566
Ala Thr Trp Ala Leu Trp Leu Phe Ser Pro Phe Asn Leu Ile Arg Arg
                110                 115                 120

ACA GCC ATC AAA GTG TCT GTC CAT TCC TGG TTC TCC ATA TTC ATC ACC           614
Thr Ala Ile Lys Val Ser Val His Ser Trp Phe Ser Ile Phe Ile Thr
            125                 130                 135

ATC ACT ATT TTG GTC AAC TGC GTG TGC ATG ACC CGA ACT GAT CTT CCA           662
Ile Thr Ile Leu Val Asn Cys Val Cys Met Thr Arg Thr Asp Leu Pro
        140                 145                 150

GAG AAA GTC GAG TAC GTC TTC ACT GTC ATT TAC ACC TTC GAG GCT CTG           710
Glu Lys Val Glu Tyr Val Phe Thr Val Ile Tyr Thr Phe Glu Ala Leu
    155                 160                 165

ATT AAG ATA CTG GCA AGA GGG TTT TGT CTA AAT GAG TTC ACT TAT CTT           758
Ile Lys Ile Leu Ala Arg Gly Phe Cys Leu Asn Glu Phe Thr Tyr Leu
170                 175                 180                 185

CGA GAT CCG TGG AAC TGG CTG GAC TTC AGT GTC ATT ACC TTG GCG TAT           806
Arg Asp Pro Trp Asn Trp Leu Asp Phe Ser Val Ile Thr Leu Ala Tyr
                190                 195                 200

GTG GGT GCA GCG ATA GAC CTC CGA GGA ATC TCA GGC CTG CGG ACA TTC           854
Val Gly Ala Ala Ile Asp Leu Arg Gly Ile Ser Gly Leu Arg Thr Phe
            205                 210                 215

CGA GTT CTC AGA GCC CTG AAA ACT GTT TCT GTG ATC CCA GGA CTG AAG           902
Arg Val Leu Arg Ala Leu Lys Thr Val Ser Val Ile Pro Gly Leu Lys
        220                 225                 230

GTC ATC GTG GGA GCC CTG ATC CAC TCA GTG AGG AAG CTG GCC GAC GTG           950
Val Ile Val Gly Ala Leu Ile His Ser Val Arg Lys Leu Ala Asp Val
    235                 240                 245

ACT ATC CTC ACA GTC TTC TGC CTG AGC GTC TTC GCC TTG GTG GGC CTG           998
Thr Ile Leu Thr Val Phe Cys Leu Ser Val Phe Ala Leu Val Gly Leu
250                 255                 260                 265

CAG CTC TTT AAG GGG AAC CTT AAG AAC AAA TGC ATC AGG AAC GGA ACA          1046
Gln Leu Phe Lys Gly Asn Leu Lys Asn Lys Cys Ile Arg Asn Gly Thr
                270                 275                 280

GAT CCC CAC AAG GCT GAC AAC CTC TCA TCT GAA ATG GCA GAA TAC ATC          1094
Asp Pro His Lys Ala Asp Asn Leu Ser Ser Glu Met Ala Glu Tyr Ile
            285                 290                 295

TTC ATC AAG CCT GGT ACT ACG GAT CCC TTA CTG TGC GGC AAT GGG TCT          1142
Phe Ile Lys Pro Gly Thr Thr Asp Pro Leu Leu Cys Gly Asn Gly Ser
        300                 305                 310

GAT GCT GGT CAC TGC CCT GGA GGC TAT GTC TGC CTG AAA ACT CCT GAC          1190
Asp Ala Gly His Cys Pro Gly Gly Tyr Val Cys Leu Lys Thr Pro Asp
    315                 320                 325

AAC CCG GAT TTT AAC TAC ACC AGC TTT GAT TCC TTT GCG TGG GCA TTC          1238
Asn Pro Asp Phe Asn Tyr Thr Ser Phe Asp Ser Phe Ala Trp Ala Phe
330                 335                 340                 345
```

```
CTC TCA CTG TTC CGC CTC ATG ACG CAG GAC TCC TGG GAG CGC CTG TAC      1286
Leu Ser Leu Phe Arg Leu Met Thr Gln Asp Ser Trp Glu Arg Leu Tyr
                350                 355                 360

CAG CAG ACA CTC CGG GCT TCT GGG AAA ATG TAC ATG GTC TTT TTC GTG      1334
Gln Gln Thr Leu Arg Ala Ser Gly Lys Met Tyr Met Val Phe Phe Val
                365                 370                 375

CTG GTT ATT TTC CTT GGA TCG TTC TAC CTG GTC AAT TTG ATC TTG GCC      1382
Leu Val Ile Phe Leu Gly Ser Phe Tyr Leu Val Asn Leu Ile Leu Ala
                380                 385                 390

GTG GTC ACC ATG GCG TAT GAA GAG CAG AGC CAG GCA ACA ATT GCA GAA      1430
Val Val Thr Met Ala Tyr Glu Glu Gln Ser Gln Ala Thr Ile Ala Glu
        395                 400                 405

ATC GAA GCC AAG GAA AAA AAG TTC CAG GAA GCC CTT GAG GTG CTG CAG      1478
Ile Glu Ala Lys Glu Lys Lys Phe Gln Glu Ala Leu Glu Val Leu Gln
410                 415                 420                 425

AAG GAA CAG GAG GTG CTG GCA GCC CTG GGG ATT GAC ACG ACC TCG CTC      1526
Lys Glu Gln Glu Val Leu Ala Ala Leu Gly Ile Asp Thr Thr Ser Leu
                430                 435                 440

CAG TCC CAC AGT GGA TCA CCC TTA GCC TCC AAA AAC GCC AAT GAG AGA      1574
Gln Ser His Ser Gly Ser Pro Leu Ala Ser Lys Asn Ala Asn Glu Arg
                445                 450                 455

AGA CCC AGG GTG AAA TCA AGG GTG TCA GAG GGC TCC ACG GAT GAC AAC      1622
Arg Pro Arg Val Lys Ser Arg Val Ser Glu Gly Ser Thr Asp Asp Asn
        460                 465                 470

AGG TCA CCC CAA TCT GAC CCT TAC AAC CAG CGC AGG ATG TCT TTC CTA      1670
Arg Ser Pro Gln Ser Asp Pro Tyr Asn Gln Arg Arg Met Ser Phe Leu
475                 480                 485

GGC CTG TCT TCA GGA AGA CGC AGG GCT AGC CAC GGC AGT GTG TTC CAC      1718
Gly Leu Ser Ser Gly Arg Arg Arg Ala Ser His Gly Ser Val Phe His
490                 495                 500                 505

TTC CGA GCG CCC AGC CAA GAC ATC TCA TTT CCT GAC GGG ATC ACC CCT      1766
Phe Arg Ala Pro Ser Gln Asp Ile Ser Phe Pro Asp Gly Ile Thr Pro
                510                 515                 520

GAT GAT GGG GTC TTT CAC GGA GAC CAG GAA AGC CGT CGA GGT TCC ATA      1814
Asp Asp Gly Val Phe His Gly Asp Gln Glu Ser Arg Arg Gly Ser Ile
                525                 530                 535

TTG CTG GGC AGG GGT GCT GGG CAG ACA GGT CCA CTC CCC AGG AGC CCA      1862
Leu Leu Gly Arg Gly Ala Gly Gln Thr Gly Pro Leu Pro Arg Ser Pro
        540                 545                 550

CTG CCT CAG TCC CCC AAC CCT GGC CGT AGA CAT GGA GAA GAG GGA CAG      1910
Leu Pro Gln Ser Pro Asn Pro Gly Arg Arg His Gly Glu Glu Gly Gln
555                 560                 565

CTC GGA GTG CCC ACT GGT GAG CTT ACC GCT GGA GCG CCT GAA GGC CCG      1958
Leu Gly Val Pro Thr Gly Glu Leu Thr Ala Gly Ala Pro Glu Gly Pro
570                 575                 580                 585

GCA CTC GAC ACT ACA GGG CAG AAG AGC TTC CTG TCT GCG GGC TAC TTG      2006
Ala Leu Asp Thr Thr Gly Gln Lys Ser Phe Leu Ser Ala Gly Tyr Leu
                590                 595                 600

AAC GAA CCT TTC CGA GCA CAG AGG GCC ATG AGC GTT GTC AGT ATC ATG      2054
Asn Glu Pro Phe Arg Ala Gln Arg Ala Met Ser Val Val Ser Ile Met
                605                 610                 615

ACT TCT GTC ATT GAG GAG CTT GAA GAG TCT AAG CTG AAG TGC CCA CCC      2102
Thr Ser Val Ile Glu Glu Leu Glu Glu Ser Lys Leu Lys Cys Pro Pro
                620                 625                 630

TGC TTG ATC AGC TTC GCT CAG AAG TAT CTG ATC TGG GAG TGC TGC CCC      2150
Cys Leu Ile Ser Phe Ala Gln Lys Tyr Leu Ile Trp Glu Cys Cys Pro
        635                 640                 645

AAG TGG AGG AAG TTC AAG ATG GCG CTG TTC GAG CTG GTG ACT GAC CCC      2198
Lys Trp Arg Lys Phe Lys Met Ala Leu Phe Glu Leu Val Thr Asp Pro
650                 655                 660                 665
```

```
TTC GCA GAG CTT ACC ATC ACC CTC TGC ATC GTG GTG AAC ACC GTC TTC      2246
Phe Ala Glu Leu Thr Ile Thr Leu Cys Ile Val Val Asn Thr Val Phe
                670             675                 680

ATG GCC ATG GAG CAC TAC CCC ATG ACC GAT GCC TTC GAT GCC ATG CTT      2294
Met Ala Met Glu His Tyr Pro Met Thr Asp Ala Phe Asp Ala Met Leu
                685                 690                 695

CAA GCC GGC AAC ATT GTC TTC ACC GTG TTT TTC ACA ATG GAG ATG GCC      2342
Gln Ala Gly Asn Ile Val Phe Thr Val Phe Phe Thr Met Glu Met Ala
                700                 705                 710

TTC AAG ATC ATT GCC TTC GAC CCC TAC TAT TAC TTC CAG AAG AAG TGG      2390
Phe Lys Ile Ile Ala Phe Asp Pro Tyr Tyr Tyr Phe Gln Lys Lys Trp
    715                 720                 725

AAT ATC TTC GAC TGT GTC ATC GTC ACC GTG AGC CTT CTG GAG CTG AGT      2438
Asn Ile Phe Asp Cys Val Ile Val Thr Val Ser Leu Leu Glu Leu Ser
730                 735                 740                 745

GCA TCC AAG AAG GGC AGC CTG TCT GTG CTC CGT TCC TTA CGC TTG CTG      2486
Ala Ser Lys Lys Gly Ser Leu Ser Val Leu Arg Ser Leu Arg Leu Leu
                750                 755                 760

CGG GTC TTC AAG CTG GCC AAG TCC TGG CCC ACC CTG AAC ACC CTC ATC      2534
Arg Val Phe Lys Leu Ala Lys Ser Trp Pro Thr Leu Asn Thr Leu Ile
                765                 770                 775

AAG ATC ATC GGG AAC TCA GTG GGG GCC CTG GGC AAC CTG ACC TTT ATC      2582
Lys Ile Ile Gly Asn Ser Val Gly Ala Leu Gly Asn Leu Thr Phe Ile
                780                 785                 790

CTG GCC ATC ATC GTC TTC ATC TTC GCC CTG GTC GGA AAG CAG CTT CTC      2630
Leu Ala Ile Ile Val Phe Ile Phe Ala Leu Val Gly Lys Gln Leu Leu
        795                 800                 805

TCA GAG GAC TAC GGG TGC CGC AAG GAC GGC GTC TCC GTG TGG AAC GGC      2678
Ser Glu Asp Tyr Gly Cys Arg Lys Asp Gly Val Ser Val Trp Asn Gly
810                 815                 820                 825

GAG AAG CTC CGC TGG CAC ATG TGT GAC TTC TTC CAT TCC TTC CTG GTC      2726
Glu Lys Leu Arg Trp His Met Cys Asp Phe Phe His Ser Phe Leu Val
                830                 835                 840

GTC TTC CGA ATC CTC TGC GGG GAG TGG ATC GAG AAC ATG TGG GTC TGC      2774
Val Phe Arg Ile Leu Cys Gly Glu Trp Ile Glu Asn Met Trp Val Cys
            845                 850                 855

ATG GAG GTC AGC CAG AAA TCC ATC TGC CTC ATC CTC TTC TTG ACT GTG      2822
Met Glu Val Ser Gln Lys Ser Ile Cys Leu Ile Leu Phe Leu Thr Val
                860                 865                 870

ATG GTG CTG GGC AAC CTA GTG GTG CTC AAC CTT TTC ATC GCT TTA CTG      2870
Met Val Leu Gly Asn Leu Val Val Leu Asn Leu Phe Ile Ala Leu Leu
    875                 880                 885

CTG AAC TCC TTC AGC GCG GAC AAC CTC ACG GCT CCA GAG GAT GAC GGG      2918
Leu Asn Ser Phe Ser Ala Asp Asn Leu Thr Ala Pro Glu Asp Asp Gly
890                 895                 900                 905

GAG GTG AAC AAC TTG CAG TTA GCA CTG GCC AGG ATC CAG GTA CTT GGC      2966
Glu Val Asn Asn Leu Gln Leu Ala Leu Ala Arg Ile Gln Val Leu Gly
                910                 915                 920

CAT CGG GCC AGC AGG GCC ATC GCC AGT TAC ATC AGC AGC CAC TGC CGA      3014
His Arg Ala Ser Arg Ala Ile Ala Ser Tyr Ile Ser Ser His Cys Arg
                925                 930                 935

TTC CGC TGG CCC AAG GTG GAG ACC CAG CTG GGC ATG AAG CCC CCA CTC      3062
Phe Arg Trp Pro Lys Val Glu Thr Gln Leu Gly Met Lys Pro Pro Leu
            940                 945                 950

ACC AGC TCA GAG GCC AAG AAC CAC ATT GCC ACT GAT GCT GTC AGT GCT      3110
Thr Ser Ser Glu Ala Lys Asn His Ile Ala Thr Asp Ala Val Ser Ala
                955                 960                 965

GCA GTG GGG AAC CTG ACA AAG CCA GCT CTC AGT AGC CCC AAG GAG AAT      3158
Ala Val Gly Asn Leu Thr Lys Pro Ala Leu Ser Ser Pro Lys Glu Asn
```

```
                                                            -continued
970                   975                   980                   985

CAC GGG GAC TTC ATC ACT GAT CCC AAC GTG TGG GTC TCT GTG CCC ATT         3206
His Gly Asp Phe Ile Thr Asp Pro Asn Val Trp Val Ser Val Pro Ile
                990                   995                  1000

GCT GAG GGG GAA TCT GAC CTC GAC GAG CTC GAG GAA GAT ATG GAG CAG         3254
Ala Glu Gly Glu Ser Asp Leu Asp Glu Leu Glu Glu Asp Met Glu Gln
               1005                  1010                  1015

GCT TCG CAG AGC TCC TGG CAG GAA GAG GAC CCC AAG GGA CAG CAG GAG         3302
Ala Ser Gln Ser Ser Trp Gln Glu Glu Asp Pro Lys Gly Gln Gln Glu
               1020                  1025                  1030

CAG TTG CCA CAA GTC CAA AAG TGT GAA AAC CAC CAG GCA GCC AGA AGC         3350
Gln Leu Pro Gln Val Gln Lys Cys Glu Asn His Gln Ala Ala Arg Ser
               1035                  1040                  1045

CCA GCC TCC ATG ATG TCC TCT GAG GAC CTG GCT CCA TAC CTG GGT GAG         3398
Pro Ala Ser Met Met Ser Ser Glu Asp Leu Ala Pro Tyr Leu Gly Glu
1050                  1055                  1060                  1065

AGC TGG AAG AGG AAG GAT AGC CCT CAG GTC CCT GCC GAG GGA GTG GAT         3446
Ser Trp Lys Arg Lys Asp Ser Pro Gln Val Pro Ala Glu Gly Val Asp
               1070                  1075                  1080

GAC ACG AGC TCC TCT GAG GGC AGC ACG GTG GAC TGC CCG GAC CCA GAG         3494
Asp Thr Ser Ser Ser Glu Gly Ser Thr Val Asp Cys Pro Asp Pro Glu
               1085                  1090                  1095

GAA ATC CTG AGG AAG ATC CCC GAG CTG GCA GAT GAC CTG GAC GAG CCC         3542
Glu Ile Leu Arg Lys Ile Pro Glu Leu Ala Asp Asp Leu Asp Glu Pro
               1100                  1105                  1110

GAT GAC TGT TTC ACA GAA GGC TGC ACT CGC CGC TGT CCC TGC TGC AAC         3590
Asp Asp Cys Phe Thr Glu Gly Cys Thr Arg Arg Cys Pro Cys Cys Asn
               1115                  1120                  1125

GTG AAT ACT AGC AAG TCT CCT TGG GCC ACA GGC TGG CAG GTG CGC AAG         3638
Val Asn Thr Ser Lys Ser Pro Trp Ala Thr Gly Trp Gln Val Arg Lys
1130                  1135                  1140                  1145

ACC TGC TAC CGC ATC GTG GAG CAC AGC TGG TTT GAG AGT TTC ATC ATC         3686
Thr Cys Tyr Arg Ile Val Glu His Ser Trp Phe Glu Ser Phe Ile Ile
               1150                  1155                  1160

TTC ATG ATC CTG CTC AGC AGT GGA GCG CTG GCC TTT GAG GAT AAC TAC         3734
Phe Met Ile Leu Leu Ser Ser Gly Ala Leu Ala Phe Glu Asp Asn Tyr
               1165                  1170                  1175

CTG GAA GAG AAA CCC CGA GTG AAG TCC GTG CTG GAG TAC ACT GAC CGA         3782
Leu Glu Glu Lys Pro Arg Val Lys Ser Val Leu Glu Tyr Thr Asp Arg
               1180                  1185                  1190

GTG TTC ACC TTC ATC TTC GTC TTT GAG ATG CTG CTC AAG TGG GTA GCC         3830
Val Phe Thr Phe Ile Phe Val Phe Glu Met Leu Leu Lys Trp Val Ala
               1195                  1200                  1205

TAT GGC TTC AAA AAG TAT TTC ACC AAT GCC TGG TGC TGG CTG GAC TTC         3878
Tyr Gly Phe Lys Lys Tyr Phe Thr Asn Ala Trp Cys Trp Leu Asp Phe
1210                  1215                  1220                  1225

CTC ATT GTG AAC ATC TCC CTG ACA AGC CTC ATA GCG AAG ATC CTT GAG         3926
Leu Ile Val Asn Ile Ser Leu Thr Ser Leu Ile Ala Lys Ile Leu Glu
               1230                  1235                  1240

TAT TCC GAC GTG GCG TCC ATC AAA GCC CTT CGG ACT CTC CGT GCC CTC         3974
Tyr Ser Asp Val Ala Ser Ile Lys Ala Leu Arg Thr Leu Arg Ala Leu
               1245                  1250                  1255

CGA CCG CTG CGG GCT CTG TCT CGA TTC GAA GGC ATG AGG GTA GTG GTG         4022
Arg Pro Leu Arg Ala Leu Ser Arg Phe Glu Gly Met Arg Val Val Val
               1260                  1265                  1270

GAT GCC CTC GTG GGC GCC ATC CCC TCC ATC ATG AAC GTC CTC CTC GTC         4070
Asp Ala Leu Val Gly Ala Ile Pro Ser Ile Met Asn Val Leu Leu Val
               1275                  1280                  1285

TGC CTC ATC TTC TGG CTC ATC TTC AGC ATC ATG GGC GTG AAC CTC TTC         4118
```

```
Cys Leu Ile Phe Trp Leu Ile Phe Ser Ile Met Gly Val Asn Leu Phe
1290                1295                1300                1305

GCC GGG AAA TTT TCG AAG TGC GTC GAC ACC AGA AAT AAC CCA TTT TCC        4166
Ala Gly Lys Phe Ser Lys Cys Val Asp Thr Arg Asn Asn Pro Phe Ser
                1310                1315                1320

AAC GTG AAT TCG ACG ATG GTG AAT AAC AAG TCC GAG TGT CAC AAT CAA        4214
Asn Val Asn Ser Thr Met Val Asn Asn Lys Ser Glu Cys His Asn Gln
                1325                1330                1335

AAC AGC ACC GGC CAC TTC TTC TGG GTC AAC GTC AAA GTC AAC TTC GAC        4262
Asn Ser Thr Gly His Phe Phe Trp Val Asn Val Lys Val Asn Phe Asp
                1340                1345                1350

AAC GTC GCT ATG GGC TAC CTC GCA CTT CTT CAG GTG GCA ACC TTC AAA        4310
Asn Val Ala Met Gly Tyr Leu Ala Leu Leu Gln Val Ala Thr Phe Lys
                1355                1360                1365

GGC TGG ATG GAC ATA ATG TAT GCA GCT GTT GAT TCC GGA GAG ATC AAC        4358
Gly Trp Met Asp Ile Met Tyr Ala Ala Val Asp Ser Gly Glu Ile Asn
1370                1375                1380                1385

AGT CAG CCT AAC TGG GAG AAC AAC TTG TAC ATG TAC CTG TAC TTC GTC        4406
Ser Gln Pro Asn Trp Glu Asn Asn Leu Tyr Met Tyr Leu Tyr Phe Val
                1390                1395                1400

GTT TTC ATC ATT TTC GGT GGC TTC TTC ACG CTG AAT CTC TTT GTT GGG        4454
Val Phe Ile Ile Phe Gly Gly Phe Phe Thr Leu Asn Leu Phe Val Gly
                1405                1410                1415

GTC ATA ATC GAC AAC TTC AAC CAA CAG AAA AAA AAG CTA GGA GGC CAG        4502
Val Ile Ile Asp Asn Phe Asn Gln Gln Lys Lys Lys Leu Gly Gly Gln
                1420                1425                1430

GAC ATC TTC ATG ACA GAA GAG CAG AAG AAG TAC TAC AAT GCC ATG AAG        4550
Asp Ile Phe Met Thr Glu Glu Gln Lys Lys Tyr Tyr Asn Ala Met Lys
                1435                1440                1445

AAG CTG GGC TCC AAG AAA CCC CAG AAG CCC ATC CCA CGG CCC CTG AAT        4598
Lys Leu Gly Ser Lys Lys Pro Gln Lys Pro Ile Pro Arg Pro Leu Asn
1450                1455                1460                1465

AAG TAC CAA GGC TTC GTG TTT GAC ATC GTG ACC AGG CAA GCC TTT GAC        4646
Lys Tyr Gln Gly Phe Val Phe Asp Ile Val Thr Arg Gln Ala Phe Asp
                1470                1475                1480

ATC ATC ATC ATG GTT CTC ATC TGC CTC AAC ATG ATC ACC ATG ATG GTG        4694
Ile Ile Ile Met Val Leu Ile Cys Leu Asn Met Ile Thr Met Met Val
                1485                1490                1495

GAG ACC GAC GAG CAG GGC GAG GAG AAG ACG AAG GTT CTG GGC AGA ATC        4742
Glu Thr Asp Glu Gln Gly Glu Glu Lys Thr Lys Val Leu Gly Arg Ile
                1500                1505                1510

AAC CAG TTC TTT GTG GCC GTC TTC ACG GGC GAG TGT GTG ATG AAG ATG        4790
Asn Gln Phe Phe Val Ala Val Phe Thr Gly Glu Cys Val Met Lys Met
                1515                1520                1525

TTC GCC CTG CGA CAG TAC TAC TTC ACC AAC GGC TGG AAC GTG TTC GAC        4838
Phe Ala Leu Arg Gln Tyr Tyr Phe Thr Asn Gly Trp Asn Val Phe Asp
1530                1535                1540                1545

TTC ATA GTG GTG ATC CTG TCC ATT GGG AGT CTG CTG TTT TCT GCA ATC        4886
Phe Ile Val Val Ile Leu Ser Ile Gly Ser Leu Leu Phe Ser Ala Ile
                1550                1555                1560

CTT AAG TCA CTG GAA AAC TAC TTC TCC CCG ACG CTC TTC CGG GTC ATC        4934
Leu Lys Ser Leu Glu Asn Tyr Phe Ser Pro Thr Leu Phe Arg Val Ile
                1565                1570                1575

CGT CTG GCC AGG ATC GGC CGC ATC CTC AGG CTG ATC CGA GCA GCC AAG        4982
Arg Leu Ala Arg Ile Gly Arg Ile Leu Arg Leu Ile Arg Ala Ala Lys
                1580                1585                1590

GGG ATT CGC ACG CTG CTC TTC GCC CTC ATG ATG TCC CTG CCC GCC CTC        5030
Gly Ile Arg Thr Leu Leu Phe Ala Leu Met Met Ser Leu Pro Ala Leu
                1595                1600                1605
```

```
                                                              -continued

TTC AAC ATC GGC CTC CTC CTC TTC CTC GTC ATG TTC ATC TAC TCC ATC       5078
Phe Asn Ile Gly Leu Leu Leu Phe Leu Val Met Phe Ile Tyr Ser Ile
1610                1615                1620                1625

TTC GGC ATG GCC AGC TTC GCT AAC GTC GTG GAC GAG GCC GGC ATC GAC       5126
Phe Gly Met Ala Ser Phe Ala Asn Val Val Asp Glu Ala Gly Ile Asp
                1630                1635                1640

GAC ATG TTC AAC TTC AAG ACC TTT GGC AAC AGC ATG CTG TGC CTG TTC       5174
Asp Met Phe Asn Phe Lys Thr Phe Gly Asn Ser Met Leu Cys Leu Phe
            1645                1650                1655

CAG ATC ACC ACC TCG GCC GGC TGG GAC GGC CTC CTC AGC CCC ATC CTC       5222
Gln Ile Thr Thr Ser Ala Gly Trp Asp Gly Leu Leu Ser Pro Ile Leu
        1660                1665                1670

AAC ACG GGG CCT CCC TAC TGC GAC CCC AAC CTG CCC AAC AGC AAC GGC       5270
Asn Thr Gly Pro Pro Tyr Cys Asp Pro Asn Leu Pro Asn Ser Asn Gly
    1675                1680                1685

TCC CGG GGG AAC TGC GGG AGC CCG GCG GTG GGC ATC ATC TTC TTC ACC       5318
Ser Arg Gly Asn Cys Gly Ser Pro Ala Val Gly Ile Ile Phe Phe Thr
1690                1695                1700                1705

ACC TAC ATC ATC ATC TCC TTC CTC ATC GTG GTC AAC ATG TAC ATC GCA       5366
Thr Tyr Ile Ile Ile Ser Phe Leu Ile Val Val Asn Met Tyr Ile Ala
                1710                1715                1720

GTG ATT CTG GAG AAC TTC AAC GTA GCC ACC GAG GAG AGC ACG GAG CCC       5414
Val Ile Leu Glu Asn Phe Asn Val Ala Thr Glu Glu Ser Thr Glu Pro
            1725                1730                1735

CTG AGC GAG GAC GAC TTC GAC ATG TTC TAT GAG ACC TGG GAG AAG TTC       5462
Leu Ser Glu Asp Asp Phe Asp Met Phe Tyr Glu Thr Trp Glu Lys Phe
        1740                1745                1750

GAC CCG GAG GCC ACC CAG TTC ATT GCC TTT TCT GCC CTC TCA GAC TTC       5510
Asp Pro Glu Ala Thr Gln Phe Ile Ala Phe Ser Ala Leu Ser Asp Phe
    1755                1760                1765

GCG GAC ACG CTC TCC GGC CCT CTT AGA ATC CCC AAA CCC AAC CAG AAT       5558
Ala Asp Thr Leu Ser Gly Pro Leu Arg Ile Pro Lys Pro Asn Gln Asn
1770                1775                1780                1785

ATA TTA ATC CAG ATG GAC CTG CCG TTG GTC CCC GGG GAT AAG ATC CAC       5606
Ile Leu Ile Gln Met Asp Leu Pro Leu Val Pro Gly Asp Lys Ile His
                1790                1795                1800

TGT CTG GAC ATC CTT TTT GCC TTC ACA AAG AAC GTC TTG GGA GAA TCC       5654
Cys Leu Asp Ile Leu Phe Ala Phe Thr Lys Asn Val Leu Gly Glu Ser
            1805                1810                1815

GGG GAG TTG GAC TCC CTG AAG ACC AAT ATG GAA GAG AAG TTT ATG GCG       5702
Gly Glu Leu Asp Ser Leu Lys Thr Asn Met Glu Glu Lys Phe Met Ala
        1820                1825                1830

ACC AAT CTC TCC AAA GCA TCC TAT GAA CCA ATA GCC ACC ACC CTC CGG       5750
Thr Asn Leu Ser Lys Ala Ser Tyr Glu Pro Ile Ala Thr Thr Leu Arg
    1835                1840                1845

TGG AAG CAG GAA GAC CTC TCA GCC ACA GTC ATT CAA AAG GCC TAC CGG       5798
Trp Lys Gln Glu Asp Leu Ser Ala Thr Val Ile Gln Lys Ala Tyr Arg
1850                1855                1860                1865

AGC TAC ATG CTG CAC CGC TCC TTG ACA CTC TCC AAC ACC CTG CAT GTG       5846
Ser Tyr Met Leu His Arg Ser Leu Thr Leu Ser Asn Thr Leu His Val
                1870                1875                1880

CCC AGG GCT GAG GAG GAT GGC GTG TCA CTT CCC GGG GAA GGC TAC AGT       5894
Pro Arg Ala Glu Glu Asp Gly Val Ser Leu Pro Gly Glu Gly Tyr Ser
            1885                1890                1895

ACA TTC ATG GCA AAC AGT GGA CTC CCG GAC AAA TCA GAA ACT GCC TCT       5942
Thr Phe Met Ala Asn Ser Gly Leu Pro Asp Lys Ser Glu Thr Ala Ser
        1900                1905                1910

GCT ACG TCT TTC CCG CCA TCC TAT GAC AGT GTC ACC AGG GGC CTG AGT       5990
Ala Thr Ser Phe Pro Pro Ser Tyr Asp Ser Val Thr Arg Gly Leu Ser
    1915                1920                1925
```

```
GAC CGG GCC AAC ATT AAC CCA TCT AGC TCA ATG CAA AAT GAA GAT GAG    6038
Asp Arg Ala Asn Ile Asn Pro Ser Ser Ser Met Gln Asn Glu Asp Glu
1930               1935                1940                1945

GTC GCT GCT AAG GAA GGA AAC AGC CCT GGA CCT CAG TGAAGGCACT         6084
Val Ala Ala Lys Glu Gly Asn Ser Pro Gly Pro Gln
         1950                1955

CAGGCATGCA CAGGGCAGGT TCCAATGTCT TTCTCTGCTG TACTAACTCC TTCCCTCTGG  6144

AGGTGGCACC AACCTCCAGC CTCCACCAAT GCATGTCACT GGTCATGGTG TCAGAACTGA  6204

ATGGGGACAT CCTTGAGAAA GCCCCCACCC AATAGGAAT CAAAAGCCAA GGATACTCCT   6264

CCATTCTGAC GTCCCTTCCG AGTTCCCAGA AGATGTCATT GCTCCCTTCT GTTTGTGACC  6324

AGAGACGTGA TTCACCAACT TCTCGGAGCC AGAGACACAT AGCAAAGACT TTTCTGCTGG  6384

TGTCGGGCAG TCTTAGAGAA GTCACGTAGG GGTTGGTACT GAGAATTAGG GTTTGCATGA  6444

CTGCATGCTC ACAGCTGCCG GACAATACCT GTGAGTCGGC CATTAAAATT AATATTTTTA  6504

AAGTTAAAAA AAAAAAAAAA AAA                                          6527
```

(2) INFORMATION FOR SEQ ID NO:8:

(i) SEQUENCE CHARACTERISTICS:
        (A) LENGTH: 1957 amino acids
        (B) TYPE: amino acid
        (D) TOPOLOGY: linear (ii) MOLECULE TYPE: protein (xi) SEQUENCE DESCRIPTION: SEQ ID NO:8:

```
Met Glu Leu Pro Phe Ala Ser Val Gly Thr Thr Asn Phe Arg Arg Phe
1               5                   10                  15

Thr Pro Glu Ser Leu Ala Glu Ile Glu Lys Gln Ile Ala Ala His Arg
                20                  25                  30

Ala Ala Lys Lys Ala Arg Thr Lys His Arg Gly Gln Glu Asp Lys Gly
            35                  40                  45

Glu Lys Pro Arg Pro Gln Leu Asp Leu Lys Asp Cys Asn Gln Leu Pro
    50                  55                  60

Lys Phe Tyr Gly Glu Leu Pro Ala Glu Leu Val Gly Glu Pro Leu Glu
65                  70                  75                  80

Asp Leu Asp Pro Phe Tyr Ser Thr His Arg Thr Phe Met Val Leu Asn
                85                  90                  95

Lys Ser Arg Thr Ile Ser Arg Phe Ser Ala Thr Trp Ala Leu Trp Leu
            100                 105                 110

Phe Ser Pro Phe Asn Leu Ile Arg Arg Thr Ala Ile Lys Val Ser Val
        115                 120                 125

His Ser Trp Phe Ser Ile Phe Ile Thr Ile Thr Ile Leu Val Asn Cys
    130                 135                 140

Val Cys Met Thr Arg Thr Asp Leu Pro Glu Lys Val Glu Tyr Val Phe
145                 150                 155                 160

Thr Val Ile Tyr Thr Phe Glu Ala Leu Ile Lys Ile Leu Ala Arg Gly
                165                 170                 175

Phe Cys Leu Asn Glu Phe Thr Tyr Leu Arg Asp Pro Trp Asn Trp Leu
            180                 185                 190

Asp Phe Ser Val Ile Thr Leu Ala Tyr Val Gly Ala Ala Ile Asp Leu
        195                 200                 205

Arg Gly Ile Ser Gly Leu Arg Thr Phe Arg Val Leu Arg Ala Leu Lys
    210                 215                 220
```

-continued

```
Thr Val Ser Val Ile Pro Gly Leu Lys Val Ile Val Gly Ala Leu Ile
225                 230                 235                 240

His Ser Val Arg Lys Leu Ala Asp Val Thr Ile Leu Thr Val Phe Cys
            245                 250                 255

Leu Ser Val Phe Ala Leu Val Gly Leu Gln Leu Phe Lys Gly Asn Leu
                260                 265                 270

Lys Asn Lys Cys Ile Arg Asn Gly Thr Asp Pro His Lys Ala Asp Asn
            275                 280                 285

Leu Ser Ser Glu Met Ala Glu Tyr Ile Phe Ile Lys Pro Gly Thr Thr
        290                 295                 300

Asp Pro Leu Leu Cys Gly Asn Gly Ser Asp Ala Gly His Cys Pro Gly
305                 310                 315                 320

Gly Tyr Val Cys Leu Lys Thr Pro Asp Asn Pro Asp Phe Asn Tyr Thr
                325                 330                 335

Ser Phe Asp Ser Phe Ala Trp Ala Phe Leu Ser Leu Phe Arg Leu Met
            340                 345                 350

Thr Gln Asp Ser Trp Glu Arg Leu Tyr Gln Gln Thr Leu Arg Ala Ser
            355                 360                 365

Gly Lys Met Tyr Met Val Phe Phe Val Leu Val Ile Phe Leu Gly Ser
        370                 375                 380

Phe Tyr Leu Val Asn Leu Ile Leu Ala Val Val Thr Met Ala Tyr Glu
385                 390                 395                 400

Glu Gln Ser Gln Ala Thr Ile Ala Glu Ile Glu Ala Lys Glu Lys Lys
                405                 410                 415

Phe Gln Glu Ala Leu Glu Val Leu Gln Lys Glu Gln Glu Val Leu Ala
            420                 425                 430

Ala Leu Gly Ile Asp Thr Thr Ser Leu Gln Ser His Ser Gly Ser Pro
        435                 440                 445

Leu Ala Ser Lys Asn Ala Asn Glu Arg Arg Pro Arg Val Lys Ser Arg
    450                 455                 460

Val Ser Glu Gly Ser Thr Asp Asp Asn Arg Ser Pro Gln Ser Asp Pro
465                 470                 475                 480

Tyr Asn Gln Arg Arg Met Ser Phe Leu Gly Leu Ser Ser Gly Arg Arg
                485                 490                 495

Arg Ala Ser His Gly Ser Val Phe His Phe Arg Ala Pro Ser Gln Asp
            500                 505                 510

Ile Ser Phe Pro Asp Gly Ile Thr Pro Asp Asp Gly Val Phe His Gly
        515                 520                 525

Asp Gln Glu Ser Arg Arg Gly Ser Ile Leu Leu Gly Arg Gly Ala Gly
530                 535                 540

Gln Thr Gly Pro Leu Pro Arg Ser Pro Leu Pro Gln Ser Pro Asn Pro
545                 550                 555                 560

Gly Arg Arg His Gly Glu Glu Gly Gln Leu Gly Val Pro Thr Gly Glu
                565                 570                 575

Leu Thr Ala Gly Ala Pro Glu Gly Pro Ala Leu Asp Thr Thr Gly Gln
            580                 585                 590

Lys Ser Phe Leu Ser Ala Gly Tyr Leu Asn Glu Pro Phe Arg Ala Gln
        595                 600                 605

Arg Ala Met Ser Val Val Ser Ile Met Thr Ser Val Ile Glu Glu Leu
    610                 615                 620

Glu Glu Ser Lys Leu Lys Cys Pro Pro Cys Leu Ile Ser Phe Ala Gln
625                 630                 635                 640

Lys Tyr Leu Ile Trp Glu Cys Cys Pro Lys Trp Arg Lys Phe Lys Met
```

-continued

```
                645                 650                 655
Ala Leu Phe Glu Leu Val Thr Asp Pro Phe Ala Glu Leu Thr Ile Thr
                660                 665                 670
Leu Cys Ile Val Val Asn Thr Val Phe Met Ala Met Glu His Tyr Pro
                675                 680                 685
Met Thr Asp Ala Phe Asp Ala Met Leu Gln Ala Gly Asn Ile Val Phe
                690                 695                 700
Thr Val Phe Phe Thr Met Glu Met Ala Phe Lys Ile Ile Ala Phe Asp
705                 710                 715                 720
Pro Tyr Tyr Tyr Phe Gln Lys Lys Trp Asn Ile Phe Asp Cys Val Ile
                725                 730                 735
Val Thr Val Ser Leu Leu Glu Leu Ser Ala Ser Lys Lys Gly Ser Leu
                740                 745                 750
Ser Val Leu Arg Ser Leu Arg Leu Leu Arg Val Phe Lys Leu Ala Lys
                755                 760                 765
Ser Trp Pro Thr Leu Asn Thr Leu Ile Lys Ile Ile Gly Asn Ser Val
                770                 775                 780
Gly Ala Leu Gly Asn Leu Thr Phe Ile Leu Ala Ile Ile Val Phe Ile
785                 790                 795                 800
Phe Ala Leu Val Gly Lys Gln Leu Leu Ser Glu Asp Tyr Gly Cys Arg
                805                 810                 815
Lys Asp Gly Val Ser Val Trp Asn Gly Glu Lys Leu Arg Trp His Met
                820                 825                 830
Cys Asp Phe Phe His Ser Phe Leu Val Val Phe Arg Ile Leu Cys Gly
                835                 840                 845
Glu Trp Ile Glu Asn Met Trp Val Cys Met Glu Val Ser Gln Lys Ser
                850                 855                 860
Ile Cys Leu Ile Leu Phe Leu Thr Val Met Val Leu Gly Asn Leu Val
865                 870                 875                 880
Val Leu Asn Leu Phe Ile Ala Leu Leu Leu Asn Ser Phe Ser Ala Asp
                885                 890                 895
Asn Leu Thr Ala Pro Glu Asp Asp Gly Glu Val Asn Asn Leu Gln Leu
                900                 905                 910
Ala Leu Ala Arg Ile Gln Val Leu Gly His Arg Ala Ser Arg Ala Ile
                915                 920                 925
Ala Ser Tyr Ile Ser Ser His Cys Arg Phe Arg Trp Pro Lys Val Glu
                930                 935                 940
Thr Gln Leu Gly Met Lys Pro Pro Leu Thr Ser Ser Glu Ala Lys Asn
945                 950                 955                 960
His Ile Ala Thr Asp Ala Val Ser Ala Ala Val Gly Asn Leu Thr Lys
                965                 970                 975
Pro Ala Leu Ser Ser Pro Lys Glu Asn His Gly Asp Phe Ile Thr Asp
                980                 985                 990
Pro Asn Val Trp Val Ser Val Pro Ile Ala Glu Gly Glu Ser Asp Leu
                995                 1000                1005
Asp Glu Leu Glu Glu Asp Met Glu Gln Ala Ser Gln Ser Ser Trp Gln
                1010                1015                1020
Glu Glu Asp Pro Lys Gly Gln Gln Glu Gln Leu Pro Gln Val Gln Lys
1025                1030                1035                1040
Cys Glu Asn His Gln Ala Ala Arg Ser Pro Ala Ser Met Met Ser Ser
                1045                1050                1055
Glu Asp Leu Ala Pro Tyr Leu Gly Glu Ser Trp Lys Arg Lys Asp Ser
                1060                1065                1070
```

-continued

```
Pro Gln Val Pro Ala Glu Gly Val Asp Asp Thr Ser Ser Glu Gly
    1075                1080                1085
Ser Thr Val Asp Cys Pro Asp Pro Glu Glu Ile Leu Arg Lys Ile Pro
    1090                1095                1100
Glu Leu Ala Asp Asp Leu Asp Glu Pro Asp Asp Cys Phe Thr Glu Gly
1105                1110                1115                1120
Cys Thr Arg Arg Cys Pro Cys Cys Asn Val Asn Thr Ser Lys Ser Pro
                1125                1130                1135
Trp Ala Thr Gly Trp Gln Val Arg Lys Thr Cys Tyr Arg Ile Val Glu
                1140                1145                1150
His Ser Trp Phe Glu Ser Phe Ile Ile Phe Met Ile Leu Leu Ser Ser
                1155                1160                1165
Gly Ala Leu Ala Phe Glu Asp Asn Tyr Leu Glu Glu Lys Pro Arg Val
                1170                1175                1180
Lys Ser Val Leu Glu Tyr Thr Asp Arg Val Phe Thr Phe Ile Phe Val
1185                1190                1195                1200
Phe Glu Met Leu Leu Lys Trp Val Ala Tyr Gly Phe Lys Tyr Phe
                1205                1210                1215
Thr Asn Ala Trp Cys Trp Leu Asp Phe Leu Ile Val Asn Ile Ser Leu
                1220                1225                1230
Thr Ser Leu Ile Ala Lys Ile Leu Glu Tyr Ser Asp Val Ala Ser Ile
                1235                1240                1245
Lys Ala Leu Arg Thr Leu Arg Ala Leu Arg Pro Leu Arg Ala Leu Ser
                1250                1255                1260
Arg Phe Glu Gly Met Arg Val Val Asp Ala Leu Val Gly Ala Ile
1265                1270                1275                1280
Pro Ser Ile Met Asn Val Leu Leu Val Cys Leu Ile Phe Trp Leu Ile
                1285                1290                1295
Phe Ser Ile Met Gly Val Asn Leu Phe Ala Gly Lys Phe Ser Lys Cys
                1300                1305                1310
Val Asp Thr Arg Asn Asn Pro Phe Ser Asn Val Asn Ser Thr Met Val
                1315                1320                1325
Asn Asn Lys Ser Glu Cys His Asn Gln Asn Ser Thr Gly His Phe Phe
                1330                1335                1340
Trp Val Asn Val Lys Val Asn Phe Asp Asn Val Ala Met Gly Tyr Leu
1345                1350                1355                1360
Ala Leu Leu Gln Val Ala Thr Phe Lys Gly Trp Met Asp Ile Met Tyr
                1365                1370                1375
Ala Ala Val Asp Ser Gly Glu Ile Asn Ser Gln Pro Asn Trp Glu Asn
                1380                1385                1390
Asn Leu Tyr Met Tyr Leu Tyr Phe Val Val Phe Ile Ile Phe Gly Gly
                1395                1400                1405
Phe Phe Thr Leu Asn Leu Phe Val Gly Val Ile Ile Asp Asn Phe Asn
                1410                1415                1420
Gln Gln Lys Lys Lys Leu Gly Gly Gln Asp Ile Phe Met Thr Glu Glu
1425                1430                1435                1440
Gln Lys Lys Tyr Tyr Asn Ala Met Lys Lys Leu Gly Ser Lys Pro
                1445                1450                1455
Gln Lys Pro Ile Pro Arg Pro Leu Asn Lys Tyr Gln Gly Phe Val Phe
                1460                1465                1470
Asp Ile Val Thr Arg Gln Ala Phe Asp Ile Ile Ile Met Val Leu Ile
                1475                1480                1485
```

```
Cys Leu Asn Met Ile Thr Met Met Val Glu Thr Asp Glu Gln Gly Glu
    1490                1495                1500

Glu Lys Thr Lys Val Leu Gly Arg Ile Asn Gln Phe Phe Val Ala Val
1505                1510                1515                1520

Phe Thr Gly Glu Cys Val Met Lys Met Phe Ala Leu Arg Gln Tyr Tyr
                1525                1530                1535

Phe Thr Asn Gly Trp Asn Val Phe Asp Phe Ile Val Val Ile Leu Ser
            1540                1545                1550

Ile Gly Ser Leu Leu Phe Ser Ala Ile Leu Lys Ser Leu Glu Asn Tyr
        1555                1560                1565

Phe Ser Pro Thr Leu Phe Arg Val Ile Arg Leu Ala Arg Ile Gly Arg
    1570                1575                1580

Ile Leu Arg Leu Ile Arg Ala Ala Lys Gly Ile Arg Thr Leu Leu Phe
1585                1590                1595                1600

Ala Leu Met Met Ser Leu Pro Ala Leu Phe Asn Ile Gly Leu Leu Leu
                1605                1610                1615

Phe Leu Val Met Phe Ile Tyr Ser Ile Phe Gly Met Ala Ser Phe Ala
            1620                1625                1630

Asn Val Val Asp Glu Ala Gly Ile Asp Asp Met Phe Asn Phe Lys Thr
        1635                1640                1645

Phe Gly Asn Ser Met Leu Cys Leu Phe Gln Ile Thr Thr Ser Ala Gly
    1650                1655                1660

Trp Asp Gly Leu Leu Ser Pro Ile Leu Asn Thr Gly Pro Pro Tyr Cys
1665                1670                1675                1680

Asp Pro Asn Leu Pro Asn Ser Asn Gly Ser Arg Gly Asn Cys Gly Ser
                1685                1690                1695

Pro Ala Val Gly Ile Ile Phe Phe Thr Thr Tyr Ile Ile Ser Phe
            1700                1705                1710

Leu Ile Val Val Asn Met Tyr Ile Ala Val Ile Leu Glu Asn Phe Asn
        1715                1720                1725

Val Ala Thr Glu Glu Ser Thr Glu Pro Leu Ser Glu Asp Asp Phe Asp
    1730                1735                1740

Met Phe Tyr Glu Thr Trp Glu Lys Phe Asp Pro Glu Ala Thr Gln Phe
1745                1750                1755                1760

Ile Ala Phe Ser Ala Leu Ser Asp Phe Ala Asp Thr Leu Ser Gly Pro
                1765                1770                1775

Leu Arg Ile Pro Lys Pro Asn Gln Asn Ile Leu Ile Gln Met Asp Leu
            1780                1785                1790

Pro Leu Val Pro Gly Asp Lys Ile His Cys Leu Asp Ile Leu Phe Ala
        1795                1800                1805

Phe Thr Lys Asn Val Leu Gly Glu Ser Gly Glu Leu Asp Ser Leu Lys
    1810                1815                1820

Thr Asn Met Glu Glu Lys Phe Met Ala Thr Asn Leu Ser Lys Ala Ser
1825                1830                1835                1840

Tyr Glu Pro Ile Ala Thr Thr Leu Arg Trp Lys Gln Glu Asp Leu Ser
                1845                1850                1855

Ala Thr Val Ile Gln Lys Ala Tyr Arg Ser Tyr Met Leu His Arg Ser
            1860                1865                1870

Leu Thr Leu Ser Asn Thr Leu His Val Pro Arg Ala Glu Glu Asp Gly
        1875                1880                1885

Val Ser Leu Pro Gly Glu Gly Tyr Ser Thr Phe Met Ala Asn Ser Gly
    1890                1895                1900

Leu Pro Asp Lys Ser Glu Thr Ala Ser Ala Thr Ser Phe Pro Pro Ser
```

```
                1905              1910              1915              1920
Tyr Asp Ser Val Thr Arg Gly Leu Ser Asp Arg Ala Asn Ile Asn Pro
                     1925              1930              1935

Ser Ser Ser Met Gln Asn Glu Asp Glu Val Ala Ala Lys Glu Gly Asn
                1940              1945              1950

Ser Pro Gly Pro Gln
       1955
```

(2) INFORMATION FOR SEQ ID NO:9:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

CAGCTTCGCT CAGAAGTATC T                      21

(2) INFORMATION FOR SEQ ID NO:10:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

TTCTCGCCGT TCCACACGGA GA                     22

(2) INFORMATION FOR SEQ ID NO:11:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO:11:

Phe Arg Leu Met
1

(2) INFORMATION FOR SEQ ID NO:12:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO:12:

Thr Gln Asp Phe Trp Glu Asn Leu Tyr
1          5

(2) INFORMATION FOR SEQ ID NO:13:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO:13:

Thr Gln Asp Tyr Trp Glu Asn Leu Tyr
1               5

(2) INFORMATION FOR SEQ ID NO:14:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO:14:

Thr Gln Asp Cys Trp Glu Arg Leu Tyr
1               5

(2) INFORMATION FOR SEQ ID NO:15:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO:15:

Thr Gln Asp Ser Trp Glu Arg Leu Tyr
1               5

(2) INFORMATION FOR SEQ ID NO:16:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO:16:

Thr Gln Asp Phe Trp Glu Arg Leu Tyr
1               5

(2) INFORMATION FOR SEQ ID NO:17:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO:17:

Thr Gln Asp Ser Trp Glu Arg
1               5

(2) INFORMATION FOR SEQ ID NO:18:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:18:

```
Gly Ser Thr Asp Asp Asn Arg Ser Pro Gln Ser Asp Pro Tyr Asn
1               5                   10                  15
```

(2) INFORMATION FOR SEQ ID NO:19:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:19:

```
Ser Pro Lys Glu Asn His Gly Asp Phe Ile
1               5                   10
```

(2) INFORMATION FOR SEQ ID NO:20:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO:20:

```
Pro Asn His Asn Gly Ser Arg Gly Asn
1               5
```

(2) INFORMATION FOR SEQ ID NO:21:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:21:

```
Arg Leu Leu Arg Val Phe Lys Leu Ala Lys Ser Trp Pro Thr Leu
1               5                   10                  15
```

(2) INFORMATION FOR SEQ ID NO:22:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:22:

```
GCTTGCTGCG GGTCTTCAAG C                                                 21
```

(2) INFORMATION FOR SEQ ID NO:23:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:23:

```
Leu Arg Ala Leu Pro Leu Arg Ala Leu Ser Arg Phe Glu Gly
1               5                   10
```

(2) INFORMATION FOR SEQ ID NO:24:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:24:

ATCGAGACAG AGCCCGCAGC G                                                             21

(2) INFORMATION FOR SEQ ID NO:25:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:25:

ACGGGTGCCG CAAGGACGGC GTCTCCGTGT GGAACGGCGA GAAG                44

(2) INFORMATION FOR SEQ ID NO:26:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:26:

GGCTATCCTT CCTCTTCCAG CTCTCACCCA GGTATGGAGC CAGGT               45

(2) INFORMATION FOR SEQ ID NO:27:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:27:

TCCCGTACGC TGCAGCTCTT T                                                            21

(2) INFORMATION FOR SEQ ID NO:28:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:28:

CCCGGGGAAG GCTAC                                                                     15

(2) INFORMATION FOR SEQ ID NO:29:

(i) SEQUENCE CHARACTERISTICS:
        (A) LENGTH: 15 base pairs

-continued

```
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:29:

GTCGACACCA GAAAT                                                      15

(2) INFORMATION FOR SEQ ID NO:30:

(i) SEQUENCE CHARACTERISTICS:
          (A) LENGTH: 30 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO:30:

GGATCCTCTA GAGTCGACCT GCAGAAGGAA                                      30

(2) INFORMATION FOR SEQ ID NO:31:

(i) SEQUENCE CHARACTERISTICS:
          (A) LENGTH: 24 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO:31:

TGACGCAGGA CTCCTGGGAG CGCC                                            24
```

What is claimed is:

1. A purified nucleic acid sequence encoding a sodium channel protein wherein said nucleic acid sequence comprises the coding portion of the nucleic acid sequence shown in SEQ ID NO:1, SEQ ID NO:3, SEQ ID NO:5 or SEQ ID NO:7.

2. The purified nucleic acid sequence of claim 1 wherein said nucleic acid sequence comprises the coding portion of the nucleic acid sequence shown in SEQ ID NO:1.

3. A vector comprising a nucleic acid sequence of claim 1 or 2.

4. A host cell transformed or transfected with a nucleic acid sequence of claim 1 or 2.

5. A method of producing a mammalian sensory neuron sodium channel protein, wherein the sodium channel is insensitive to tetrodotoxin, comprising expressing a nucleic acid sequence of claim 1 in a host cell transformed with said nucleic acid sequence.

6. A nucleic acid sequence of claim 1 wherein said nucleic acid sequence comprises the coding portion of the nucleic acid sequence shown in SEQ ID NO:3.

7. A vector comprising a nucleic acid sequence of claim 6.

8. A host cell transformed or transfected with a nucleic acid sequence of claim 6.

9. A method of producing a mammalian sensory neuron sodium channel protein, wherein the sodium channel is insensitive to tetrodotoxin, comprising expressing the nucleic acid sequence of claim 6 in a host cell transformed with said nucleic acid sequence.

10. A nucleic acid sequence of claim 1 wherein said nucleic acid sequence comprises the coding portion of the nucleic acid sequence shown in SEQ ID NO:5.

11. A vector comprising a nucleic acid sequence of claim 10.

12. A host cell transformed or transfected with a nucleic acid sequence of claim 10.

13. A method of producing a mammalian sensory neuron sodium channel protein, wherein the sodium channel is insensitive to tetrodotoxin, comprising expressing the nucleic acid sequence of claim 10 in a host cell transformed with said nucleic acid sequence.

14. A nucleic acid sequence of claim 1 wherein said nucleic acid sequence comprises the coding portion of the nucleic acid sequence shown in SEQ ID NO:7.

15. A vector comprising a nucleic acid sequence of claim 14.

16. A host cell transformed or transfected with a nucleic acid sequence of claim 14.

17. A method of producing a mammalian sensory neuron sodium channel protein, wherein the sodium channel is insensitive to tetrodotoxin, comprising expression the nucleic acid sequence of claim 14 in a host cell transformed with said nucleic acid.

* * * * *